(12) United States Patent
Lauterbach et al.

(10) Patent No.: US 10,512,684 B2
(45) Date of Patent: Dec. 24, 2019

(54) METHODS AND COMPOSITIONS FOR INTRA-NASAL IMMUNIZATION WITH RECOMBINANT MVA ENCODING FLAGELLIN

(71) Applicant: Bavarian Nordic A/S, Kvistgaard (DK)

(72) Inventors: Henning Lauterbach, Eching (DE); Hubertus Hochrein, Munich (DE); Stephanie Sanos, Munich (DE)

(73) Assignee: Bavarian Nordic A/S, Kvistgaard (DK)

( * ) Notice: Subject to any disclaimer, the term of this patent is extended or adjusted under 35 U.S.C. 154(b) by 0 days.

(21) Appl. No.: 15/512,820

(22) PCT Filed: Sep. 25, 2015

(86) PCT No.: PCT/EP2015/072076
§ 371 (c)(1),
(2) Date: Mar. 20, 2017

(87) PCT Pub. No.: WO2016/046357
PCT Pub. Date: Mar. 31, 2016

(65) Prior Publication Data
US 2017/0290909 A1    Oct. 12, 2017

(30) Foreign Application Priority Data
Sep. 26, 2014 (EP) ..................... 14186588

(51) Int. Cl.
| | | |
|---|---|---|
| *A61K 39/285* | (2006.01) | |
| *A61K 39/39* | (2006.01) | |
| *C07K 14/255* | (2006.01) | |
| *A61K 39/295* | (2006.01) | |
| *C12N 7/04* | (2006.01) | |
| *A61K 39/00* | (2006.01) | |

(52) U.S. Cl.
CPC .......... *A61K 39/285* (2013.01); *A61K 39/295* (2013.01); *A61K 39/39* (2013.01); *C07K 14/255* (2013.01); *C12N 7/045* (2013.01); *A61K 2039/53* (2013.01); *A61K 2039/55516* (2013.01); *A61K 2039/55544* (2013.01); *A61K 2039/55594* (2013.01); *A61K 2039/57* (2013.01); *A61K 2039/572* (2013.01); *A61K 2039/58* (2013.01); *A61K 2039/6031* (2013.01); *A61K 2039/6068* (2013.01); *A61K 2039/64* (2013.01); *C12N 2700/00* (2013.01); *C12N 2710/24143* (2013.01)

(58) Field of Classification Search
CPC .... A61K 39/285; A61K 39/295; A61K 39/39; A61K 2039/64; A61K 2039/53; A61K 2039/55516; A61K 2039/55544; A61K 2039/55594; A61K 2039/58; A61K 2039/6068; A61K 2039/6031; A61K 2039/572; A61K 2039/57; A61K 2300/00; A61K 39/12; A61K 39/00; A61K 38/164; A61K 2039/543; A61K 2039/55511; A61K 2039/55555; A61K 2039/6075; A61K 35/74; A61K 39/02; A61K 2039/541; C12N 7/045; C12N 2700/00; C12N 2710/24143; C12N 7/00; C12N 2710/24034; C12N 2710/24134; C07K 14/255; C07K 14/005; C07K 2319/00
See application file for complete search history.

(56) References Cited

U.S. PATENT DOCUMENTS

2009/0191157 A1* 7/2009 Albrecht ................ A61K 39/35
424/93.2

FOREIGN PATENT DOCUMENTS

| WO | WO 89/10967 | 11/1989 |
|---|---|---|
| WO | WO 2007/103048 | 9/2007 |
| WO | WO 2009/079564 | 6/2009 |
| WO | WO 2011/095649 | 8/2011 |
| WO | WO 2014/037124 | 3/2014 |

OTHER PUBLICATIONS

McClelland M, Sanderson KE, et. al. Flagellar biosynthesis; flagellin, filament structural protein [*Salmonella typhimurium* LT2]. NCBI Reference Sequence: NP_460912.1. Dep. Nov. 7, 2001.*
Tominaga A. *Salmonella enterica* subsp. *enterica* serovar Typhimurium gene for phase 1 flagellin, complete cds. GenBank: D13689.1. Dep. Mar. 31, 2009.*
Sanos SL, Kassub R, Testori M, Geiger M, Pätzold J, Giessel R, Knallinger J, Bathke B, Gräbnitz F, Brinkmann K, Chaplin P, Suter M, Hochrein H, Lauterbach H. NLRC4 Inflammasome-Driven Immunogenicity of a Recombinant MVA Mucosal Vaccine Encoding Flagellin. Front Immunol. Jan. 24, 2018;8:1988. eCollection 2017.*
Zhang L, Wang W, Wang S. Effect of vaccine administration modality on immunogenicity and efficacy. Expert Rev Vaccines. 2015; 14(11):1509-23. Epub Aug. 27, 2015.*
das Graças Luna M, Sardella FF, Ferreira LC. *Salmonella flagellin* fused with a linear epitope of colonization factor antigen I (CFA/I) can prime antibody responses against homologous and heterologous fimbriae of enterotoxigenic *Escherichia coli*. Res Microbiol. Sep. 2000;151(7):575-82.*
Lauterbach et al., Genetic Adjuvantation of Recombinant MVA with CD40L potentiates CD8T cell mediated immunity, Frontiers in Immunology, 4: 1-16 (2013).
Skountzou et al., *Salmonella flagellins* are potent adjuvants for intranasally administered whole inactivated influenza vaccine, Vaccine, 28: 4103-4112 (2010).
Search Report and Written Opinion of the International Search Authority for PCT/EP2015/072076 dated Dec. 7, 2015.

* cited by examiner

*Primary Examiner* — Rachel B Gill

(57) ABSTRACT

Provided herein are immunogenic compositions comprising a recombinant modified vaccinia virus Ankara (MVA) comprising a nucleic acid sequence encoding a flagellin, and a nucleic acid sequence encoding a heterologous disease-associated antigen, wherein the immunogenic composition induces increased T-cell and antibody mediated immune responses specific for the heterologous disease-associated antigen when administered to a subject, e.g. a human subject, and related methods and uses.

27 Claims, 12 Drawing Sheets
Specification includes a Sequence Listing.

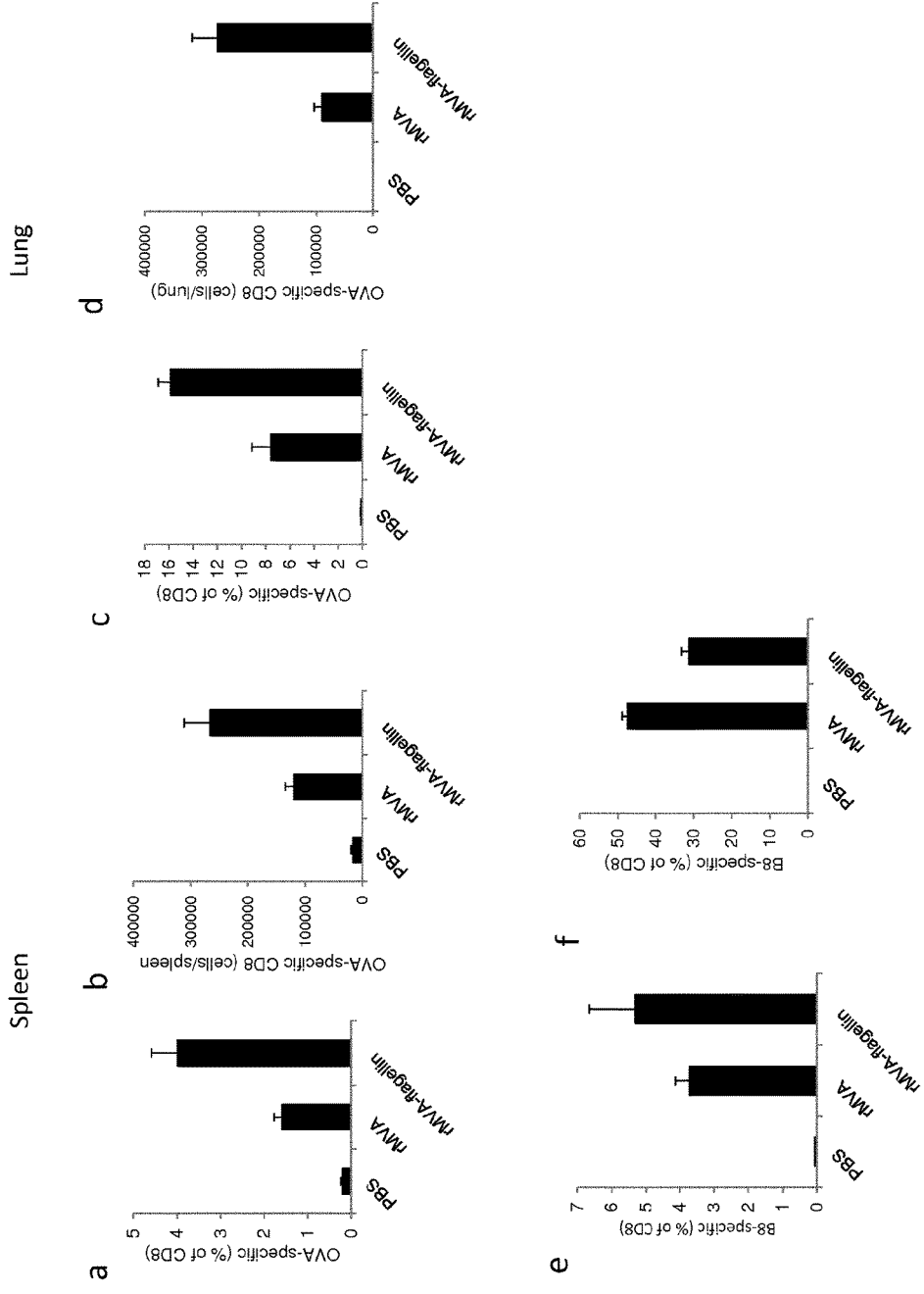
Fig 1. Enhanced OVA-specific CTL response in spleen (a,b) and lung (c,d). B8-specific response in spleen (e) and lung (f)

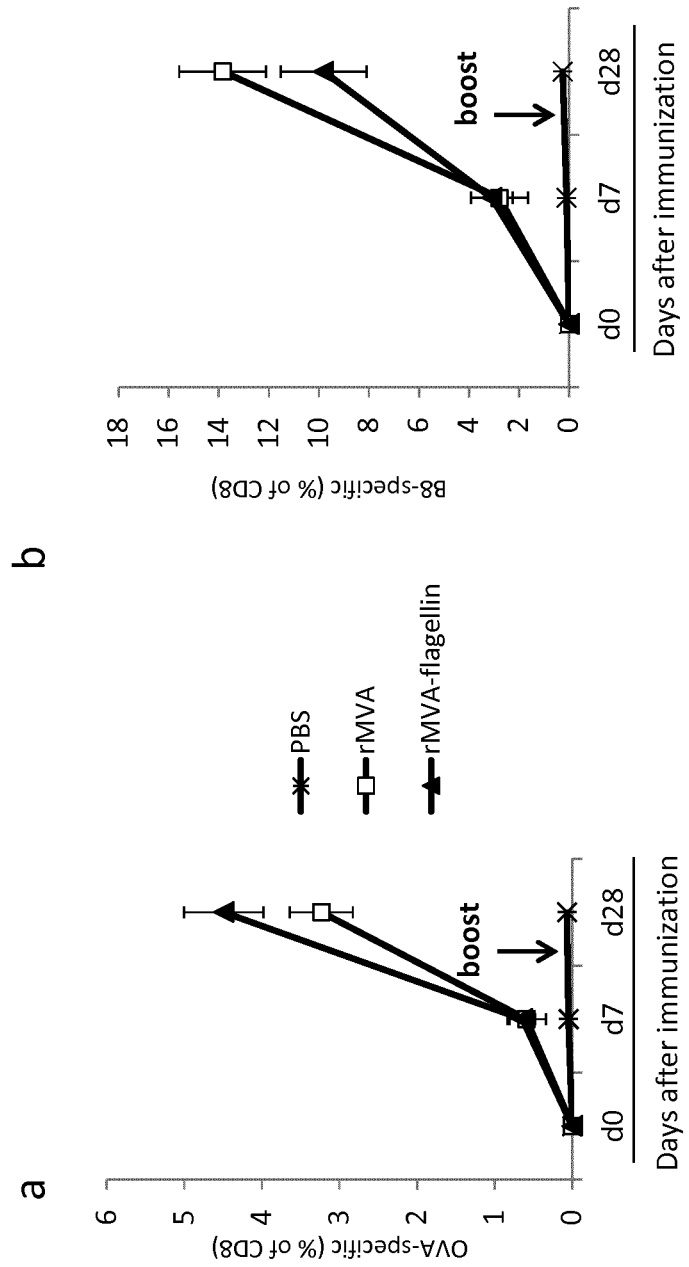
Fig 2. Blood B8 (a) and OVA (b) -specific CTL response

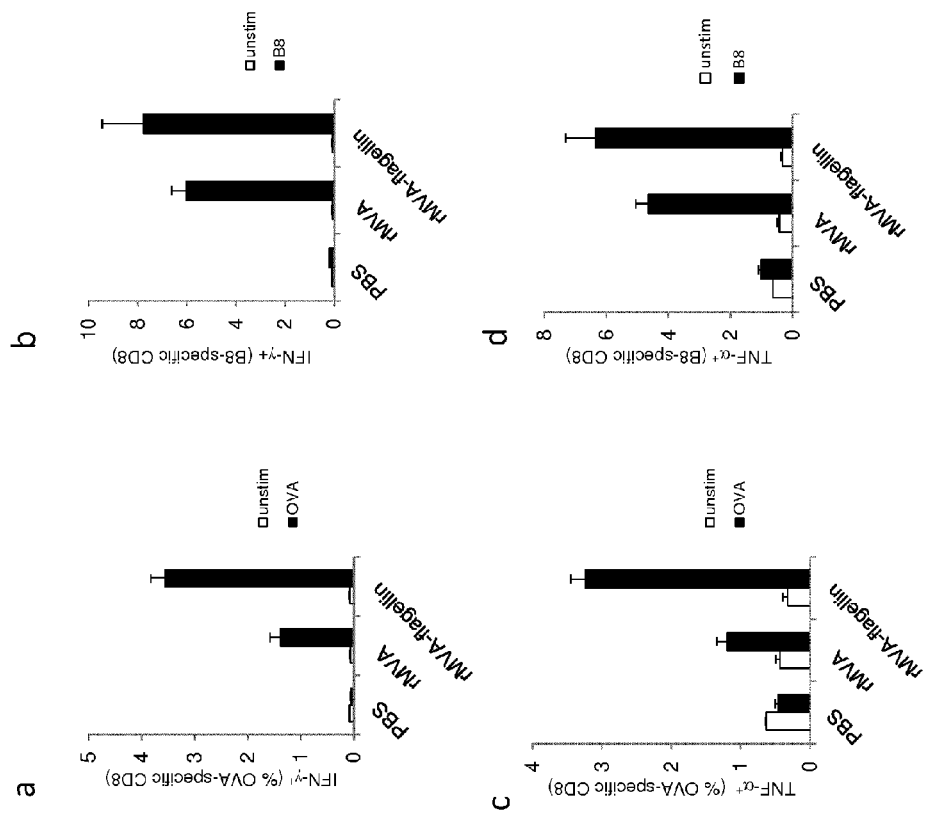
Fig 3. Enhanced CTL-producing cytokines in the spleen after i.n MVA-flagellin immunization: IFNγ(a,b), TNF-α (c,d)

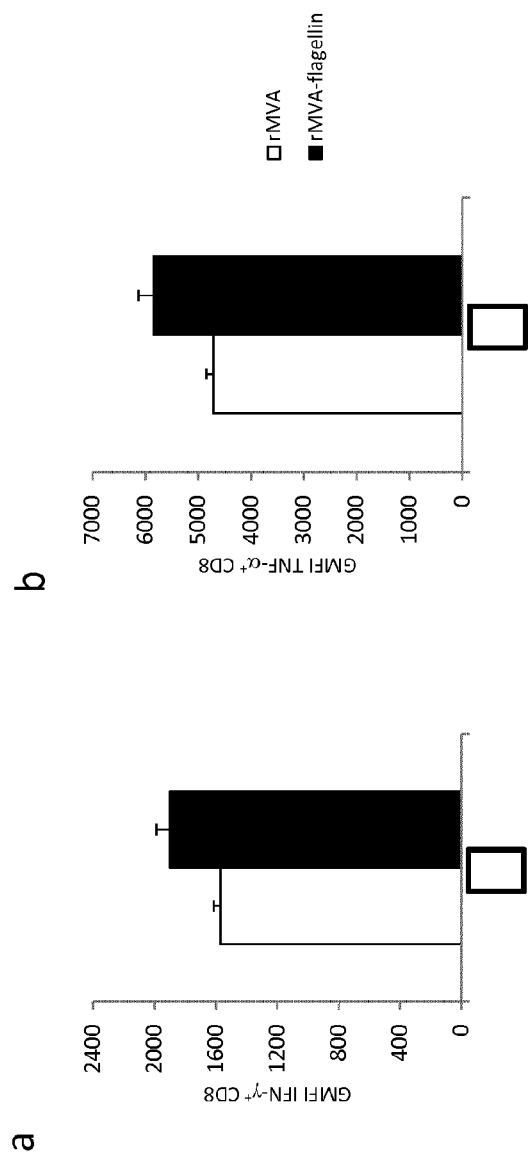
Fig 4. Enhanced quality of OVA-specific CTL responses in the spleen after *i.n* rMVA-flagellin immunization: IFNγ(a), TNF-α (b)

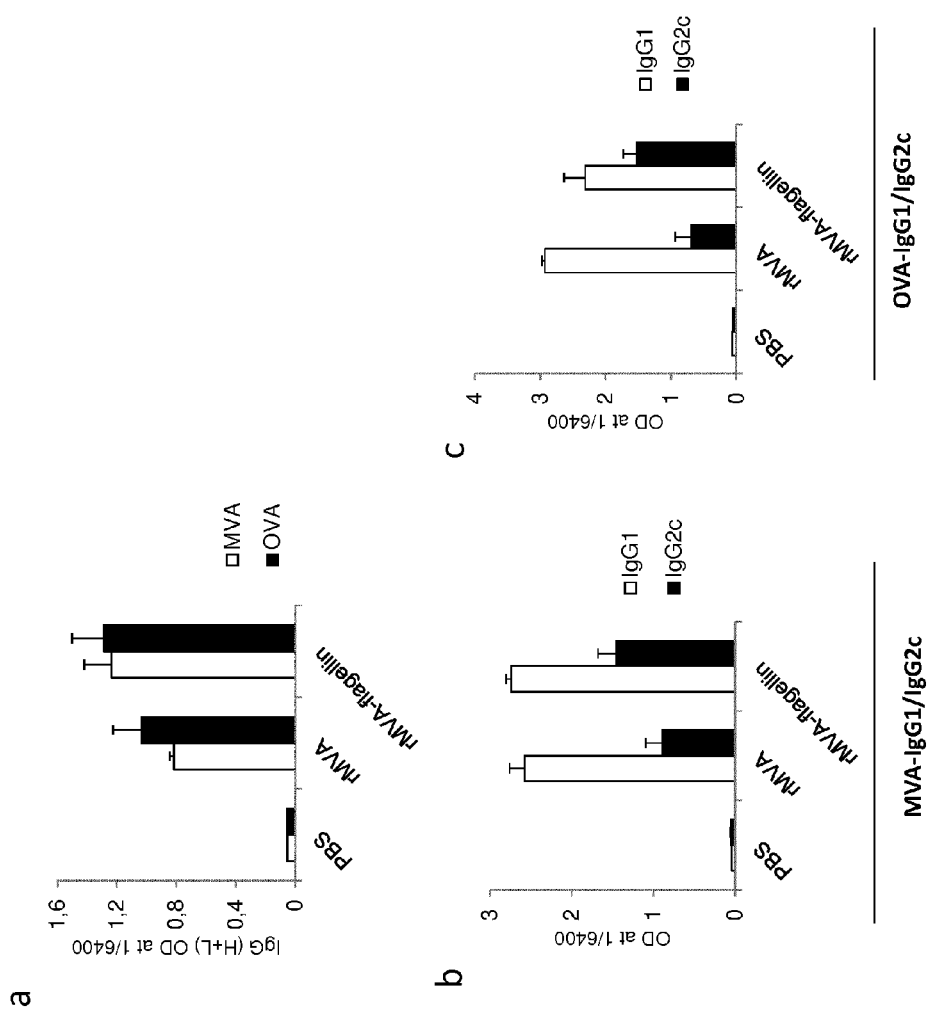
Fig 5. Serum IgG antibody responses

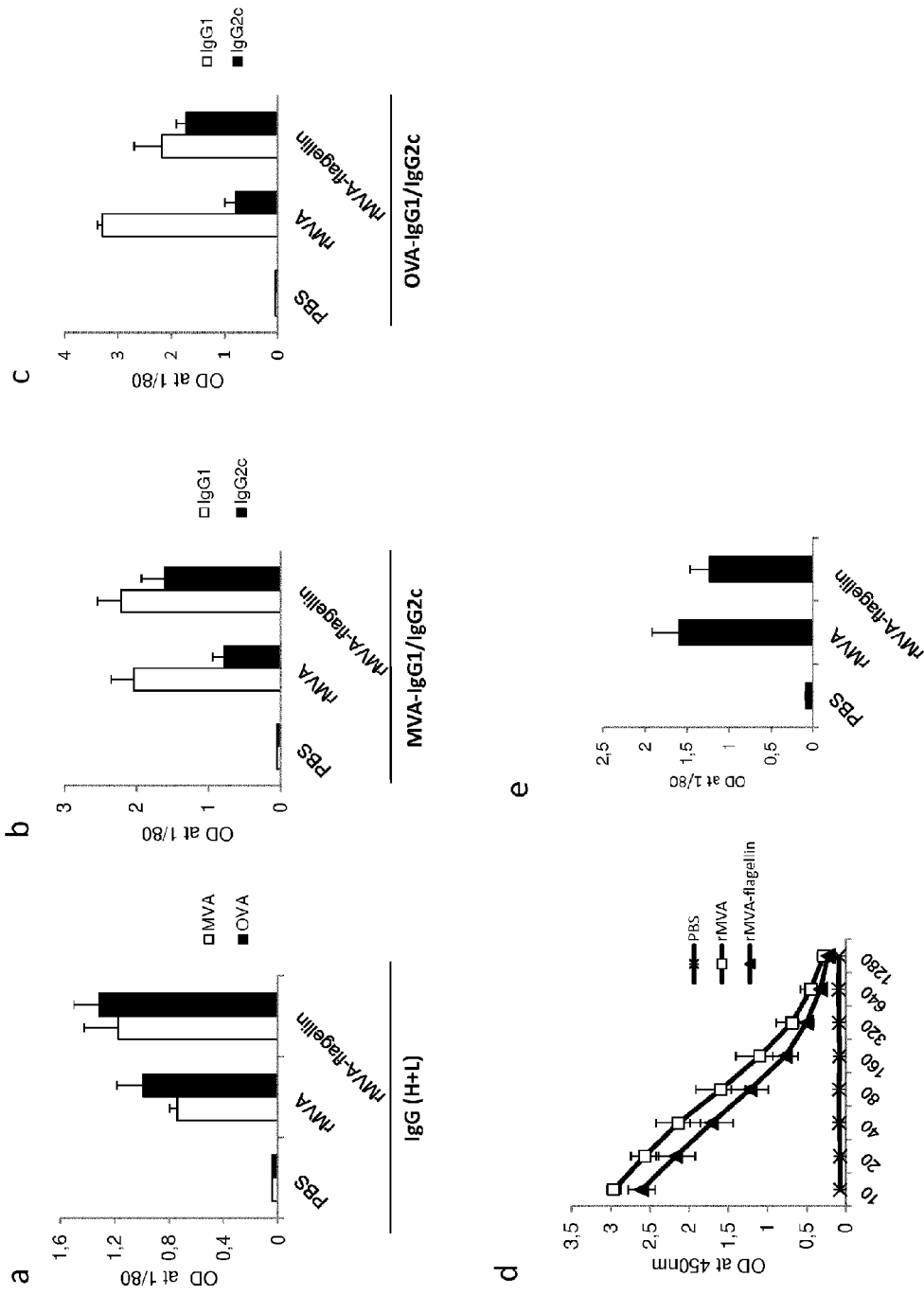
Fig 6. BAL antibody responses, IgG (a, b, c) and antigen-specific IgA (d, e)

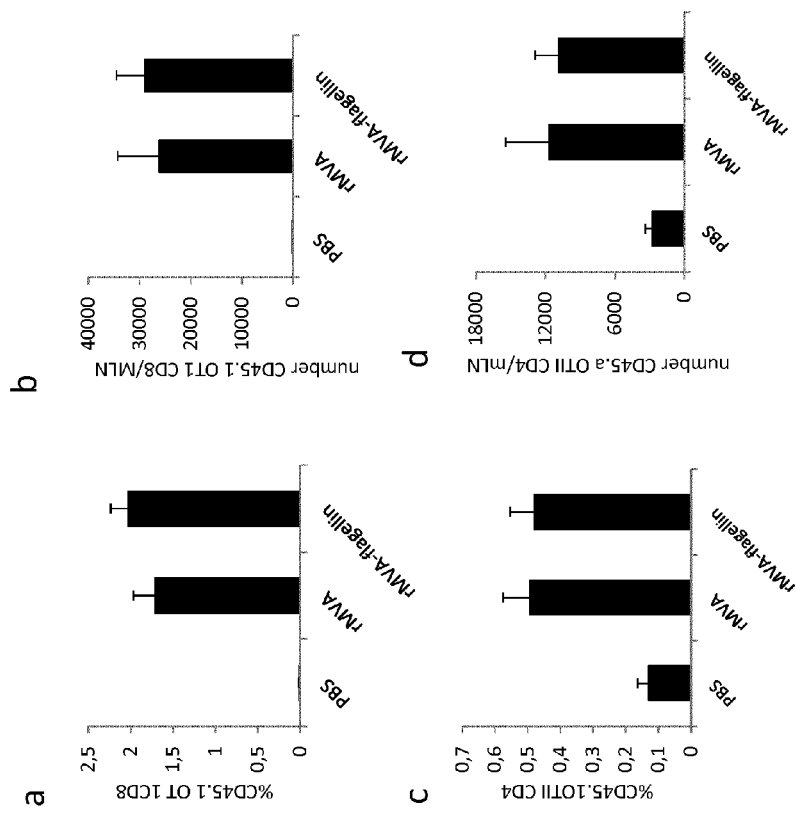
Fig 7. Homing of OT-II CD4+ and OT-I CD8+ T cells in the mLN 7 days after i.n rMVA immunization

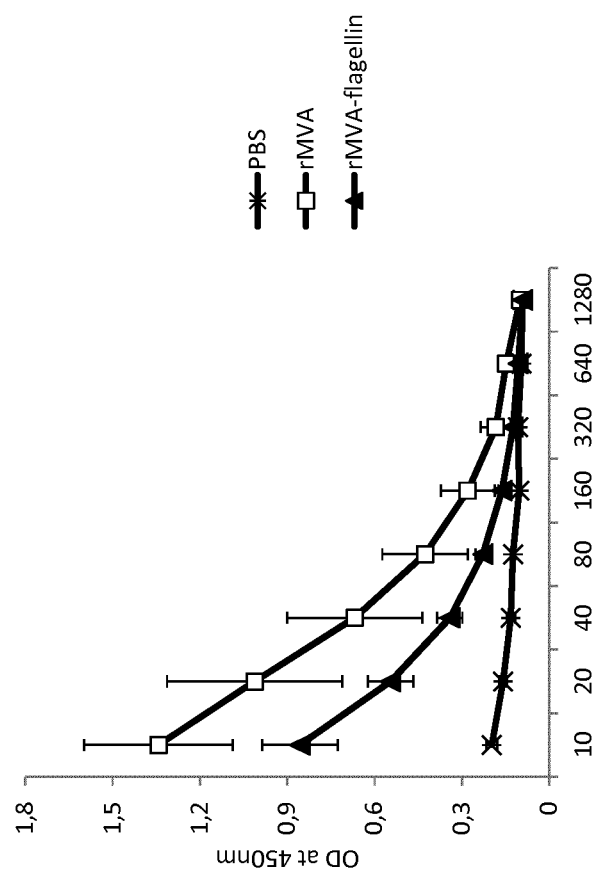
Fig 8. Antigen-specific IgA in intestinal washes after *i.n* rMVA immunization

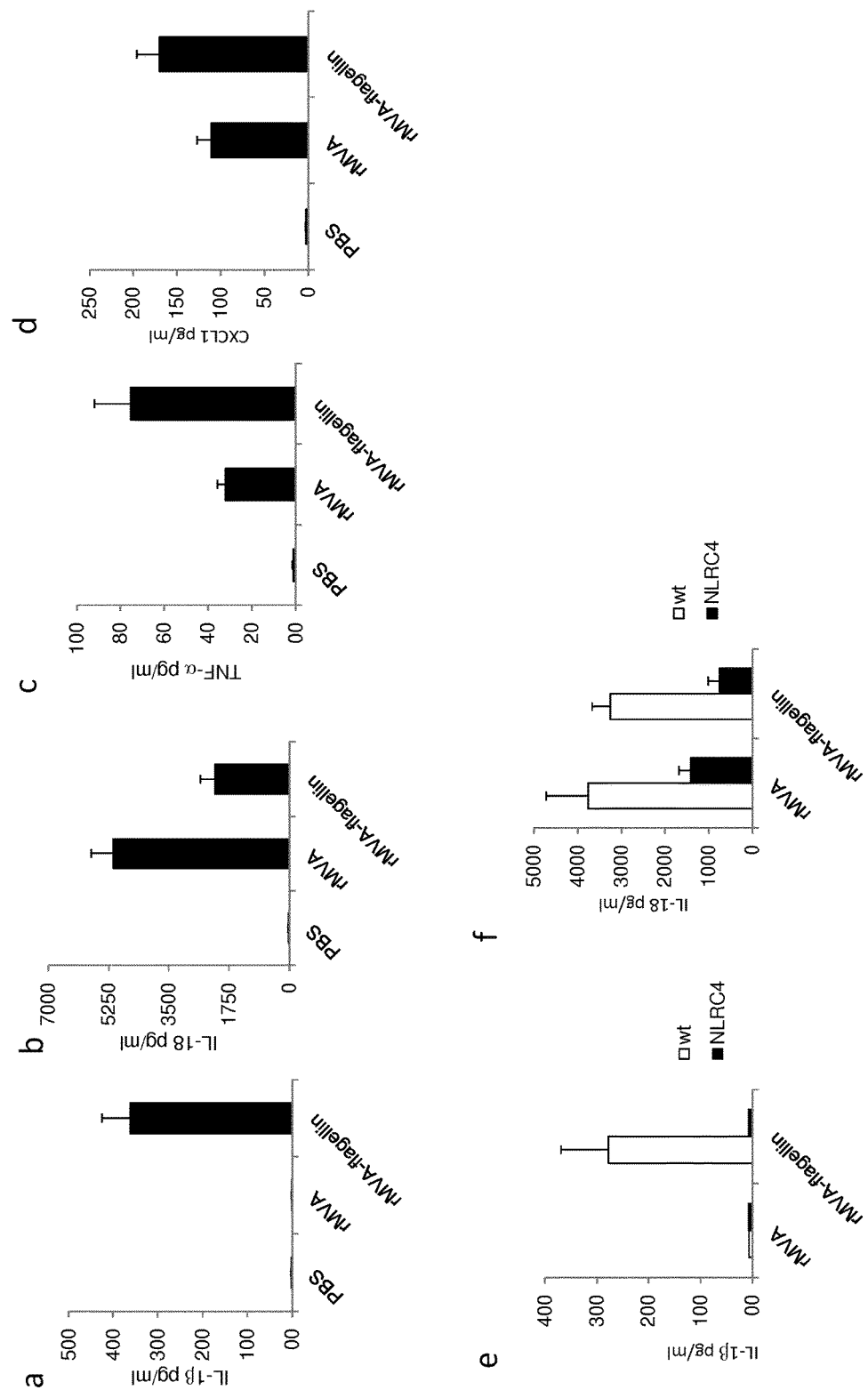
Fig. 9 Innate immune response in BAL 24h after i.n immunization

Fig. 10 TLR5-mediated recognition of rMVA-flagellin transduced-FLDC

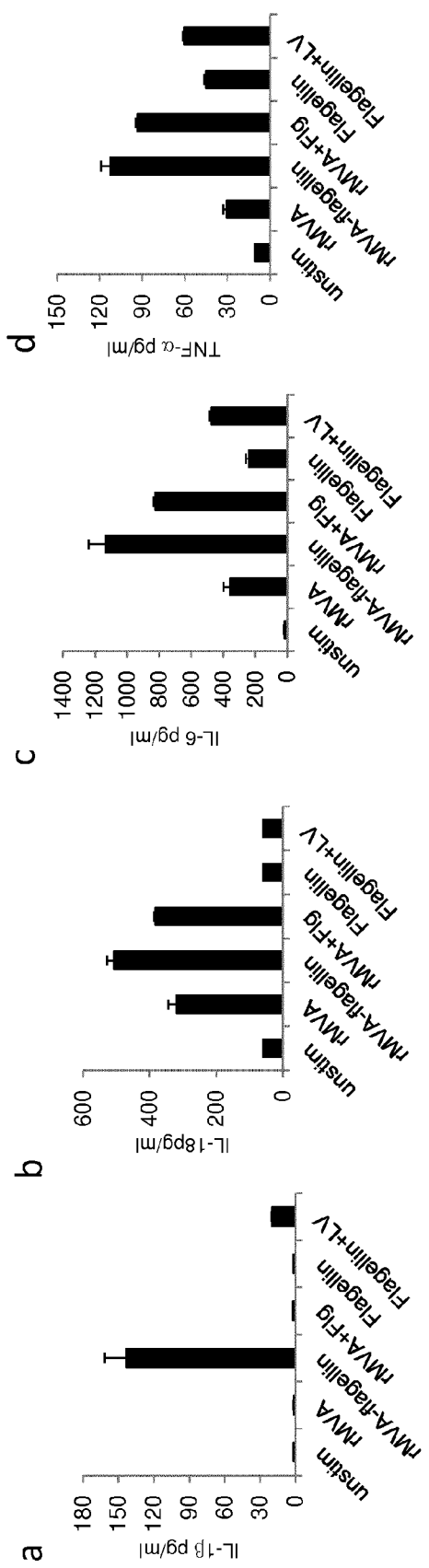
Fig. 11 Inflammasome and TLR5-mediated recognition of rMVA-flagellin transduced-FLDC

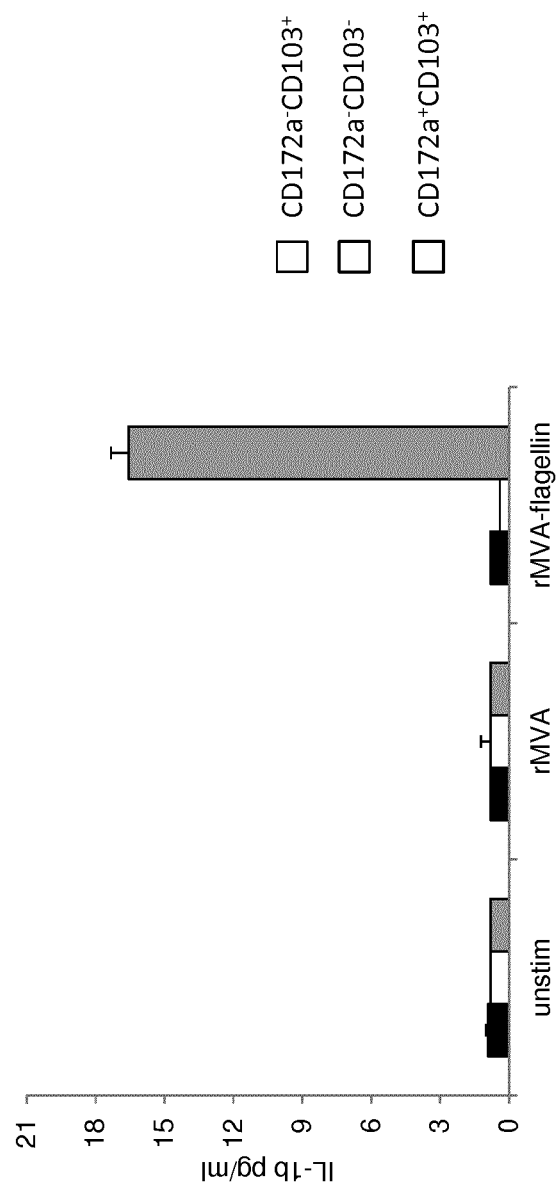
Fig. 12 rMVA-flagellin stimulation of mucosal DC

SEQUENCE LISTING

<160> NUMBER OF SEQ ID NOS: 4

<210> SEQ ID NO 1
<211> LENGTH: 495
<212> TYPE: PRT
<213> ORGANISM: Salmonella typhimurium

<400> SEQUENCE: 1

Met Ala Gln Val Ile Asn Thr Asn Ser Leu Ser Leu Leu Thr Gln Asn
1               5                   10                  15

Asn Leu Asn Lys Ser Gln Ser Ala Leu Gly Thr Ala Ile Glu Arg Leu
                20                  25                  30

Ser Ser Gly Leu Arg Ile Asn Ser Ala Lys Asp Asp Ala Ala Gly Gln
            35                  40                  45

Ala Ile Ala Asn Arg Phe Thr Ala Asn Ile Lys Gly Leu Thr Gln Ala
        50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ala
                85                  90                  95

Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Ser Gly
            115                 120                 125

Gln Thr Gln Phe Asn Gly Val Lys Val Leu Ala Gln Asp Asn Thr Leu
        130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Thr Leu Asn Val Gln
                165                 170                 175

Gln Lys Tyr Lys Val Ser Asp Thr Ala Ala Thr Val Thr Gly Tyr Ala
            180                 185                 190

Asp Thr Thr Ile Ala Leu Asp Asn Ser Thr Phe Lys Ala Ser Ala Thr
        195                 200                 205

Gly Leu Gly Gly Thr Asp Gln Lys Ile Asp Gly Asp Leu Lys Phe Asp
210                 215                 220

Asp Thr Thr Gly Lys Tyr Tyr Ala Lys Val Thr Val Thr Gly Gly Thr
225                 230                 235                 240

Gly Lys Asp Gly Tyr Tyr Glu Val Ser Val Asp Lys Thr Asn Gly Glu
                245                 250                 255

Val Thr Leu Ala Gly Gly Ala Thr Ser Pro Leu Thr Gly Gly Leu Pro
            260                 265                 270

Ala Thr Ala Thr Glu Asp Val Lys Asn Val Gln Val Ala Asn Ala Asp
        275                 280                 285

Leu Thr Glu Ala Lys Ala Ala Leu Thr Ala Ala Gly Val Thr Gly Thr
290                 295                 300

Ala Ser Val Val Lys Met Ser Tyr Thr Asp Asn Asn Gly Lys Thr Ile
305                 310                 315                 320

Asp Gly Gly Leu Ala Val Lys Val Gly Asp Asp Tyr Tyr Ser Ala Thr
                325                 330                 335

Gln Asn Lys Asp Gly Ser Ile Ser Ile Asn Thr Thr Lys Tyr Thr Ala
            340                 345                 350

Asp Asp Gly Thr Ser Lys Thr Ala Leu Asn Lys Leu Gly Gly Ala Asp
        355                 360                 365

Gly Lys Thr Glu Val Val Ser Ile Gly Gly Lys Thr Tyr Ala Ala Ser
370                 375                 380

Lys Ala Glu Gly His Asn Phe Lys Ala Gln Pro Asp Leu Ala Glu Ala
385                 390                 395                 400

Ala Ala Thr Thr Thr Glu Asn Pro Leu Gln Lys Ile Asp Ala Ala Leu
                405                 410                 415

Ala Gln Val Asp Thr Leu Arg Ser Asp Leu Gly Ala Val Gln Asn Arg
            420                 425                 430

Phe Asn Ser Ala Ile Thr Asn Leu Gly Asn Thr Val Asn Asn Leu Thr
        435                 440                 445

Ser Ala Arg Ser Arg Ile Glu Asp Ser Asp Tyr Ala Thr Glu Val Ser
450                 455                 460

Asn Met Ser Arg Ala Gln Ile Leu Gln Gln Ala Gly Thr Ser Val Leu
465                 470                 475                 480

Ala Gln Ala Asn Gln Val Pro Gln Asn Val Leu Ser Leu Leu Arg
                485                 490                 495

<210> SEQ ID NO 2
<211> LENGTH: 1488
<212> TYPE: DNA
<213> ORGANISM: Salmonella typhimurium

```
<400> SEQUENCE: 2
atggcacaag tcattaatac aaacagcctg tcgctgttga cccagaataa cctgaacaaa      60
tcccagtccg ctctgggcac cgctatcgag cgtctgtctt ccggtctgcg tatcaacagc     120
gcgaaagacg atgcggcagg tcaggcgatt gctaaccgtt ttaccgcgaa catcaaaggt     180
ctgactcagg cttcccgtaa cgctaacgac ggtatctcca ttgcgcagac cactgaaggc     240
gcgctgaacg aaatcaacaa caacctgcag cgtgtgcgtg aactggcggt tcagtctgct     300
aacagcacca actcccagtc tgacctcgac tccatccagg ctgaaatcac ccagcgcctg     360
aacgaaatcg accgtgtatc cggccagact cagttcaacg cgtgaaagt cctggcgcag     420 gacaacaccc tgaccatcca ggttggtgcc aacgacggtg aaactatcga tatcgatctg     480
aagcagatca actctcagac cctgggtctg gatacgctga atgtgcaaca aaaatataag     540
gtcagcgata cggctgcaac tgttacagga tatgccgata ctacgattgc tttagacaat     600
agtactttta aagcctcggc tactggtctt ggtggtactg accagaaaat tgatggcgat     660
ttaaaatttg atgatacgac tggaaaatat tacgccaaag ttaccgttac gggggggaact    720 ggtaaagatg gctattatga gtttccgtt gataagacga acggtgaggt gactcttgct      780
ggcggtgcga cttccccgct tacaggtgga ctacctgcga cagcaactga ggatgtgaaa     840
aatgtacaag ttgcaaatgc tgatttgaca gaggctaaag ccgcattgac agcagcaggt    900
gttaccggca cagcatctgt tgttaagatg tcttatactg ataataacgg taaaactatt     960
gatggtggtt tagcagttaa ggtaggcgat gattactatt ctgcaactca aaataaagat    1020
ggttccataa gtattaatac tacgaaatac actgcagatg acggtacatc caaaactgca    1080
ctaaacaaac tgggtggcgc agacggcaaa accgaagttg tttctattgg tggtaaaact    1140
tacgctgcaa gtaaagccga aggtcacaac tttaaagcac agcctgatct ggcggaagcg    1200
gctgctacaa ccaccgaaaa cccgctgcag aaaattgatg ctgctttggc acaggttgac    1260
acgttacgtt ctgacctggg tgcggtacag aaccgtttca actccgctat taccaacctg    1320
ggcaacaccg taaacaacct gacttctgcc cgtagccgta tcgaagattc cgactacgcg    1380
accgaagttt ccaacatgtc tcgcgcgcag attctgcagc aggccggtac ctccgttctg    1440
gcgcaggcga accaggttcc gcaaaacgtc ctctctttac tgcgttaa                  1488

<210> SEQ ID NO 3
<211> LENGTH: 8
<212> TYPE: PRT
<213> ORGANISM: Artificial
<220> FEATURE:
<223> OTHER INFORMATION: Peptide

<400> SEQUENCE: 3

Thr Ser Tyr Lys Phe Glu Ser Val
1               5

<210> SEQ ID NO 4
<211> LENGTH: 8
<212> TYPE: PRT
<213> ORGANISM: Artificial
<220> FEATURE:
<223> OTHER INFORMATION: Peptide

<400> SEQUENCE: 4

Ser Ile Ile Asn Phe Glu Lys Leu
1               5
```

METHODS AND COMPOSITIONS FOR INTRA-NASAL IMMUNIZATION WITH RECOMBINANT MVA ENCODING FLAGELLIN

This application is a National Phase application under 35 U.S.C. § 371 of International Application No. PCT/EP2015/072076, filed Sep. 25, 2015, and claims the benefit under 35 U.S.C. § 365 of European Application No. 14186588.1, filed Sep. 26, 2014, the disclosures of which are incorporated by reference herein in their entirety.

FIELD OF THE INVENTION

The present invention relates to immunogenic compositions comprising a recombinant modified vaccinia virus Ankara (MVA) comprising a nucleic acid sequence encoding flagellin and a nucleic acid sequence encoding a heterologous disease-associated antigen, wherein the immunogenic composition induces increased T-cell and antibody mediated immune responses specific for the heterologous disease-associated antigen when administered to a subject, e.g. a human subject, and to related methods and uses, especially when administered via the mucosal route, e.g. intra nasal.

BACKGROUND OF THE INVENTION

Mucosal surfaces are the main site of entry of pathogens, and some of the most dangerous pathogens enter their host and initiate the infection at such sites. Thus, the upper-respiratory, gastro-intestinal or urogenital-tracts remain the prime target of pathogens. Targeting an infection at the initiation site, which would contain and prevent mucosal invasion of the pathogen, neutralize the pathogen-derived toxin and inhibit the replication of the pathogen within the body at later infections stages, is undeniably the most important feature of mucosal vaccines (Holmgren, J., and C. Czerkinsky. 2005. Mucosal immunity and vaccines. *Nat. Med* 11:S45-S53). Therefore, mucosal immunization and the development of mucosal vaccines remains the Holy Grail for all vaccinologists. Furthermore, there are additional advantages of using mucosal vaccines which are multiple and obvious. Cheaper costs, needle-free delivery, safety, ease of administration, especially in case of mass immunization during pandemics, or lack of trained personnel, make mucosal vaccines very attractive compared to the traditional injectable vaccines. In addition, mucosal vaccination has the capacity to induce protective immunity in both the systemic and mucosal compartments, which classical parenteral vaccination fails to do, therefore providing dual protection (Fujkuyama, Y., D. Tokuhara, K. Kataoka, R. S. Gilbert, J. R. McGhee, Y. Yuki, H. Kiyono, and K. Fujihashi. 2012. Novel vaccine development strategies for inducing mucosal immunity. *Expert. Rev. Vaccines.* 11:367). It is also well established that the entire mucosal immune system is immunologically connected, and there is a notion of a "common mucosal immune system" (Brandtzaeg, P. 2007. Induction of secretory immunity and memory at mucosal surfaces. *Vaccine* 25:5467). Hence it is possible to immunize at one mucosal site whilst inducing immunity at another very distant mucosal site. The best example illustrating this approach remains vaccination via the intra-nasal (i.n.) route, which can elicit protective immunity in the urogenital tract in models of HSV (Gallichan, W. S., and K. L. Rosenthal. 1998. Long-term immunity and protection against herpes simplex virus type 2 in the murine female genital tract after mucosal but not systemic immunization. *J Infect Dis* 177:1155), and HIV infections (Gherardi, M. M., E. Perez-Jimenez, J. L. Najera, and M. Esteban. 2004. Induction of HIV immunity in the genital tract after intranasal delivery of a MVA vector: enhanced immunogenicity after DNA prime-modified vaccinia virus Ankara boost immunization schedule. *J Immunol.* 172:6209).

Nevertheless, despite all these advantages of mucosal vaccines, very few have made it to the market, compared to the parenteral vaccines. Those that have made it to the market for humans, are based on live-attenuated or heat-killed whole-cell vaccines, which include the oral cholera vaccine, the oral polio vaccine, the oral typhoid vaccine, the rotavirus vaccine for infants, the nasal-spray influenza vaccine. Due to some complications and adverse side-effects, some of them had to be withdrawn from the market, such as the seasonal 2001-H1N1 influenza vaccine, which induced facial paralysis in some patients in Switzerland (Mutsch, M., W. Zhou, P. Rhodes, M. Bopp, R. T. Chen, T. Linder, C. Spyr, and R. Steffen. 2004. Use of the inactivated intranasal influenza vaccine and the risk of Bell's palsy in Switzerland. *N. Engl. J Med* 350:896). Therefore, there are also concerns and safety measures, which need to be taken into consideration when developing a mucosal vaccine. Another important aspect of mucosal vaccines, is that they remain less immunogenic, compared to their traditional counterparts. Therefore the need for adjuvants is given, if one wants to break the tolerogenic environment, in the case of oral immunization, and induce more potent protective and long-lasting immune responses. In recent years, new research advances have been made in the mucosal immunology field and there is now a better understanding of the immunological mechanisms occurring at the mucosal surfaces. Even though there is still a long way to go, this intensive research has been a great step on the way for finding the best mucosal adjuvants and delivery systems, tailored for each pathogen.

The use of adjuvant is essential in vaccine research, especially when using recombinant sub-unit vaccines which remain less immunogenic compared to their heat-killed or live-attenuated counterparts. Indeed, it is believed that live-attenuated or inactivated pathogen-based vaccines inherently contain adjuvants. For the last 80 years, the only licensed adjuvant used in humans has been Alum (Aluminium salts) and oil-in-water emulsions. Recently two other adjuvants were licensed and can now be used, namely AS04 from GSK (a monophosphory lipid A preparation with aluminium salts) and MF59 (an oil-in-water preparation) used in combination with the seasonal influenza vaccine from Novartis. The disadvantage of oil-in-water emulsions and aluminium salt is that they do not elicit strong mucosal T helper cell responses. Studies have shown that the most promising mucosal adjuvants are bacterial toxin derivatives, Toll-like receptor (TLR) ligands, and novel small molecules (Rhee, J. H., S. E. Lee, and S. Y. Kim. 2012. Mucosal vaccine adjuvants update. *Clin Exp. Vaccine Res.* 1:50). The function of adjuvants is to boost the innate arm of the immune system, as they act mainly on antigen-presenting cells (APCs), such as dendritic cells (DCs), which in turn improve T and B cell responses to antigens (Schijns, V. E. 2001. Induction and direction of immune responses by vaccine adjuvants. *Crit Rev. Immunol.* 21:75). Pathogen associated molecular patterns (PAMPs), recognised by pattern recognition receptors (PRRs), are very potent adjuvants which strongly stimulate innate immune cells. PRRs are expressed on the cell surface or within intracellular compartments. Members of the PRR family include TLRs, nucleotide-binding domain (NOD)-like receptors (NLRs), retinoic acid-inducible gene (RIG)-like receptors (RLRs), and C-type lectins (Akira, S. 2011. Innate immunity and adjuvants. *Philos. Trans R. Soc Lond B Biol. Sci* 366:2748). Therefore, the use of TLR-based adjuvants, including bacterial cell wall lipopeptides (TLR4, TLR2) (Duthie, M. S., H. P. Windish, C. B. Fox, and S. G. Reed. 2011. Use of defined TLR ligands as adjuvants within human vaccines. *Immunol. Rev.* 239:178), and CpG motifs of bacterial DNA (TLR9) (Bode, C., G. Zhao, F. Steinhagen, T. Kinjo, and D. M. Klinman. 2011. CpG DNA as a vaccine adjuvant. *Expert. Rev. Vaccines.* 10:499) have been the adjuvants of choice to be incorporated in the new generation vaccines.

As mentioned previously, adjuvants are becoming an essential part for the development of mucosal vaccines. The TLR5 ligand flagellin, the major structural protein of Gram-negative flagella involved in the motility of bacteria, has elicited a lot of interest, and studies going back nearly a decade have been described using flagellin as a potent adjuvant, in the context of a broad range of recombinant vaccines (Mizel, S. B., and J. Bates. 2014. Flagellin as an adjuvant: cellular mechanisms and potential, pp. 5677). Flagellin has been used separately with the antigen or commonly administered as fusion proteins, which have proven to be very effective vaccines in animal models of influenza (Wang, B. Z., R. Xu, F. S. Quan, S. M. Kang, L. Wang, and R. W. Compans. 2010. Intranasal immunization with influenza VLPs incorporating membrane-anchored flagellin induces strong heterosubtypic protection. *PLoS. One.* 5:e13972), *Yersinia Pestis* (Honko, A. N., N. Sriranganathan, C. J. Lees, and S. B. Mizel. 2006. Flagellin is an effective adjuvant for immunization against lethal respiratory challenge with *Yersinia pestis*. *Infect Immun.* 74:1113), West nile virus (McDonald, W. F., J. W. Huleatt, H. G. Foellmer, D. Hewitt, J. Tang, P. Desai, A. Price, A. Jacobs, V. N. Takahashi, Y. Huang, V. Nakaar, L. Alexopoulou, E. Fikrig, and T. J. Powell. 2007. A West Nile virus recombinant protein vaccine that coactivates innate and adaptive immunity. *J Infect Dis* 195:1607), *Pseudomonas aeruginosa* (Weimer, E. T., H. Lu, N. D. Kock, D. J. Wozniak, and S. B. Mizel. 2009. A fusion protein vaccine containing OprF epitope 8, OprI, and type A and B flagellins promotes enhanced clearance of nonmucoid *Pseudomonas aeruginosa*. *Infect Immun.* 77:2356), *Plasmodium falciparum* (Carapau, D., R. Mitchell, A. Nacer, A. Shaw, C. Othoro, U. Frevert, and E. Nardin. 2013. Protective humoral immunity elicited by a needle-free malaria vaccine comprised of a chimeric *Plasmodium falciparum* circumsporozoite protein and a Toll-like receptor 5 agonist, flagellin. *Infect Immun.* 81:4350) and Vaccinia virus (Delaney, K. N., J. P. Phipps, J. B. Johnson, and S. B. Mizel. 2010. A recombinant flagellin-poxvirus fusion protein vaccine elicits complement-dependent protection against respiratory challenge with vaccinia virus in mice. *Viral Immunol.* 23:201). The effect of flagellin occurs on various APCs, DCs, neutrophils, monocytes, and more specifically on airway structural epithelial cells (Van, M. L., D. Fougeron, L. Janot, A. Didierlaurent, D. Cayet, J. Tabareau, M. Rumbo, S. Corvo-Chamaillard, S. Boulenouar, S. Jeffs, W. L. Vande, M. Lamkanfi, Y. Lemoine, F. Erard, D. Hot, T. Hussell, B. Ryffel, A. G. Benecke, and J. C. Sirard. 2014. Airway structural cells regulate TLR5-mediated mucosal adjuvant activity. *Mucosal. Immunol.* 7:489) and enterocytes (Van, M. L., D. Fougeron, L. Janot, A. Didierlaurent, D. Cayet, J. Tabareau, M. Rumbo, S. Corvo-Chamaillard, S. Jeffs, W. L. Vande, M. Lamkanfi, Y. Lemoine, F. Erard, D. Hot, T. Hussell, B. Ryffel, A. G. Benecke, and J. C. Sirard. 2014. Airway structural cells regulate TLR5-mediated mucosal adjuvant activity. *Mucosal. Immunol.* 7:489 and Gewirtz, A. T., T. A. Navas, S. Lyons, P. J. Godowski, and J. L. Madara. 2001. Cutting edge: bacterial flagellin activates basolaterally expressed TLR5 to induce epithelial proinflammatory gene expression. *J Immunol.* 167:1882). The latter have been shown to produce chemokines following TLR recognition, which in turn recruit more APCs to the site of immunization. The binding of flagellin to TLR5 initiates an immune cascade leading to production of the pro-inflammatory cytokines, IL-6 and TNF-α (Raoust, E., V. Balloy, I. Garcia-Verdugo, L. Touqui, R. Ramphal, and M. Chignard. 2009. *Pseudomonas aeruginosa* LPS or flagellin are sufficient to activate TLR-dependent signaling in murine alveolar macrophages and airway epithelial cells. *PLoS. One.* 4:e7259). In addition, another recognition pathway used by flagellin involves the Nlrc-4-inflammosome pathway (Miao, E. A., and S. E. Warren. 2010. Innate immune detection of bacterial virulence factors via the NLRC4 inflammasome. *J Clin Immunol.* 30:502), a member of the intracellular (NLR) family, which in this case leads to the production of IL-1β and IL-18 (Kupz, A., G. Guarda, T. Gebhardt, L. E. Sander, K. R. Short, D. A. Diavatopoulos, O. L. Wijburg, H. Cao, J. C. Waithman, W. Chen, D. Fernandez-Ruiz, P. G. Whitney, W. R. Heath, R. Curtiss, III, J. Tschopp, R. A. Strugnell, and S. Bedoui. 2012. NLRC4 inflammasomes in dendritic cells regulate noncognate effector function by memory CD8(+) T cells. *Nat. Immunol.* 13:162). In terms of adaptive immunity, it is well recognized that flagellin induces the proliferation of antigen-specific CD4$^+$ T cells (Bates, J. T., S. Uematsu, S. Akira, and S. B. Mizel. 2009. Direct stimulation of tlr5+/+ CD11c+ cells is necessary for the adjuvant activity of flagellin. *J Immunol.* 182:7539), together with robust antibody responses, characterized with high IgG1 and IgG2 titers (Huleatt, J. W., A. R. Jacobs, J. Tang, P. Desai, E. B. Kopp, Y. Huang, L. Song, V. Nakaar, and T. J. Powell. 2007. Vaccination with recombinant fusion proteins incorporating Toll-like receptor ligands induces rapid cellular and humoral immunity. *Vaccine* 25:763). It is believed that the adjuvant effect of flagellin on adaptive immunity is enhanced when administered as flagellin-antigen fusion proteins.

Among the many possible vaccine modalities, live vector viruses seem best to fulfill the requirement for inducing both T-cell and B-cell responses (R. A. Koup and D. C. Douek, "Vaccine Design for CD8$^+$ T Lymphocyte Responses," *Cold Spring Harb. Perspect. Med.* 2011; 1:a007252). While some live virus vaccines, such as vaccinia virus and yellow fever virus are effective but have unfavorable safety profiles, others, such as adenovirus, face problems due to pre-existing immunity (A. R. Thorner, et al., "Age Dependence of Adenovirus-Specific Neutralizing Antibody Titers in Individuals from Sub-Saharan Africa," *J. Clin. Microbiol.* 44(10):3781-3783 (2006)). A safe live vector vaccine unaffected by preexisting immunity is modified vaccinia virus Ankara (MVA), originally created by Anton Mayr and further developed into a third-generation smallpox vaccine (MVA-BN®) (Kennedy J S, Greenberg R N IMVAMUNE: modified vaccinia Ankara strain as an attenuated smallpox vaccine. Expert Rev Vaccines. 2009 January; 8(1):13-24. doi: 10.1586/14760584.8.1.13. Review).

The excellent safety profile of MVA, because of its replication deficiency in human cells, has been proven in many clinical trials, including vaccination of immune-compromised individuals, and during the smallpox eradication campaign in the 1970s, when 120,000 people were vaccinated with MVA (A. Mayr et al., "The smallpox vaccination strain MVA: marker, genetic structure, experience gained with the parenteral vaccination and behavior in organisms with a debilitated defense mechanism," *Zentralbl. Bakteriol. B* 167(5-6):375-390 (1978)). Since then, many different recombinant MVA vaccines have been generated and tested for the ability to immunize animals and humans against infectious (e.g., HIV, malaria) and non-infectious (e.g., prostate cancer) diseases. Its proven safety and good immunogenicity thus make MVA a prime candidate for a T- and B-cell-inducing vaccine vector.

Most studies using recombinant MVA have been described after systemic application. Nevertheless, a few reports have examined the immune response after mucosal administration of MVA, especially i.n. delivery in studies of Influenza (Sutter, G., L. S. Wyatt, P. L. Foley, J. R. Bennink, and B. Moss. 1994. A recombinant vector derived from the host range-restricted and highly attenuated MVA strain of vaccinia virus stimulates protective immunity in mice to influenza virus. *Vaccine* 12:1032.), RSV (Wyatt, L. S., S. T. Shors, B. R. Murphy, and B. Moss. 1996. Development of a replication-deficient recombinant vaccinia virus vaccine effective against parainfluenza virus 3 infection in an animal model. *Vaccine* 14:1451) and HIV (Gherardi, M. M., E. Perez-Jimenez, J. L. Najera, and M. Esteban. 2004. Induction of HIV immunity in the genital tract after intranasal delivery of a MVA vector: enhanced immunogenicity after DNA prime-modified vaccinia virus Ankara boost immunization schedule. *J Immunol.* 172:6209). One study describing the role of a flagellin-poxvirus vaccine, in this case using recombinant vaccinia virus antigen proteins, L1R and B5R, fused to flagellin, demonstrated a protective effect in mice immunized with this flagellin-fusion protein against a vaccinia virus challenge (Delaney, K. N., J. P. Phipps, J. B. Johnson, and S. B. Mizel. 2010. A recombinant flagellin-poxvirus fusion protein vaccine elicits complement-dependent protection against respiratory challenge with vaccinia virus in mice. *Viral Immunol.* 23:201). Furthermore, the use of flagellin delivered via the i.n. route, has been used in a number of studies in various mouse models and in non-human primates at a very low dose (Weimer, E. T., S. E. Ervin, D. J. Wozniak, and S. B. Mizel. 2009. Immunization of young African green monkeys with OprF epitope 8-OprI-type A- and B-flagellin fusion proteins promotes the production of protective antibodies against nonmucoid *Pseudomonas aeruginosa. Vaccine* 27:6762), making it a very attractive mucosal adjuvant candidate that could be used in human vaccines. To date, there are no reports using rMVA together with flagellin, particularly genetically encoded within the vector, and administered via the i.n. route

BRIEF SUMMARY OF THE INVENTION

The present inventors have generated a recombinant MVA-BN expressing flagellin and have shown that i.n. immunization with MVA-BN-flagellin elicits enhanced cellular and humoral immune responses, both systemically and at mucosal sites, compared to non-adjuvanted recombinant MVA. The present inventors have also shown that i.n. immunization with recombinant MVA-flagellin could elicit gastro-intestinal immune responses. Thus, recombinant MVA-flagellin is a prime candidate vector for the development of prophylactic and therapeutic vaccines, i.e. the development of mucosal vaccine against a broader range of diseases including gastro-intestinal pathogens.

In one aspect, provided herein are immunogenic compositions comprising a recombinant modified vaccinia virus Ankara (MVA) comprising a nucleic acid sequence encoding a flagellin and a nucleic acid sequence encoding a heterologous disease-associated antigen, wherein the immunogenic composition induces increased T-cell and/or B-cell immune responses specific for the heterologous disease-associated antigen when administered to a subject as compared to T-cell and/or B-cell immune responses specific for the heterologous disease-associated antigen induced by administration of a recombinant MVA comprising a nucleic acid sequence encoding a heterologous disease-associated antigen but not a nucleic acid sequence encoding a flagellin. In certain embodiments, the increased T-cell immune response comprises greater numbers of cytotoxic T-cells (CTLs) specific for the heterologous disease-associated antigen. In certain embodiments, the greater numbers of CTLs specific for the heterologous disease-associated antigen also display increased cytolytic activity compared to CTLs induced by administration of a recombinant MVA comprising a nucleic acid sequence encoding a heterologous disease-associated antigen but not a nucleic acid sequence encoding a flagellin. In certain embodiments, the increased T-cell immune response comprises greater numbers of memory T-cells specific for the heterologous disease-associated antigen. In certain embodiments, the increased T-cell immune response comprises greater numbers of CTLs specific for the heterologous disease-associated antigen and greater numbers of memory T-cells specific for the heterologous disease-associated antigen. In certain embodiments, the greater numbers of CTLs specific for the heterologous disease-associated antigen also display increased cytolytic activity compared to CTLs induced by administration of a recombinant MVA comprising a nucleic acid sequence encoding a heterologous disease-associated antigen but not a nucleic acid sequence encoding a flagellin.

In certain embodiments, the nucleic acid sequence encodes a flagellin having at least 95%, 96%, 97%, 98%, 99%, or 100% amino acid sequence identity to SEQ ID NO:1. In certain embodiments, the nucleic acid sequence encodes a flagellin having the amino acid sequence of SEQ ID NO:1. In certain embodiments, the immunogenic composition further comprises a pharmaceutically acceptable carrier.

In certain embodiments, the disease-associated antigen is an infectious disease antigen or a tumor-associated antigen. In certain embodiments, the disease-associated antigen is an infectious disease antigen. In certain embodiments, the infectious disease antigen is a viral antigen, a bacterial antigen, a fungal antigen, or a parasite antigen.

In certain embodiments, the infectious disease antigen is a viral antigen. In certain embodiments, the viral antigen is derived from a virus selected from the group consisting of adenovirus, Arbovirus, Astrovirus, Coronavirus, Coxsackievirus, Crimean-Congo hemorrhagic fever virus, cytomegalovirus ("CMV"), dengue virus, Ebola virus, Epstein-Barr virus ("EBV"), Foot-and-mouth disease virus, Guanarito virus, Hendra virus, herpes simplex virus-type 1 ("HSV-1"), herpes simplex virus-type 2 ("HSV-2"), human herpesvirus-type 6 ("HHV-6"), human herpesvirus-type 8 ("HHV-8"), hepatitis A virus ("HAV"), hepatitis B virus ("HBV"), hepatitis C virus ("HCV"), hepatitis D virus ("HDV"), hepatitis E virus ("HEV"), human immunodeficiency virus ("HIV"), influenza virus, Japanese encephalitis virus, Junin virus, Lassa virus, Machupo virus, Marburg virus, measles virus, human metapneumovirus, Molluscum contagiosum virus, mumps virus, Newcastle disease virus, Nipha virus, Norovirus, Norwalk virus, human papillomavirus ("HPV"), parainfluenza virus, parvovirus, poliovirus, rabies virus, respiratory syncytial virus ("RSV"), rhinovirus, rotavirus, rubella virus, Sabia virus, severe acute respiratory syndrome virus ("SARS"), varicella zoster virus, variola virus, West Nile virus, and yellow fever virus.

In certain embodiments, the infectious disease antigen is a bacterial antigen. In certain embodiments, the bacterial antigen is derived from a bacterium selected from the group consisting of *Bacillus anthracis, Bordetella pertussis, Borrelia burgdorferi, Brucella abortus, Brucella canis, Brucella melitensis, Brucella suis, Burkholderia mallei, Burkholderia pseudomallei, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diptheriae, Enterococcus faecalis, Enterococcus faecium, Escherichia coli, enterotoxigenic Escherichia coli, enteropathogenic Escherichia coli, Escherichia coli*) 157:H7, *Francisella tularensis, Haemophilus influenza, Helicobacter pylon, Legionella pneumophila, Leptospira interrogans, Listeria monocytogenes, Mycobacterium leprae, Mycobacterium tuberculosis, Mycoplasma pneumoniae, Neisseria gonorrhoeae, Neisseria meningitides, Pseudomonas aeruginosa, Rickettsia rickettsia, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholerae*, and *Yersinia pestis*.

In certain embodiments, the infectious disease antigen is a fungal antigen. In certain embodiments, the fungal antigen is derived from a fungus selected from the group consisting of *Aspergillus clavatus, Aspergillus flavus, Aspergillus fumigatus, Aspergillus nidulans, Aspergillus niger, Aspergillus terreus, Blastomyces dermatitidis, Candida albicans, Candida dubliniensis, Candida glabrata, Candida parapsilosis, Candida rugosa, Candida tropicalis, Cryptococcus albidus, Cryptococcus gattii, Cryptococcus laurentii, Cryptococcus neoformans, Histoplasma capsulatum, Microsporum canis, Pneumocystis carinii, Pneumocystis jirovecii, Sporothrix schenckii, Stachbotrys chartarum, Tinea barbae, Tinea captitis, Tinea corporis, Tinea cruris, Tinea faciei, Tinea incognito, Tinea nigra, Tinea versicolor, Trichophyton rubrum* and *Trichophyton tonsurans*.

In certain embodiments, the infectious disease antigen is a parasite antigen. In certain embodiments, the parasite antigen is derived from a parasite selected from the group consisting of *Anisakis* spp. *Babesia* spp., *Baylisascaris procyonis, Cryptosporidium* spp., *Cyclospora cayetanensis, Diphyllobothrium* spp., *Dracunculus medinensis, Entamoeba histolytica, Giardia duodenalis, Giardia intestinalis, Giardia lamblia, Leishmania* sp., *Plasmodium falciparum, Schistosoma mansoni, Schistosoma haematobium, Schistosoma japonicum, Taenia* spp., *Toxoplasma gondii, Trichinella spiralis*, and *Trypanosoma cruzi*.

In certain embodiments, the disease-associated antigen is a tumor-associated antigen. In certain embodiments, the tumor-associated antigen is selected from the group consisting of 5-α-reductase, α-fetoprotein ("AFP"), AM-1, APC, April, B melanoma antigen gene ("BAGE"), β-catenin, Bcl12, bcr-abl, Brachyury, CA-125, caspase-8 ("CASP-8", also known as "FLICE"), Cathepsins, CD19, CD20, CD21/complement receptor 2 ("CR2"), CD22/BL-CAM, CD23/$F_c\varepsilon RII$, CD33, CD35/complement receptor 1 ("CR1"), CD44/PGP-1, CD45/leucocyte common antigen ("LCA"), CD46/membrane cofactor protein ("MCP"), CD52/CAMPATH-1, CD55/decay accelerating factor ("DAF"), CD59/protectin, CDC27, CDK4, carcinoembryonic antigen ("CEA"), c-myc, cyclooxygenase-2 ("cox-2"), deleted in colorectal cancer gene ("DCC"), DcR3, E6/E7, CGFR, EMBP, Dna78, farnesyl transferase, fibroblast growth factor-8a ("FGF8a"), fibroblast growth factor-8b ("FGF8b"), FLK-1/KDR, folic acid receptor, G250, G melanoma antigen gene family ("GAGE-family"), gastrin 17, gastrin-releasing hormone, ganglioside 2 ("GD2")/ganglioside 3 ("GD3")/ganglioside-monosialic acid-2 ("GM2"), gonadotropin releasing hormone ("GnRH"), UDP-GlcNAc:$R_1$Man (α1-6)$R_2$ [GlcNAc to Man(α1-6)] β1,6-N-acetylglucosaminyltransferase V ("GnT V"), GP1, gp100/Pme117, gp-100-in4, gp15, gp75/tyrosine-related protein-1 ("gp75/TRP-1"), human chorionic gonadotropin ("hCG"), heparanase, Her2/neu, human mammary tumor virus ("HMTV"), 70 kiloDalton heat-shock protein ("HSP70"), human telomerase reverse transcriptase ("hTERT"), insulin-like growth factor receptor-1 ("IGFR-1"), interleukin-13 receptor ("IL-13R"), inducible nitric oxide synthase ("iNOS"), Ki67, KIAA0205, K-ras, H-ras, N-ras, KSA, LKLR-FUT, melanoma antigen-encoding gene 1 ("MAGE-1"), melanoma antigen-encoding gene 2 ("MAGE-2"), melanoma antigen-encoding gene 3 ("MAGE-3"), melanoma antigen-encoding gene 4 ("MAGE-4"), mammaglobin, MAP17, Melan-A/melanoma antigen recognized by T-cells-1 ("MART-1"), mesothelin, MIC A/B, MT-MMPs, mucin, testes-specific antigen NY-ESO-1, osteonectin, p15, P170/MDR1, p53, p97/melanotransferrin, PAI-1, platelet-derived growth factor ("PDGF"), μPA, PRAME, probasin, progenipoietin, prostate-specific antigen ("PSA"), prostate-specific membrane antigen ("PSMA"), prostatic acid phosphatase ("PAP"), RAGE-1, Rb, RCAS1, SART-1, SSX-family, STAT3, STn, TAG-72, transforming growth factor-alpha ("TGF-α"), transforming growth factor-beta ("TGF-β"), Thymosin-beta-15, tumor necrosis factor-alpha ("TNF-α"), TP1, TRP-2, tyrosinase, vascular endothelial growth factor ("VEGF"), ZAG, p16INK4, and glutathione-S-transferase ("GST").

In another aspect, provided herein are methods of inducing an antigen-specific immune response to a disease-associated antigen, comprising administering any one of the immunogenic compositions provided herein to a subject in need thereof, wherein the immunogenic composition induces increased T-cell and/or B-cell immune responses specific for the heterologous disease-associated antigen when administered to a subject. In certain embodiments, the subject is a mammal. In certain embodiments, the mammal is a human. In certain embodiments, the increased T-cell immune response comprises greater numbers of cytotoxic T-cells (CTLs) specific for the heterologous disease-associated antigen. In certain embodiments, the greater numbers of CTLs specific for the heterologous disease-associated antigen also display increased cytolytic activity compared to CTLs induced by administration of a recombinant MVA comprising a nucleic acid sequence encoding a heterologous disease-associated antigen but not a nucleic acid sequence encoding a flagellin. In certain embodiments, the increased T-cell immune response comprises greater numbers of memory T-cells specific for the heterologous disease-associated antigen. In certain embodiments, the increased T-cell immune response comprises greater numbers of CTLs specific for the heterologous disease-associated antigen and greater numbers of memory T-cells specific for the heterologous disease-associated antigen. In certain embodiments, the greater numbers of CTLs specific for the heterologous disease-associated antigen also display increased cytolytic activity compared to CTLs induced by administration of a recombinant MVA comprising a nucleic acid sequence encoding a heterologous disease-associated antigen but not a nucleic acid sequence encoding a flagellin.

In certain embodiments, the nucleic acid sequence encodes a flagellin having at least 95%, 96%, 97%, 98%, 99%, or 100% amino acid sequence identity to SEQ ID NO:1. In certain embodiments, the nucleic acid sequence encodes a flagellin having the amino acid sequence of SEQ ID NO:1. In certain embodiments, the immunogenic composition further comprises a pharmaceutically acceptable carrier.

In certain embodiments, the disease-associated antigen is an infectious disease antigen or a tumor-associated antigen. In certain embodiments, the disease-associated antigen is an infectious disease antigen. In certain embodiments, the infectious disease antigen is a viral antigen, a bacterial antigen, a fungal antigen, or a parasite antigen.

In certain embodiments, the infectious disease antigen is a viral antigen. In certain embodiments, the viral antigen is derived from a virus selected from the group consisting of adenovirus, Arbovirus, Astrovirus, Coronavirus, Coxsackievirus, Crimean-Congo hemorrhagic fever virus, cytomegalovirus ("CMV"), dengue virus, Ebola virus, Epstein-Barr virus ("EBV"), Foot-and-mouth disease virus, Guanarito virus, Hendra virus, herpes simplex virus-type 1 ("HSV-1"), herpes simplex virus-type 2 ("HSV-2"), human herpesvirus-type 6 ("HHV-6"), human herpesvirus-type 8 ("HHV-8"), hepatitis A virus ("HAV"), hepatitis B virus ("HBV"), hepatitis C virus ("HCV"), hepatitis D virus ("HDV"), hepatitis E virus ("HEV"), human immunodeficiency virus ("HIV"), influenza virus, Japanese encephalitis virus, Junin virus, Lassa virus, Machupo virus, Marburg virus, measles virus, human metapneumovirus, Molluscum contagiosum virus, mumps virus, Newcastle disease virus, Nipha virus, Norovirus, Norwalk virus, human papillomavirus ("HPV"), parainfluenza virus, parvovirus, poliovirus, rabies virus, respiratory syncytial virus ("RSV"), rhinovirus, rotavirus, rubella virus, Sabia virus, severe acute respiratory syndrome virus ("SARS"), varicella zoster virus, variola virus, West Nile virus, and yellow fever virus.

In certain embodiments, the infectious disease antigen is a bacterial antigen. In certain embodiments, the bacterial antigen is derived from a bacterium selected from the group consisting of *Bacillus anthracis, Bordetella pertussis, Borrelia burgdorferi, Brucella abortus, Brucella canis, Brucella melitensis, Brucella suis, Burkholderia mallei, Burkholderia pseudomallei, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diptheriae, Enterococcus faecalis, Enterococcus faecium, Escherichia coli,* enterotoxigenic *Escherichia coli,* enteropathogenic *Escherichia coli, Escherichia coli*) 157:H7, *Francisella tularensis, Haemophilus influenza, Helicobacter pylon, Legionella pneumophila, Leptospira interrogans, Listeria monocytogenes, Mycobacterium leprae, Mycobacterium tuberculosis, Mycoplasma pneumoniae, Neisseria gonorrhoeae, Neisseria meningitides, Pseudomonas aeruginosa, Rickettsia rickettsia, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholerae,* and *Yersinia pestis.*

In certain embodiments, the infectious disease antigen is a fungal antigen. In certain embodiments, the fungal antigen is derived from a fungus selected from the group consisting of *Aspergillus clavatus, Aspergillus flavus, Aspergillus fumigatus, Aspergillus nidulans, Aspergillus niger, Aspergillus terreus, Blastomyces dermatitidis, Candida albicans, Candida dubliniensis, Candida glabrata, Candida parapsilosis, Candida rugosa, Candida tropicalis, Cryptococcus albidus, Cryptococcus gattii, Cryptococcus laurentii, Cryptococcus neoformans, Histoplasma capsulatum, Microsporum canis, Pneumocystis carinii, Pneumocystis jirovecii, Sporothrix schenckii, Stachbotrys chartarum, Tinea barbae, Tinea captitis, Tinea corporis, Tinea cruris, Tinea faciei, Tinea incognito, Tinea nigra, Tinea versicolor, Trichophyton rubrum* and *Trichophyton tonsurans.*

In certain embodiments, the infectious disease antigen is a parasite antigen. In certain embodiments, the parasite antigen is derived from a parasite selected from the group consisting of *Anisakis* spp. *Babesia* spp., *Baylisascaris procyonis, Cryptosporidium* spp., *Cyclospora cayetanensis, Diphyllobothrium* spp., *Dracunculus medinensis, Entamoeba histolytica, Giardia duodenalis, Giardia intestinalis, Giardia lamblia, Leishmania* sp., *Plasmodium falciparum, Schistosoma mansoni, Schistosoma haematobium, Schistosoma japonicum, Taenia* spp., *Toxoplasma gondii, Trichinella spiralis,* and *Trypanosoma cruzi.*

In certain embodiments, the disease-associated antigen is a tumor-associated antigen. In certain embodiments, the tumor-associated antigen is selected from the group consisting of 5-α-reductase, α-fetoprotein ("AFP"), AM-1, APC, April, B melanoma antigen gene ("BAGE"), β-catenin, Bcl12, bcr-abl, Brachyury, CA-125, caspase-8 ("CASP-8", also known as "FLICE"), Cathepsins, CD19, CD20, CD21/complement receptor 2 ("CR2"), CD22/BL-CAM, CD23/F$_c$εRII, CD33, CD35/complement receptor 1 ("CR1"), CD44/PGP-1, CD45/leucocyte common antigen ("LCA"), CD46/membrane cofactor protein ("MCP"), CD52/CAMPATH-1, CD55/decay accelerating factor ("DAF"), CD59/protectin, CDC27, CDK4, carcinoembryonic antigen ("CEA"), c-myc, cyclooxygenase-2 ("cox-2"), deleted in colorectal cancer gene ("DCC"), DcR3, E6/E7, CGFR, EMBP, Dna78, farnesyl transferase, fibroblast growth factor-8a ("FGF8a"), fibroblast growth factor-8b ("FGF8b"), FLK-1/KDR, folic acid receptor, G250, G melanoma antigen gene family ("GAGE-family"), gastrin 17, gastrin-releasing hormone, ganglioside 2 ("GD2")/ganglioside 3 ("GD3")/ganglioside-monosialic acid-2 ("GM2"), gonadotropin releasing hormone ("GnRH"), UDP-GlcNAc:R$_1$Man (α1-6)R$_2$ [GlcNAc to Man(α1-6)] β1,6-N-acetylglucosaminyltransferase V ("GnT V"), GP1, gp100/Pme117, gp-100-in4, gp15, gp75/tyrosine-related protein-1 ("gp75/TRP-1"), human chorionic gonadotropin ("hCG"), heparanase, Her2/neu, human mammary tumor virus ("HMTV"), 70 kiloDalton heat-shock protein ("HSP70"), human telomerase reverse transcriptase ("hTERT"), insulin-like growth factor receptor-1 ("IGFR-1"), interleukin-13 receptor ("IL-13R"), inducible nitric oxide synthase ("iNOS"), Ki67, KIAA0205, K-ras, H-ras, N-ras, KSA, LKLR-FUT, melanoma antigen-encoding gene 1 ("MAGE-1"), melanoma antigen-encoding gene 2 ("MAGE-2"), melanoma antigen-encoding gene 3 ("MAGE-3"), melanoma antigen-encoding gene 4 ("MAGE-4"), mammaglobin, MAP17, Melan-A/melanoma antigen recognized by T-cells-1 ("MART-1"), mesothelin, MIC A/B, MT-MMPs, mucin, testes-specific antigen NY-ESO-1, osteonectin, p15, P170/MDR1, p53, p97/melanotransferrin, PAI-1, platelet-derived growth factor ("PDGF"), μPA, PRAME, probasin, progenipoietin, prostate-specific antigen ("PSA"), prostate-specific membrane antigen ("PSMA"), prostatic acid phosphatase ("PAP"), RAGE-1, Rb, RCAS1, SART-1, SSX-family, STAT3, STn, TAG-72, transforming growth factor-alpha ("TGF-α"), transforming growth factor-beta ("TGF-β"), Thymosin-beta-15, tumor necrosis factor-alpha ("TNF-α"), TP1, TRP-2, tyrosinase, vascular endothelial growth factor ("VEGF"), ZAG, p16INK4, and glutathione-S-transferase ("GST").

In another aspect, provided herein are kits comprising the immunogenic composition provided herein in a first vial or container for a first administration (priming) and in a second vial or container for a second administration (boosting).

In certain embodiments, the kit comprises the immunogenic composition provided herein in a third, fourth or further vial or container the immunogenic composition for a third, fourth or further administration (boosting).

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and do not restrict the scope of the invention as claimed.

The accompanying drawings, which are incorporated in and constitute a part of this specification, illustrate various embodiments of the invention and together with the description, serve to explain the principles of the invention.

BRIEF DESCRIPTION OF THE DRAWINGS

FIG. 1 shows enhanced CTL response after i.n. rMVA-flagellin immunization at systemic and mucosal sites. C57BL/6 mice were immunized intra-nasally with $3.5 \times 10^7$ $TCID_{50}$ of rMVA or rMVA-flagellin on day 0 and day 21. PBS administered intra-nasally was used as control. Spleen frequency of OVA-(a) and B8-(e) specific CD8 T cells was determined by MHC I dextramer staining on day 35 after immunization. Spleen absolute numbers of OVA (b)-specific CD8 T cells were determined. Lung frequency of OVA-(c) and B8-(f) specific CD8 T cell was also determined at day 35. Absolute numbers of OVA (d)-specific CD8 T cells/lung were also determined.

FIG. 2 shows blood CTL response. Blood was taken 7 days after the first immunization and 2 weeks after the boost, at day 28 for blood CD8 T cell analysis. Blood OVA-(a) and B8-(b) specific CTL response was determined. Results are shown as average (+/−SEM) with error bars representative of two independent experiments with 5 mice per group.

FIG. 3 shows enhanced frequency of cytokine-producing CTLs in the speen after i.n. rMVA-flagellin immunization. C57BL/6 mice were immunized intra-nasally with $3.5 \times 10^7$ $TCID_{50}$ of rMVA or rMVA-flagellin on day 0 and day 21. PBS administered intra-nasally was used as control. At day 35, spleens were taken and the frequency of OVA-(a, c) and B8-specific (b, d,) cytokine-producing CTL was determined. IFN-γ (a,b) and TNF-α (c,d) production was analysed by intracellular cytokine staining after standard 6 hrs in vitro restimulation with $B8_{20-27}$ and $OVA_{257-264}$ peptides. Data is representative of two independent experiments with 5 mice per group.

FIG. 4 shows enhanced quality of the CD8 T cell response after i.n. rMVA-flagellin immunization in the spleen. C57BL/6 mice were immunized intra-nasally with $3.5 \times 10^7$ $TCID_{50}$ of rMVA or rMVA-flagellin on day 0 and day 21. PBS administered intra-nasally was used as control. At day 35, spleens were taken and the frequency of OVA-specific CTL-producing cytokine was determined. Cytokine production was analysed by intracellular cytokine staining after standard 6 hrs in vitro restimulation with $OVA_{257-264}$ peptides. IFN-γ (a), and TNF-α (b) production was determined by GMFI (+/−SEM) gated on OVA-specific CD8 T cells. The relative frequency of OVA-specific CD8 T cells-expressing IFN-γ and TNF-α was determined. Results are shown as average (+/−SEM), representative of two independent experiments with 5 mice per group.

FIG. 5 shows i.n. rMVA-flagellin immunized mice exhibit increased serum antibody responses. C57BL/6 mice were immunized intra-nasally with $3.5 \times 10^7$ $TCID_{50}$ of rMVA or rMVA-flagellin on day 0 and day 21. PBS administered intra-nasally was used as control. Serum was taken on day 35. MVA and OVA-specific IgG (a), MVA-specific IgG1/IgG2c (b) and OVA-specific IgG1/IgG2c (c) levels were determined by ELISA. Results are shown as OD at 1/6400 serum dilution and represent mean (+/−SEM). Data is representative of two independent experiments with 5 mice per group.

FIG. 6 shows antibody responses in the BAL is enhanced in i.n. rMVA-flagellin-immunized mice. C57BL/6 mice were immunized intra-nasally with $3.5 \times 10^7$ $TCID_{50}$ of rMVA or rMVA-flagellin on day 0 and day 21. PBS administered intra-nasally was used as control. At day 35, BAL was collected and analysed for IgG (a), IgG1 (b), IgG2c (c) and IgA (d,e). MVA-specific and OVA-specific IgGs and IgA levels were measured by ELISA. Results are shown OD at 1/80 serum dilution and represent mean (+/−SEM), representative of two independent experiment with 5 mice per group.

FIG. 7 shows induction of gastro-intestinal immune response and homing of CD4 and CD8 T cells to the mLN. C57BL/6 mice were adoptively transferred i.v with $1 \times 10^4$ CD45.1+OT-I CD8 T and $1 \times 10^5$ CD45.1+OT-II CD4 T cells a day prior to i.n. immunization with $3.5 \times 10^7$ $TCID_{50}$ of rMVA or rMVA-flagellin. PBS administered intra-nasally was used as control. 7 days after i.n. immunization, the homing of transferred OT-I CD8 T and OT-II CD4 Tcells was determined in the mLN. The frequency of $CD45.1^+ CD8^+$ and $CD45.1^+CD4^+$ T cells was determined by flow cytometry in the mLN of PBS, rMVA and rMVA-flagellin-immunized mice. Frequency (a) and absolute numbers (b) of adoptively transferred $CD45.1^+CD8^+$ T cells migrated to the mLN were determined. (c) Frequency and (d) absolute numbers of adoptively transferred $CD45.1^+CD4^+$ T cells in the mLN. Results are shown as mean (+/−SEM), representative of two independent experiments with 3 mice per group.

FIG. 8 shows i.n. rMVA immunization induces intestinal IgA production. C57BL/6 mice were immunized intra-nasally with $3.5 \times 10^7$ $TCID_{50}$ of rMVA or rMVA-flagellin on day 0 and day 21. PBS administered intra-nasally was used as control. At day 35, small intestines were taken and intestinal washes were obtained from the distal part of the small intestine. OVA-specific IgA levels in the intestinal washes were measured by ELISA. Results are shown as OD at 1/10 serum dilution and represent mean (+/−SEM), representative of two independent experiment with 5 mice per group.

FIG. 9 shows inflammasome and TLR-5 dependent innate cytokine responses in the BAL of i.n. rMVA-flagellin-immunized mice. C57BL/6 mice were immunized intra-nasally with $3.5 \times 10^7$ $TCID_{50}$ of rMVA or rMVA-flagellin. The BAL was collected the following day and cytokine response was measure by Luminex analysis. IL-1β (a), IL-18 (b), TNF-α (c) and CXCL1 (d) protein levels were measured. C57BL/6 and $NLRC4^{-/-}$ (e, f) mice were immunized intra-nasally with $3.5 \times 10^7$ $TCID_{50}$ of rMVA or rMVA-flagellin and the BAL was collected the following day. The amounts of IL-1β (e) and IL-18 (f) protein levels were measured by luminex.

FIG. 10 shows Hek-blue hTLR5 activation with rMVA-flagellin. Hek-blue hTLR5 cells at a concentration of $4 \times 10^4$ cells/well were seeded and incubated for 2 hrs at 37'C. After 2 hrs the medium was removed and either cells lysates or supernatant from rMVA or rMVA-flagellin infected Hela cells were added for another 18 hrs. Recombinant flagellin was used as a positive control. The supernatant from the culture was collected and SEAP activity was measured for TLR5 activation.

FIG. 11 shows inflammasome and TLR-5-dependent innate sensing of rMVA-flagellin by FLDC. 8 days FLDC were generated and $5 \times 10^5$ DC/well were infected with 4 $TCID_{50}$/cell rMVA, rMVA-flagellin, rMVA and flagellin, flagellin and transfected flagellin. 6 hrs post-infection, the supernatant was collected and analysed for cytokine production. IL-1β (a), IL-18 (b), IL-6 (c) and TNF-α (d) protein levels were measured with Luminex.

FIG. 12 shows stimulation of mucosal DC by rMVA-flagellin. Mucosal DC subsets from 8 day FL-treated mice were sorted. The three subsets, gated on $CD11c^+MHC-II^+$ DC were separated according to CD172a and CD103 in order to obtain the three following subsets: $CD172a^-CD103^+$, $CD172a^-CD103^-$ and $CD17a^+CD103^+$. $1 \times 10^4$ DC/well were infected with 4 $TCID_{50}$/cell rMVA and rMVA-flagellin. Following 18 hrs incubation, the supernatant was collected and IL-1β production was measured with Luminex.

BRIEF DESCRIPTION OF THE SEQUENCES

SEQ ID NO:1 is the amino acid sequence of flagellin (*Salmonella typhimurium*).

SEQ ID NO:2 is the nucleic acid sequence of flagellin (*Salmonella typhimurium*).

SEQ ID NO:3 is the amino acid sequence of the MVA-derived peptide $B^820$-27.

SEQ ID NO:4 is the amino acid sequence of the ovalbumin-derived peptide $OVA_{257-264}$.

DETAILED DESCRIPTION OF THE INVENTION

Reference will now be made in detail to exemplary embodiments of the invention, examples of which are illustrated in the accompanying drawings. Wherever possible, the same reference numbers will be used throughout the drawings to refer to the same or like parts.

Definitions

Unless otherwise noted, technical terms herein are used according to conventional usage by one of ordinary skill in the art of molecular biology. For common terms in molecular biology, conventional usage may be found in standard textbooks such as, for example, *Genes V* by Benjamin Lewin, published by Oxford University Press, 1994 (ISBN 0-19-854287-9); Kendrew et al. (eds.); *The Encyclopedia of Molecular Biology*, published by Blackwell Science Ltd., 1994 (ISBN 0-632-02182-9); and *Molecular Biology and Biotechnology: a Comprehensive Desk Reference* edited by Robert A. Meyers, published by VCH Publishers, Inc., 1995 (ISBN 1-56081-569-8).

As used herein, the singular forms "a", "an", and "the" include plural references unless the context clearly indicates otherwise. Thus, for example, reference to "an epitope" includes reference to one or more epitopes and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize or be able to ascertain using no more than routine experimentation, many equivalents to the specific embodiments of the invention described herein. Such equivalents are encompassed by the present invention.

Throughout this specification and the claims which follow, unless the context requires otherwise, the word "comprise", and variations such as "comprises" and "comprising" mean "includes", and therefore include a stated integer or step or group of integers or steps and do exclude any other integer or step or group of integers or steps. When used herein the term "comprising" can be substituted with the term "containing", "including" or "having". Any of the aforementioned terms (comprising, containing, including, having), whenever used herein in the context of an aspect or embodiment of the present invention can be substituted with the term "consisting of".

When used herein, the term "consisting of" excludes any element, step, or ingredient not specified in the claim. When used herein, "consisting essentially of" excludes any materials or steps "which would affect the basic and novel characteristics" of the product or method defined in the rest of the claim. *Water Techs. Corp. v. Calco Ltd.*, 7 U.S.P.Q.2d 1097, 1102 (Fed. Cir. 1988).

As used herein, the conjunctive "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore to satisfy the requirement of the term "and/or" as used herein. Concurrent applicability of more than one of the options is also understood to fall within the meaning, and therefore satisfy the requirement of the term "and/or."

All publications, patent applications, patents, and other references mentioned herein are incorporated by reference in their entirety. In case of conflict, the present specification, including all definitions, will control.

Adjuvant: A vehicle used to enhance antigenicity. Adjuvants can include: (1) suspensions of minerals (alum, aluminum hydroxide, or phosphate) on which antigen is adsorbed; (2) water-in-oil emulsions in which an antigen solution is emulsified in mineral oil (Freund's incomplete adjuvant), sometimes with the inclusion of killed mycobacteria (Freund's complete adjuvant) to further enhance antigenicity by inhibiting degradation of antigen and/or causing an influx of macrophages; (3) immunstimulatory oligonucleotides such as, for example, those including a CpG motif can also be used as adjuvants (for example see U.S. Pat. Nos. 6,194,388; and 6,207,646); and (4) purified or recombinant proteins such as costimulatory molecules. Exemplary adjuvants include, but are not limited to, B7-1, ICAM-1, LFA-3, and GM-CSF.

Antigen; antigenic determinant; epitope: A compound, composition, or substance that can stimulate the production of antibodies or a $CD4^+$ or $CD8^+$ T-cell response in an animal, including compositions that are injected or absorbed into an animal. An antigen reacts with the immune system to produce an antigen-specific humoral or cellular immune response. The term "antigen" includes all related epitopes of a particular compound, composition or substance. The term "epitope" or "antigenic determinant" refers to a site on an antigen to which B- and/or T-cells respond, either alone or in conjunction with another protein such as, for example, a major histocompatibility complex ("MHC") protein or a T-cell receptor. Epitopes can be formed both from contiguous amino acids or noncontiguous amino acids juxtaposed by secondary and/or tertiary folding of a protein. Epitopes formed from contiguous amino acids are typically retained on exposure to denaturing solvents, while epitopes formed by tertiary folding are typically lost on treatment with denaturing solvents. An epitope typically includes at least 5, 6, 7, 8, 9, 10 or more amino acids—but generally less than 20 amino acids—in a unique spatial conformation. Methods of determining spatial conformation of epitopes include, for example, x-ray crystallography and 2-dimensional nuclear magnetic resonance. See, e.g., "Epitope Mapping Protocols" in *Methods in Molecular Biology, Vol.* 66, Glenn E. Morris, Ed (1996).

An antigen can be a tissue-specific (or tissue-associated) antigen or a disease-specific (or disease-associated) antigen. Those terms are not mutually exclusive, because a tissue-specific antigen can also be a disease-specific antigen. A tissue-specific antigen is expressed in a limited number of tissues. Tissue-specific antigens include, for example, prostate-specific antigen ("PSA"). A disease-specific antigen is expressed coincidentally with a disease process, where antigen expression correlates with or is predictive of development of a particular disease. Disease-specific antigens include, for example, HER-2, which is associated with certain types of breast cancer, or PSA, which is associated with prostate cancer. A disease-specific antigen can be an antigen recognized by T-cells or B-cells.

Cancer; Neoplasm; Tumor: A malignant growth arising from a particular body tissue that has undergone characteristic loss of structural differentiation, generally accompanied by increased capacity for cell division, invasion of surrounding tissue, and the capacity for metastasis. Tumors may be benign or malignant. For example, prostate cancer is a malignant neoplasm that arises in or from prostate tissue, ovarian cancer is a malignant neoplasm that arises in or from ovarian tissue, colon cancer is a malignant neoplasm that arises in or from colon tissue, and lung cancer is a malignant neoplasm that arises in or from lung tissue. Residual cancer is cancer that remains in a subject after treatment given to the subject to reduce or eradicate the cancer. Metastatic cancer is a cancer at one or more sites in the body other than the site of origin of the original (primary) cancer from which the metastatic cancer is derived.

cDNA (complementary DNA): A piece of DNA lacking internal non-coding segments (introns) and regulatory sequences that determine the timing and location of transcription initiation and termination. cDNA can be synthesized in the laboratory by reverse transcription of messenger RNA ("mRNA") extracted from cells.

Conservative variant: A "conservative" variant is a variant protein or polypeptide having one or more amino acid substitutions that do not substantially affect or decrease an activity or antigenicity of the protein or an antigenic epitope thereof. Generally conservative substitutions are those in which a particular amino acid is substituted with another amino acid having the same or similar chemical characteristics. For example, replacing a basic amino acid such as lysine with another basic amino acid such as arginine or glutamine is a conservative substitution. The term conservative variant also includes the use of a substituted amino acid in place of an unsubstituted parent amino acid, provided that antibodies raised to the substituted polypeptide also immunoreact with the unsubstituted polypeptide, and/or that the substituted polypeptide retains the function of the unsubstituted polypeptide. Non-conservative substitutions are those that replace a particular amino acid with one having different chemical characteristics, and typically reduce an activity or antigenicity of the protein or an antigenic epitope thereof.

Specific, non-limiting examples of conservative substitutions include the following examples:

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

CD4: Cluster of differentiation factor 4, a T-cell surface protein that mediates interaction with the MHC Class II molecule. Cells that express CD4, referred to as "CD4$_+$," cells, are often helper T ("T$_H$") cells.

CD8: Cluster of differentiation factor 8, a T-cell surface protein that mediates interaction with the MHC Class I molecule. Cells that express CD8, referred to as "CD8$_+$," cells, are often cytotoxic T ("CTL") cells.

TLR5 Ligand; TLR5L; flagellin: Toll-like receptor 5 (TLR5) recognizes flagellin from both Gram-positive and Gram-negative bacteria. Activation of the receptor stimulates the production of proinflammatory cytokines, such as TNF-α, through signaling via the adaptor protein MyD88. TLR5 can generate a proinflammatory signal as a homodimer suggesting that it might be the only TLR participating in flagellin recognition. However, TLR5 may require the presence of a co-receptor or adaptor molecule for efficient ligand recognition and/or signaling. Flagellin FliC from *Salmonella Tyhimurium* (494 amino acid protein) is a highly conserved molecule among both gram-negative and gram-positive bacteria. Flagellin is a potent stimulator of innate immune responses in a number of eukaryotic cells and organisms, including both mammals and plants. In mammals, flagellin is recognized by TLR5 and the inflammasome and triggers defense responses both systemically and at epithelial surfaces. Flagellin induces the activation of NF-κB and the production of cytokines and nitricoxide depending on the nature of the TLR5 signaling complex.

The amino acid sequence of flagellin FliC from *Salmonella Tyhimurium* is set forth in SEQ ID NO:1. The term flagellin encompasses the native amino acid sequence as set forth, for example, in SEQ ID NO:1, protein fragments still able elicit an immune response in a subject, as well as homologues or variants of proteins and protein fragments including, for example, glycosylated proteins or polypeptides. Thus, flagellin proteins and polypeptides are not limited to particular native amino acid sequences but encompass sequences identical to the native sequence as well as modifications to the native sequence, such as deletions, additions, insertions and substitutions. Preferably, such homologues or variants have at least about 80%, 81%, 82%, 83%, 84%, 85%, 86%, 87%, 88%, or 89%, at least about 90%, 91%, 92%, 93%, or 94%, at least about 95%, 96%, 97%, 98% or 99%, or about 100% amino acid sequence identity with the referenced protein or polypeptide. The term homologue or variant also encompasses truncated, deleted or otherwise modified nucleotide or protein sequences.

Techniques for determining sequence identity between amino acid sequences are known in the art. Two or more sequences can be compared by determining their "percent identity." The percent identity of two sequences is the number of exact matches between two aligned sequences divided by the length of the shorter sequence and multiplied by 100.

"Percent (%) amino acid sequence identity" with respect to proteins, polypeptides, antigenic protein fragments, antigens and epitopes described herein is defined as the percentage of amino acid residues in a candidate sequence that are identical with the amino acid residues in the reference sequence (i.e., the protein, polypeptide, antigenic protein fragment, antigen or epitope from which it is derived), after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the level of ordinary skill in the art, for example, using publically available computer software such as BLAST, ALIGN, or Megalign (DNASTAR) software. Those skilled in the art can determine appropriate parameters for measuring alignment, including any algorithms needed to achieve maximum alignment over the full length of the sequences being compared.

Chemotherapy; chemotherapeutic agents: Any therapeutically useful chemical agent for the treatment of diseases characterized by abnormal cell growth, including tumors, neoplasms and cancer. Commonly used classes of chemotherapeutics include alkylating agents, antimetabolites, natural products, or hormones and their antagonists. Alkylating agents include nitrogen mustards, alkyl sulfonates, and nitrosoureas. Antimetabolites include folic acid analogs, pyrimidine analogs, and purine analogs. Natural products include vinca alkaloids, epipodophyllotoxins, antibiotics, and enzymes. Miscellaneous agents include platinum coordination complexes, substituted ureas, methyl hydrazine derivatives, and adrenocortical suppressants. Hormones and hormone antagonists include adrenocorticosteroids, progestins, estrogens, antiestrogens, and androgens.

Costimulatory molecule: T-cell activation typically requires binding of the T-cell receptor ("TCR") with a peptide-MHC complex as well as a second signal delivered via the interaction of a costimulatory molecule with its ligand. Costimulatory molecules are molecules that, when bound to their ligand, deliver the second signal required for T-cell activation. The most well-known costimulatory molecule on the T-cell is CD28, which binds to either B7-1 or B7-2. Other costimulatory molecules that can also provide the second signal necessary for activation of T-cells include intracellular adhesion molecule-1 ("ICAM-1"), intracellular adhesion molecule-2 ("ICAM-2"), leukocyte function associated antigen-1 ("LEA-1"), leukocyte function associated antigen-2 ("LEA-2"), and leukocyte function associated antigen-3 ("LEA-3").

Degenerate variant: A polynucleotide encoding a protein or fragment thereof that includes a sequence that contains codons that differ from the native or wild-type gene sequence but still specify the same amino acid. The genetic code includes 20 natural amino acids, most of which are specified by more than one codon. All degenerate nucleotide sequences are encompassed in this disclosure provided the amino acid sequence of the Brachyury protein encoded by the degenerate polynucleotide remains unchanged.

Dendritic cell (DC): Dendritic cells are the primary antigen presenting cells ("APCs") involved in primary immune responses. Dendritic cells include plasmacytoid dendritic cells and myeloid dendritic cells. Their major function is to obtain antigen in tissues, migrate to lymphoid organs and present the antigen in order to activate T-cells. Immature dendritic cells originate in the bone marrow and reside in the periphery as immature cells.

Disease-associated antigen: A disease-associated antigen is expressed coincidentally with a particular disease process, where antigen expression correlates with or predicts development of that disease. Disease-associated antigens include, for example, HER-2, which is associated with certain types of breast cancer, or prostate-specific antigen ("PSA"), which is associated with prostate cancer. A disease-associated antigen can be an antigen recognized by T-cells or B-cells. Some disease-associated antigens may also be tissue-specific. A tissue-specific antigen is expressed in a limited number of tissues. Tissue-specific antigens include, for example, prostate-specific antigen PSA.

Disease-associated antigens can be, for example, tumor antigens, viral antigens, bacterial antigens, fungal antigens, or parasite antigens.

The term "tumor antigen" refers to antigens present expressed exclusively on, associated with, or over-expressed in tumor tissue. Exemplary tumor antigens include, but are not limited to, 5-α-reductase, α-fetoprotein ("AFP"), AM-1, APC, April, B melanoma antigen gene ("BAGE"), β-catenin, Bcl12, bcr-abl, Brachyury, CA-125, caspase-8 ("CASP-8", also known as "FLICE"), Cathepsins, CD19, CD20, CD21/complement receptor 2 ("CR2"), CD22/BL-CAM, CD23/F$_c$εRII, CD33, CD35/complement receptor 1 ("CR1"), CD44/PGP-1, CD45/leucocyte common antigen ("LCA"), CD46/membrane cofactor protein ("MCP"), CD52/CAMPATH-1, CD55/decay accelerating factor ("DAF"), CD59/protectin, CDC27, CDK4, carcinoembryonic antigen ("CEA"), c-myc, cyclooxygenase-2 ("cox-2"), deleted in colorectal cancer gene ("DCC"), DcR3, E6/E7, CGFR, EMBP, Dna78, farnesyl transferase, fibroblast growth factor-8a ("FGF8a"), fibroblast growth factor-8b ("FGF8b"), FLK-1/KDR, folic acid receptor, G250, G melanoma antigen gene family ("GAGE-family"), gastrin 17, gastrin-releasing hormone, ganglioside 2 ("GD2")/ganglioside 3 ("GD3")/ganglioside-monosialic acid-2 ("GM2"), gonadotropin releasing hormone ("GnRH"), UDP-GlcNAc: R$_1$Man(α1-6)R$_2$ [GlcNAc to Man(α1-6)] β1,6-N-acetylglucosaminyltransferase V ("GnT V"), GP1, gp100/Pme117, gp-100-in4, gp15, gp75/tyrosine-related protein-1 ("gp75/TRP-1"), human chorionic gonadotropin ("hCG"), heparanase, Her2/neu, human mammary tumor virus ("HMTV"), 70 kiloDalton heat-shock protein ("HSP70"), human telomerase reverse transcriptase ("hTERT"), insulin-like growth factor receptor-1 ("IGFR-1"), interleukin-13 receptor ("IL-13R"), inducible nitric oxide synthase ("iNOS"), Ki67, KIAA0205, K-ras, H-ras, N-ras, KSA, LKLR-FUT, melanoma antigen-encoding family ("MAGE-family", including at least MAGE-1, MAGE-2, MAGE-3, and MAGE-4), mammaglobin, MAP17, Melan-A/melanoma antigen recognized by T-cells-1 ("MART-1"), mesothelin, MIC NB, MT-MMPs, mucin, testes-specific antigen NY-ESO-1, osteonectin, p15, P170/MDR1, p53, p97/melanotransferrin, PAI-1, platelet-derived growth factor ("PDGF"), µPA, PRAME, probasin, progenipoietin, prostate-specific antigen ("PSA"), prostate-specific membrane antigen ("PSMA"), prostatic acid phosphatase ("PAP"), RAGE-1, Rb, RCAS1, SART-1, SSX-family, STAT3, STn, TAG-72, transforming growth factor-alpha ("TGF-α"), transforming growth factor-beta ("TGF-β"), Thymosin-beta-15, tumor necrosis factor-alpha ("TNF-α"), TP1, TRP-2, tyrosinase, vascular endothelial growth factor ("VEGF"), ZAG, p16INK4, and glutathione-S-transferase ("GST").

The term "viral antigen" refers to antigens derived from any disease-associated pathogenic virus. Exemplary disease-associated viral antigens include, but are not limited to, antigens derived from adenovirus, Arbovirus, Astrovirus, Coronavirus, Coxsackievirus, Crimean-Congo hemorrhagic fever virus, cytomegalovirus ("CMV"), dengue virus, Ebola virus, Epstein-Barr virus ("EBV"), Foot-and-mouth disease virus, Guanarito virus, Hendra virus, herpes simplex virus-type 1 ("HSV-1"), herpes simplex virus-type 2 ("HSV-2"), human herpesvirus-type 6 ("HHV-6"), human herpesvirus-type 8 ("HHV-8"), hepatitis A virus ("HAV"), hepatitis B virus ("HBV"), hepatitis C virus ("HCV"), hepatitis D virus ("HDV"), hepatitis E virus ("HEV"), human immunodeficiency virus ("HIV"), influenza virus, Japanese encephalitis virus, Junin virus, Lassa virus, Machupo virus, Marburg virus, measles virus, human metapneumovirus, Molluscum contagiosum virus, mumps virus, Newcastle disease virus, Nipha virus, Norovirus, Norwalk virus, human papillomavirus ("HPV"), parainfluenza virus, parvovirus, poliovirus, rabies virus, respiratory syncytial virus ("RSV"), rhinovirus, rotavirus, rubella virus, Sabia virus, severe acute respiratory syndrome virus ("SARS"), varicella zoster virus, variola virus, West Nile virus, and yellow fever virus.

The term "bacterial antigen" refers to antigens derived from any disease-associated pathogenic virus. Exemplary bacterial antigens include, but are not limited to, antigens derived from *Bacillus anthracis, Bordetella pertussis, Borrelia burgdorferi, Brucella abortus, Brucella canis, Brucella melitensis, Brucella suis, Burkholderia mallei, Burkholderia pseudomallei, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diptheriae, Enterococcus faecalis, Enterococcus faecium, Escherichia coli,* enterotoxigenic *Escherichia coli,* enteropathogenic *Escherichia coli, Escherichia coli*) 157:H7, *Francisella tularensis, Haemophilus influenza, Helicobacter pylori, Legionella pneumophila, Leptospira interrogans, Listeria monocytogenes, Mycobacterium leprae, Mycobacterium tuberculosis, Mycoplasma pneumoniae, Neisseria gonorrhoeae, Neisseria meningitides, Pseudomonas aeruginosa, Rickettsia rickettsia, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholerae,* and *Yersinia pestis.*

The term "fungal antigen" refers to antigens derived from any disease-associated pathogenic fungus. Exemplary fungal antigens include, but are not limited to, antigens derived from *Aspergillus clavatus, Aspergillus flavus, Aspergillus fumigatus, Aspergillus nidulans, Aspergillus niger, Aspergillus terreus, Blastomyces dermatitidis, Candida albicans, Candida dubliniensis, Candida glabrata, Candida parapsilosis, Candida rugosa, Candida tropicalis, Cryptococcus albidus, Cryptococcus gattii, Cryptococcus laurentii, Cryptococcus neoformans, Histoplasma capsulatum, Microsporum canis, Pneumocystis carinii, Pneumocystis jirovecii, Sporothrix schenckii, Stachbotrys chartarum, Tinea barbae, Tinea captitis, Tinea corporis, Tinea cruris, Tinea faciei, Tinea incognito, Tinea nigra, Tinea versicolor, Trichophyton rubrum* and *Trichophyton tonsurans.*

The term "parasite antigen" refers to antigens derived from any disease-associated pathogenic parasite. Exemplary parasite antigens include, but are not limited to, antigens derived from *Anisakis* spp. *Babesia* spp., *Baylisascaris procyonis, Cryptosporidium* spp., *Cyclospora cayetanensis, Diphyllobothrium* spp., *Dracunculus medinensis, Entamoeba histolytica, Giardia duodenalis, Giardia intestinalis, Giardia lamblia, Leishmania* sp., *Plasmodium falciparum, Schistosoma mansoni, Schistosoma haematobium, Schistosoma japonicum, Taenia* spp., *Toxoplasma gondii, Trichinella spiralis,* and *Trypanosoma cruzi.*

Expression Control Sequences: Nucleic acid sequences that regulate the expression of a heterologous nucleic acid sequence to which they are operatively linked. Expression control sequences are operatively linked to a nucleic acid sequence when the expression control sequences control and regulate the transcription and/or translation of the nucleic acid sequence. Thus, the term "expression control sequences" encompasses promoters, enhancers, transcription terminators, start codons, splicing signals for introns, and stop codons. The term "control sequences" includes, at a minimum, components the presence of which can influence transcription and/or translation of the heterologous nucleic acid sequence and can also include additional components whose presence is advantageous such as, for example, leader sequences and fusion partner sequences.

The term "expression control sequences" encompasses promoter sequences. A promoter is a minimal sequence sufficient to direct transcription of a homologous or heterologous gene. Also included are those promoter elements sufficient to render promoter-dependent gene expression cell-type specific, tissue-specific, or inducible by external signals or agents; such elements may be located in the 5' or 3' regions of the gene. The term "promoter" encompasses both constitutive and inducible promoters. See, e.g., Bitter et al., *Methods in Enzymology* 153:516-544 (1987). Exemplary promoter sequences include, but are not limited to, the retrovirus long terminal repeat ("LTR"), the adenovirus major late promoter, the vaccinia virus 7.5K promoter ("Pr7.5"), the vaccinia virus synthetic early/late promoter ("sE/L"), the PrSynIlm promoter, the PrLE1 promoter, the PrH5m promoter, the PrS promoter, a hybrid early/late promoter, or a cowpox virus ATI promoter.

Heterologous: Originating from separate genetic sources or species. A polypeptide that is heterologous to human Brachyury originated from a nucleic acid that does not encode human Brachyury such as, for example, mouse Brachyury, β-galactosidase, maltose binding protein, or human serum albumin.

Host cells: Cells in which a vector can be propagated and its DNA expressed. The cells may be prokaryotic (e.g., bacterial) or eukaryotic (e.g., mammalian or human). The term also encompasses progeny of the original host cell, even though all progeny may not be identical to the parental cell since there may be mutations that occur during replication.

Immune response: An adaptive response of an immune system cell, such as a B-cell, T-cell, or monocyte, to a stimulus. An adaptive response is a response to a particular antigen, and is thus described as "antigen-specific". An adaptive immune response can include the production of antibodies to a particular antigen by a B-cell, T-cell help by a CD4+ helper T-cell expanding a population of antigen-specific CD8+ T-cells ("CTLs"), cytotoxic activity of CD8+ T-cells directed against cells expressing a particular antigen, or yet another type of antigen-specific immune response.

Immunogenic composition: As used herein, the term "immunogenic composition" refers to a composition comprising a nucleic acid encoding the flagellin protein and a nucleic acid encoding a disease-associated antigen, both under the control of an expression control sequence or promoter, such as a poxvirus vector, that induces a measurable disease-associated antigen-specific, adaptive immune response. The nucleic acid or poxvirus vector may optionally include additional nucleic acids encoding, for example, one or more costimulatory molecules as described elsewhere herein. That immune response may be, for example, a CD8+ T-cell or CTL response directed against cells expressing the disease-associated antigen, or a B-cell response producing disease-associated antigen-specific antibodies. Such compositions may include the isolated nucleic acid or vector, optionally formulated with one or more pharmaceutically acceptable carriers.

Lymphocytes: A type of white blood cell that is involved in the immune defenses of the body. There are two main types of lymphocytes: B-cells and T-cells.

Major Histocompatibility Complex (MHC): A generic designation meant to encompass the histocompatability antigen systems described in different species, including the human leukocyte antigens ("HLA").

Mammal: This term includes both human and non-human mammals. Similarly, the term "subject" includes both human and veterinary subjects.

Open reading frame (ORF): A series of nucleotide codons specifying a series of amino acids without any internal termination codons that capable of being translated to produce a polypeptide.

Operably linked: A first nucleic acid sequence is operably linked to a second nucleic acid sequence when the first nucleic acid sequence is placed in a functional relationship with the second nucleic acid sequence. For example, a promoter is operably linked to a coding sequence if the promoter is placed in a position where it can direct transcription of the coding sequence. Generally, operably linked DNA sequences are contiguous and, where necessary to join two protein-coding regions, in the same reading frame.

Pharmaceutically acceptable carriers: Remington's Pharmaceutical Sciences, by E. W. Martin, Mack Publishing Co., Easton, Pa., 15th Edition (1975), describes compositions and formulations using conventional pharmaceutically acceptable carriers suitable for administration of the vectors and compositions disclosed herein. Generally the nature of the carrier used depends on the particular mode of administration being employed. For example, parenteral formulations usually comprise injectable fluids that include pharmaceutically and physiologically acceptable fluids such as water, physiological saline, balanced salt solutions, aqueous dextrose, glycerol or the like, as a vehicle. For solid compositions (such as powders, pills, tablets, or capsules), conventional non-toxic solid carriers include, for example, pharmaceutical grades of mannitol, lactose, starch, or magnesium stearate. Pharmaceutical compositions can also contain minor amounts of non-toxic auxiliary substances such as wetting or emulsifying agents, preservatives, pH-buffering agents and the like such as, for example, sodium acetate or sorbitan monolaurate.

Polynucleotide; nucleic acid: The term polynucleotide refers to a nucleic acid polymer at least 300 bases long composed of ribonucleotides (i.e., RNA) or deoxyribonucleotides (i.e., DNA or cDNA) and capable of encoding a polypeptide or protein. The term includes single- and double-stranded forms of DNA.

Polypeptide or Protein: The term polypeptide or protein refers to a polymer at least 100 amino acids long, generally greater than 50 amino acids in length.

Poxvirus: The term poxvirus refers to any of the genera of poxviruses capable of infecting humans (e.g., orthopox viruses, avipox viruses, parapox viruses, yatapox viruses, and molluscipox viruses) whether productively or not, but preferably the orthopox and/or avipox viruses. Orthopox viruses include smallpox virus (also known as variola virus), vaccinia virus, cowpox virus, and monkeypox virus. Avipox viruses include canarypox virus and fowlpox virus. The term "vaccinia virus" refers to both the wild-type vaccinia virus and any of the various attenuated strains or isolates subsequently isolated including, for example, vaccinia virus-Western Reserve, vaccinia virus-Copenhagen, Dryvax (also known as vaccinia virus-Wyeth), ACAM2000, modified vaccinia virus Ankara ("MVA"), and modified vaccinia virus Ankara-Bavarian Nordic ("MVA-BN").

Prime-boost vaccination: The term "prime-boost vaccination" refers to a vaccination strategy using a first, priming injection of a vaccine targeting a specific antigen followed at intervals by one or more boosting injections of the same vaccine. Prime-boost vaccination may be homologous or heterologous. A homologous prime-boost vaccination uses a vaccine comprising the same immunogen and vector for both the priming injection and the one or more boosting injections. A heterologous prime-boost vaccination uses a vaccine comprising the same immunogen for both the priming injection and the one or more boosting injections but different vectors for the priming injection and the one or more boosting injections. For example, a homologous prime-boost vaccination may use an MVA vector comprising nucleic acids expressing Brachyury and TRICOM for both the priming injection and the one or more boosting injections. In contrast, a heterologous prime-boost vaccination may use an MVA vector comprising nucleic acids expressing Brachyury and TRICOM for the priming injection and a fowlpox vector comprising nucleic acids expressing Brachyury and TRICOM for the one or more boosting injections. Heterologous prime-boost vaccination also encompasses various combinations such as, for example, use of a plasmid encoding an immunogen in the priming injection and use of a poxvirus vector encoding the same immunogen in the one or more boosting injections, or use of a recombinant protein immunogen in the priming injection and use of a plasmid or poxvirus vector encoding the same protein immunogen in the one or more boosting injections.

Recombinant; recombinant nucleic acid; recombinant vector; recombinant poxvirus: The term "recombinant" when applied to a nucleic acid, vector, poxvirus and the like refers to a nucleic acid, vector, or poxvirus made by an artificial combination of two or more otherwise heterologous segments of nucleic acid sequence, or to a nucleic acid, vector or poxvirus comprising such an artificial combination of two or more otherwise heterologous segments of nucleic acid sequence. The artificial combination is most commonly accomplished the artificial manipulation of isolated segments of nucleic acids, using well-established genetic engineering techniques.

Sequence identity: The term "sequence identity" refers to the degree of similarity between the nucleic acid or amino acid sequences. Sequence identity is frequently measured in terms of percent identity (often described as sequence "similarity" or "homology"). The higher the percent sequence identity, the more similar the two sequences are. Homologs or variants of a Brachyury protein will have a relatively high degree of sequence identity when aligned using standard methods.

Methods of aligning sequences for comparison are well known in the art. Various programs and alignment algorithms are described in: Smith and Waterman, Adv. Appl. Math. 2:482, 1981; Needleman and Wunsch, J. Mol. Biol. 48:443, 1970; Higgins and Sharp, Gene 73:237, 1988; Higgins and Sharp, CABIOS 5:151, 1989; Corpet et al., Nucl. Acids Res. 16:10881, 1988; and Pearson and Lipman, Proc. Nat'l Acad. Sci. USA 85:2444, 1988. In addition, Altschul et al., Nature Genet. 6:119, 1994, presents a detailed consideration of sequence alignment methods and homology calculations. The NCBI Basic Local Alignment Search Tool (BLAST) (Altschul et al., J. Mol. Biol. 215:403, 1990) is available from several sources, including the National Center for Biotechnology Information (NCBI, Bethesda, Md.; see also blast.ncbi.nlm.nih.gov/Blast.cgi), for use in connection with the sequence analysis programs blastp, blastn, blastx, tblastn and tblastx.

Homologs and variants of a human Brachyury protein typically have at least 90%, 91%, 92%, 93%, 94%, 95%, 96%, 97%, 98% or 99% amino acid sequence identity over a full-length alignment with the amino acid sequence of wild-type human Brachyury prepared with NCBI Blast v2.0, using blastp set to the default parameters. For comparisons of amino acid sequences of greater than about 30 amino acids, the Blast 2 sequences function is employed using the default BLOSUM62 matrix set to the default parameters (gap existence cost of 11, and a per residue gap cost of 1).

Subject: Living multi-cellular vertebrate organisms, including, for example, humans, non-human mammals and birds. The term "subject" may be used interchangeably with the term "animal" herein.

T-Cell: A lymphocyte or white blood cell essential to the adaptive immune response. T-cells include, but are not limited to, CD4+ T-cells and CD8+ T-cells. A CD4+ T-cell is an immune cell that carries a marker on its surface known as "cluster of differentiation 4" ("CD4"). These cells, also known as helper T-cells, help orchestrate the immune response, including both antibody and CTL responses. CD8+ T-cells carry the "cluster of differentiation 8" ("CD8") marker. CD8+ T-cells include both CTLs, memory CTLs, and suppressor T-cells.

Therapeutically active polypeptide: An agent composed of amino acids, such as a Brachyury protein, that induces an adaptive immune response, as measured by clinical response (e.g., an increase in CD4+ T-cells, CD8+ T-cells, or B-cells, an increase in Brachyury-specific cytolytic activity, a measurable reduction in tumor size, or a reduction in number of metastases). Therapeutically active molecules can also be made from nucleic acids such as, for example, a poxvirus vector comprising a nucleic acid encoding human Brachyury operably linked to an expression control sequence.

Transduced or Transformed: The term "transduced" or "transformed" refers to a cell into which a recombinant nucleic acid has been introduced by standard molecular biological methods. As used herein, the term transduction encompasses all techniques by which a nucleic acid molecule might be introduced into such a cell, including infection with viral vectors, transformation with plasmid vectors, and introduction of naked DNA by electroporation, lipofection, or particle gun acceleration.

Treating cancer: The term "treating cancer" refers to a therapeutic intervention intended to reduce or eliminate a sign or symptom of the cancer or to delay progression of the disease and increase overall survival of a subject having cancer. Cancer may be treated by standard chemotherapy, radiation, or active immunotherapy such as, for example, administration of a recombinant vaccinia virus comprising a nucleic acid encoding a Brachyury protein. Reducing or eliminating a sign or symptom of the cancer encompasses a wide variety of effects including, for example reducing signs or symptoms of a tumor, reducing tumor volume, reducing the number of metastases, increasing response duration, increasing time to progression, increasing disease-free survival, increasing progression-free survival, or increasing the overall survival of patients having the disease.

TRICOM: A Triad of COstimlatory Molecules consisting of B7-1 (also known as CD80), intracellular adhesion molecule-1 (ICAM-1, also known as CD54) and lymphocyte function-associated antigen-3 (LFA-3, also known as CD58), commonly included in recombinant viral vectors (e.g., poxviral vectors) expressing a specific antigen in order to increase the antigen-specific immune response. The individual components of TRICOM can be under the control of the same or different promoters, and can be provided on the same vector with the specific antigen or on a separate vector. Exemplary vectors are disclosed, for example, in Hodge et al., "A Triad of Costimulatory Molecules Synergize to Amplify T-Cell Activation," *Cancer Res.* 59:5800-5807 (1999) and U.S. Pat. No. 7,211,432 B2, both of which are incorporated herein by reference.

Vector: A nucleic acid molecule introduced into a host cell, thereby producing a transduced or transformed host cell. Vectors generally include nucleic acid sequences enabling them to replicate in a host cell, such as an origin of replication, as well as one or more selectable marker genes, expression control sequences, restriction endonuclease recognition sequences, primer sequences and a variety of other genetic elements known in the art. Commonly used vector types include plasmids for expression in bacteria (e.g., *E. coli*) or yeast (e.g., *S. cerevisiae*), shuttle vectors for constructing recombinant poxviruses, cosmids, bacterial artificial chromosomes, yeast artificial chromosomes, and viral vectors. Viral vectors include poxvirus vectors, retrovirus vectors, adenovirus vectors, herpes virus vectors, baculovirus vectors, Sindbis virus vecturs, and poliovirus vectors, among others. Poxvirus vectors include, but are not limited to orthopox viruses, avipox viruses, parapox viruses, yatapox viruses, and molluscipox viruses, but preferably the orthopox and/or avipox viruses. Orthopox viruses include smallpox virus (also known as variola virus), vaccinia virus, cowpox virus, and monkeypox virus. Avipox viruses include canarypox virus and fowlpox virus. The term "vaccinia virus" refers to both the wild-type vaccinia virus and any of the various attenuated strains or isolates subsequently isolated including, for example, vaccinia virus-Western Reserve, vaccinia virus-Copenhagen, Dryvax (also known as vaccinia virus-Wyeth), ACAM2000, modified vaccinia virus Ankara ("MVA"), and modified vaccinia virus Ankara-Bavarian Nordic ("MVA-BN").

Discussion

Embodiments of the present disclosure demonstrate the advantage of rMVA-flagellin construct administered via a mucosal route, in this case using the i.n. route. It has been shown that i.n. rMVA-flagellin immunization is a better vaccine than the stand-alone rMVA administered via the similar route. rMVA-flagellin has the capacity to induce better immune responses systemically and in the mucosal compartments, compared to rMVA. This is shown with the enhanced frequency of MVA and OVA-specific CTL in both the spleen and the lung, concomittantly with increased frequency of those cytokine-producing CTL, namely IFN-γ and TNF-α in the spleen. The presently disclosed immunogenic compositions have also been shown to improve the quality of the response with an increase of IFN-γ$^+$TNF-α$^+$ producing CTL in the spleen. This suggests a beneficial effect of the rMVA-flagellin at inducing better T cell responses. The presently disclosed immunogenic composition has also demonstrated the beneficial effect rMVA-flagellin has on B cell responses, more specifically on Th1-type immune responses with higher serum IgG2c titers compared to rMVA. Both enhanced MVA and OVA-specific IgG2c titers can be observed following i.n. rMVA-flagellin immunization in the serum and the BAL. Of course, mucosal immunization ultimately induces mucosal antibody responses, characterised with the production of secretory IgA at mucosal surfaces. The results show that both the stand-alone rMVA and rMVA-flagellin vaccine administered via the i.n. route can induce the production of IgA in the BAL. Having established that the immunogenic composition is more efficient at inducing systemic and mucosal immune responses in the upper-respiratory tract, it was investigated whether i.n. rMVA-flagellin immunization could also induce immune responses in the gastro-intestinal compartment. It was confirmed that intestinal immunity could be achieved, with the presence of IgA in the intestinal washes.

By investigating the in vivo innate immune response, an enhanced cytokine response in the BAL of rMVA-flagellin-immunized mice compared to i.n. rMVA-immunized mice, with enhanced IL-1β, IL-18 and TNF-α production was shown. In addition, when the innate immune sensing of rMVA-flagellin was investigated we could confirm rMVA-flagellin-specific inflammasome and TLR5-dependent innate immune recognition. Also activation of mucosal DC by rMVA-flagellin was shown.

Modified Vaccinia Virus Ankara (MVA)

MVA has been generated by more than 570 serial passages on chicken embryo fibroblasts of the dermal vaccinia strain Ankara [Chorioallantois vaccinia virus Ankara virus, CVA; for review see Mayr et al. (1975), Infection 3, 6-14] that was maintained in the Vaccination Institute, Ankara, Turkey for many years and used as the basis for vaccination of humans. However, due to the often severe post-vaccinal complications associated with vaccinia viruses, there were several attempts to generate a more attenuated, safer smallpox vaccine.

During the period of 1960 to 1974, Prof. Anton Mayr succeeded in attenuating CVA by over 570 continuous passages in CEF cells [Mayr et al. (1975)]. It was shown in a variety of animal models that the resulting MVA was avirulent [Mayr, A. & Danner, K. (1978), Dev. Biol. Stand. 41: 225-234]. As part of the early development of MVA as a pre-smallpox vaccine, there were clinical trials using MVA-517 in combination with Lister Elstree [Stickl (1974), Prev. Med. 3: 97-101; Stickl and Hochstein-Mintzel (1971), Munich Med. Wochenschr. 113: 1149-1153] in subjects at risk for adverse reactions from vaccinia. In 1976, MVA derived from MVA-571 seed stock (corresponding to the 571$^{st}$ passage) was registered in Germany as the primer vaccine in a two-stage parenteral smallpox vaccination program. Subsequently, MVA-572 was used in approximately 120,000 Caucasian individuals, the majority children between 1 and 3 years of age, with no reported severe side effects, even though many of the subjects were among the population with high risk of complications associated with vaccinia (Mayr et al. (1978), Zentralbl. Bacteriol. (B) 167: 375-390). MVA-572 was deposited at the European Collection of Animal Cell Cultures as ECACC V94012707.

As a result of the passaging used to attenuate MVA, there are a number of different strains or isolates, depending on the passage number in CEF cells. For example, MVA-572 was used in Germany during the smallpox eradication program, and MVA-575 was extensively used as a veterinary vaccine. MVA-575 was deposited on Dec. 7, 2000, at the European Collection of Animal Cell Cultures (ECACC) with the deposition number V00120707. The attenuated CVA-virus MVA (Modified Vaccinia Virus Ankara) was obtained by serial propagation (more than 570 passages) of the CVA on primary chicken embryo fibroblasts.

Even though Mayr and colleagues demonstrated during the 1970s that MVA is highly attenuated and avirulent in humans and mammals, certain investigators have reported that MVA is not fully attenuated in mammalian and human cell lines since residual replication might occur in these cells [Blanchard et al. (1998), J Gen Virol 79:1159-1167; Carroll & Moss (1997), Virology 238:198-211; U.S. Pat. No. 5,185,146; Ambrosini et al. (1999), J Neurosci Res 55: 569]. It is assumed that the results reported in these publications have been obtained with various known strains of MVA, since the viruses used essentially differ in their properties, particularly in their growth behaviour in various cell lines. Such residual replication is undesirable for various reasons, including safety concerns in connection with use in humans.

Strains of MVA having enhanced safety profiles for the development of safer products, such as vaccines or pharmaceuticals, have been developed by Bavarian Nordic: MVA was further passaged by Bavarian Nordic and is designated MVA-BN. MVA as well as MVA-BN lacks approximately 15% (31 kb from six regions) of the genome compared with ancestral CVA virus. The deletions affect a number of virulence and host range genes, as well as the gene for Type A inclusion bodies. A sample of MVA-BN corresponding to passage 583 was deposited on Aug. 30, 2000 at the European Collection of Cell Cultures (ECACC) under number V00083008.

MVA-BN can attach to and enter human cells where virally-encoded genes are expressed very efficiently. However, assembly and release of progeny virus does not occur. MVA-BN is strongly adapted to primary chicken embryo fibroblast (CEF) cells and does not replicate in human cells. In human cells, viral genes are expressed, and no infectious virus is produced. MVA-BN is classified as Biosafety Level 1 organism according to the Centers for Disease Control and Prevention in the United States. Preparations of MVA-BN and derivatives have been administered to many types of animals, and to more than 2000 human subjects, including immune-deficient individuals. All vaccinations have proven to be generally safe and well tolerated. Despite its high attenuation and reduced virulence, in preclinical studies MVA-BN has been shown to elicit both humoral and cellular immune responses to vaccinia and to heterologous gene products encoded by genes cloned into the MVA genome [E. Harrer et al. (2005), Antivir. Ther. 10(2):285-300; A. Cosma et al. (2003), Vaccine 22(1):21-9; M. Di Nicola et al. (2003), Hum. Gene Ther. 14(14):1347-1360; M. Di Nicola et al. (2004), Clin. Cancer Res., 10(16):5381-5390].

"Derivatives" or "variants" of MVA refer to viruses exhibiting essentially the same replication characteristics as MVA as described herein, but exhibiting differences in one or more parts of their genomes. MVA-BN as well as a derivative or variant of MVA-BN fails to reproductively replicate in vivo in humans and mice, even in severely immune suppressed mice. More specifically, MVA-BN or a derivative or variant of MVA-BN has preferably also the capability of reproductive replication in chicken embryo fibroblasts (CEF), but no capability of reproductive replication in the human keratinocyte cell line HaCat [Boukamp et al (1988), J Cell Biol 106: 761-771], the human bone osteosarcoma cell line 143B (ECACC No. 91112502), the human embryo kidney cell line 293 (ECACC No. 85120602), and the human cervix adenocarcinoma cell line HeLa (ATCC No. CCL-2). Additionally, a derivative or variant of MVA-BN has a virus amplification ratio at least two-fold less, more preferably three-fold less than MVA-575 in Hela cells and HaCaT cell lines. Tests and assay for these properties of MVA variants are described in WO 02/42480 (US 2003/0206926) and WO 03/048184 (US 2006/0159699), both incorporated herein by reference.

The term "not capable of reproductive replication" or "no capability of reproductive replication" is, for example, described in WO 02/42480, which also teaches how to obtain MVA having the desired properties as mentioned above. The term applies to a virus that has a virus amplification ratio at 4 days after infection of less than 1 using the assays described in WO 02/42480 or in U.S. Pat. No. 6,761,893.

The term "fails to reproductively replicate" refers to a virus that has a virus amplification ratio at 4 days after infection of less than 1. Assays described in WO 02/42480 or in U.S. Pat. No. 6,761,893 are applicable for the determination of the virus amplification ratio.

The amplification or replication of a virus is normally expressed as the ratio of virus produced from an infected cell (output) to the amount originally used to infect the cell in the first place (input) referred to as the "amplification ratio". An amplification ratio of "1" defines an amplification status where the amount of virus produced from the infected cells is the same as the amount initially used to infect the cells, meaning that the infected cells are permissive for virus infection and reproduction. In contrast, an amplification ratio of less than 1, i.e., a decrease in output compared to the input level, indicates a lack of reproductive replication and therefore attenuation of the virus.

The advantages of MVA-based vaccine include their safety profile as well as availability for large scale vaccine production. Preclinical tests have revealed that MVA-BN demonstrates superior attenuation and efficacy compared to other MVA strains (WO02/42480). An additional property of MVA-BN strains is the ability to induce substantially the same level of immunity in vaccinia virus prime/vaccinia virus boost regimes when compared to DNA-prime/vaccinia virus boost regimes.

The recombinant MVA-BN viruses, the most preferred embodiment herein, are considered to be safe because of their distinct replication deficiency in mammalian cells and their well-established avirulence. Furthermore, in addition to its efficacy, the feasibility of industrial scale manufacturing can be beneficial. Additionally, MVA-based vaccines can deliver multiple heterologous antigens and allow for simultaneous induction of humoral and cellular immunity.

In a preferred embodiment, the recombinant MVA vector of any of the embodiments used for generating the recombinant virus is a MVA-BN virus or a derivative having the capability of reproductive replication in vitro in chicken embryo fibroblasts (CEF) cells, but no capability of reproductive replication in the human keratinocyte cell line HaCat, the human bone osteosarcoma cell line 143B, the human embryo kidney cell line 293, and the human cervix adenocarcinoma cell line HeLa.

In another embodiment, the recombinant MVA vector of any of the embodiments used for generating the recombinant virus is MVA-BN as deposited at the European Collection of Animal Cell cultures (ECACC) under accession number V00083008.

MVA vectors useful for the present invention can be prepared using methods known in the art, such as those described in WO 02/042480 and WO 02/24224, both of which are incorporated by reference herein.

In another aspect, an MVA viral strain suitable for generating the recombinant virus may be strain MVA-572, MVA-575 or any similarly attenuated MVA strain. Also suitable may be a mutant MVA, such as the deleted *chorioallantois vaccinia* virus Ankara (dCVA). A dCVA comprises del I, del II, del III, del IV, del V, and del VI deletion sites of the MVA genome. The sites are particularly useful for the insertion of multiple heterologous sequences. The dCVA can reproductively replicate (with an amplification ratio of greater than 10) in a human cell line (such as human 293, 143B, and MRC-5 cell lines), which then enable the optimization by further mutation useful for a virus-based vaccination strategy (see, e.g., WO 2011/092029).

Immunogenic Compositions and Disease-Associated Antigens

In one aspect, provided herein are immunogenic compositions comprising recombinant poxviruses such as, for example, modified vaccinia virus Ankara (MVA) comprising a nucleic acid sequence encoding a flagellin and a nucleic acid sequence encoding a heterologous disease-associated antigen, wherein the immunogenic composition induces increased T-cell and/or B-cell immune responses specific for the heterologous disease-associated antigen when administered to a subject, e.g. a human subject, as compared to T-cell and/or B-cell immune responses specific for the heterogous disease-associated antigen induced by administration of a recombinant MVA comprising a nucleic acid sequence encoding a heterologous disease-associated antigen but not a nucleic acid sequence encoding a flagellin.

In certain embodiments, the nucleic acid sequence encodes a Flagellin having an amino acid sequence having at least 95%, 96%, 97%, 98%, 99%, or 100% amino acid sequence identity to SEQ ID NO:1. In certain embodiments, the nucleic acid sequence encodes a flagellin having an amino acid sequence having at least 95% amino acid sequence identity to SEQ ID NO:1. In certain embodiments, the nucleic acid sequence encodes a flagellin having an amino acid sequence having at least 96% amino acid sequence identity to SEQ ID NO:1. In certain embodiments, the nucleic acid sequence encodes a flagellin having an amino acid sequence having at least 97% amino acid sequence identity to SEQ ID NO:1. In certain embodiments, the nucleic acid sequence encodes a flagellin having an amino acid sequence having at least 98% amino acid sequence identity to SEQ ID NO:1. In certain embodiments, the nucleic acid sequence encodes a flagellin having an amino acid sequence having at least 99% amino acid sequence identity to SEQ ID NO:1. In certain embodiments, the nucleic acid sequence encodes a flagellin having the amino acid sequence of SEQ ID NO:1.

In certain embodiments, the immunogenic compositions comprise at least two recombinant poxviruses (e.g., MVA), one comprising a nucleic acid encoding flagellin and one comprising a nucleic acid encoding a heterologous disease-associated antigen, wherein the immunogenic composition induces increased T-cell immune responses specific for the heterologous disease-associated antigen when administered to a human subject.

Nucleic acids encoding flagellin can be operatively linked to expression control sequences. An expression control sequence operatively linked to a coding sequence is joined such that expression of the coding sequence is achieved under conditions compatible with the expression control sequences. The expression control sequences include, but are not limited to, appropriate promoters, enhancers, transcription terminators, a start codon at the beginning a protein-encoding open reading frame, splicing signals for introns, and in-frame stop codons. Suitable promoters include, but are not limited to, the SV40 early promoter, the retrovirus LTR, the adenovirus major late promoter, the human CMV immediate early I promoter, and various poxvirus promoters including, but not limited to the following vaccinia virus or MVA—derived promoters: the 30K promoter, the I3 promoter, the sE/L promoter, the Pr7.5K, the 40K promoter, the C1 promoter, the PrSynIIm promoter, the PrLE1 promoter, the PrH5m promoter, the PrS promoter, a hybrid early/late promoter, the PrS5E promoter, the PrA5E promoter, and the Pr4LS5E promoter; a cowpox virus ATI promoter, or the following fowlpox-derived promoters: the Pr7.5K promoter, the I3 promoter, the 30K promoter, or the 40K promoter.

Additional expression control sequences include, but are not limited to, leader sequences, termination codons, polyadenylation signals and any other sequences necessary for the appropriate transcription and subsequent translation of the nucleic acid sequence encoding the desired recombinant protein (e.g., flagellin) in the desired host system. The recombinant poxviruses (e.g., MVA) may also contain additional elements necessary for the transfer and subsequent replication of the expression vector containing the nucleic acid sequence in the desired host system. It will further be understood by one skilled in the art that such vectors are easily constructed using conventional methods (Ausubel et al., (1987) in "Current Protocols in Molecular Biology," John Wiley and Sons, New York, N.Y.) and are commercially available.

In certain embodiments, the recombinant poxviruses (e.g., MVA) disclosed herein further comprise nucleic acid molecules encoding one or more costimulatory molecules. In certain embodiments, the one or more costimulatory molecules are selected from the group consisting of B7-1, B7-2, ICAM-1, LFA-3, 4-1BBL, CD59, CD40, CD70, VCAM-1 and OX-40L. In certain embodiments, the recombinant poxviruses (e.g., MVA) disclosed herein further comprise a nucleic acid molecule encoding one costimulatory molecule. In certain embodiments, the recombinant poxviruses (e.g., MVA) disclosed herein further comprise one or more nucleic acid molecules encoding two costimulatory molecules. In certain embodiments, the recombinant poxviruses (e.g., MVA) disclosed herein further comprise one or more nucleic acid molecules encoding three costimulatory molecules. In certain embodiments, the three costimulatory molecules are B7-1, ICAM-1, and LFA-3 (i.e., TRICOM). In certain embodiments, the recombinant poxviruses (e.g., MVA) comprise one or more nucleic acid molecules encoding human B7.1, human ICAM-1, and human LFA-3. In certain embodiments, the nucleic acid molecules encoding B7-1, ICAM-1, and LFA-3 are under the control of the same expression control sequences. In certain embodiments, the nucleic acids encoding B7-1, ICAM-1, and LFA-3 are under control of different expression control sequences.

The use of at least three costimulatory molecules produces a synergistic enhancement of the immune response induced by the recombinant poxviruses (e.g., MVA) encoding flagellin, and the synergy is not obtainable using only one or two costimulatory molecules. Effective combinations of costimulatory molecules are selected from the group consisting of: B7-1, ICAM-1, and LFA-3; B7-1, B7-2, ICAM-1, and LFA-3; B7-1, B7-2, ICAM-1, and 4-1BBL; B7-1, B7-2, ICAM-1, LFA-3, and 4-1BBL; CD59 and VCAM-1; B7-1 and B7-2; CD59, CD40, 4-1 BBL, and CD70; VCAM-1, B7-1, and B7-2; and OX-40L and 4-1BBL; and the like, depending on the desired immune response and the disease or condition to be treated (see, e.g., U.S. Pat. No. 7,211,432, which is hereby incorporated herein by reference in its entirety).

Genes or functional portions thereof encoding costimulatory molecules that can be incorporated into the recombinant poxviruses (e.g., MVA) disclosed herein include but are not limited to B7-1, B7-2, ICAM-1, LFA-3, 4-1BBL, CD59, CD40, CD70, OX-40L, and their mammalian homologs.

The term "B7" refers to a family of costimulatory molecules which are members of the immunoglobulin ("Ig") gene superfamily. The members include B7-1 (also known as "CD80") and B7-2 (also known as "CD86"), which are the natural ligands of CD28 and CTLA-4 (also known as "CD152"). The gene sequence of mouse B7.1 is deposited in GenBank under Accession No. X60958. See, e.g., Freeman et al., J. Immunol. 143:2714-2722 (1989). The gene sequence of mouse B7.2 is deposited in GenBank under Accession No. L25606. See, e.g., Azuma et al., Nature 366:76-79 (1993). The human homologs of the mouse B7-1 and B7-2 costimulatory molecules include CD80, the homolog of mouse B7.1, and CD86, the homolog of mouse B7.2. The gene sequence of human B7.1 is deposited in GenBank under Accession No. M27533. The gene sequence of human B7.2 (CD86) is deposited in GenBank under Accession Nos. U04343 and AF099105.

The term "intercellular adhesion molecule" ("ICAM") refers to a family of costimulatory molecules which are members of the Ig gene superfamily. The members include ICAM-1 (also known as "CD54"), ICAM-2 (also known as "CD102"), ICAM-3 (also known as "CD50"), ICAM-4 (also known as "CD242"), and ICAM-5, which are the natural ligands of the leukocyte integrins CD11a/CD18 (also known as "leukocyte function-associated antigen-1" or "LFA-1") which are expressed on the surface of lymphocytes and granulocytes. The gene sequence of human ICAM-1 is deposited in GenBank under Accession No. J03132. The gene sequence of mouse ICAM-1 is deposited in GenBank under Accession No. X52264.

The term "leukocyte function-associated antigen" ("LEA") refers to a family of costimulatory molecules involved in cell adhesion. The members include LFA-1 (also known as "CD11a/CD18"), LFA-2 (also known as "CD2"), and LFA-3 (also known as "CD58"). LFA-3, a glycosylphosphatidylinositol-linked glycoprotein, is a member of the CD2 family of the Ig gene superfamily. The natural ligand of LFA-3 is CD2 (also known as "LEA-2") which is expressed on thymocytes, T-cells, B-cells and natural killer ("NK") cells. The gene sequence of human LFA-3 is deposited in GenBank under Accession No. Y00636. The gene sequence of mouse LFA-3 is deposited in GenBank under Accession No. X53526.

Examples of poxvirus strains that are useful in the practice of the present invention include, but are not limited to orthopox viruses, avipox viruses, parapox viruses, yatapox viruses, and molluscipox viruses, but preferably the orthopox and/or avipox viruses. In certain embodiments, the recombinant poxvirus is selected from the group consisting of orthopox viruses, avipox viruses, parapox viruses, yatapox viruses, and molluscipox viruses. In certain embodiments, the recombinant poxvirus is an avipox virus. In certain embodiments, the avipox virus is selected from the group consisting of canarypox virus and fowlpox virus. In certain embodiments, the avipox virus is canarypox virus. In certain embodiments, the avipox virus is fowlpox virus.

In certain embodiments, the recombinant poxvirus is an orthopox virus. In certain embodiments, the orthopox virus is selected from the group consisting of vaccinia virus, cowpox virus, and monkeypox virus. In certain embodiments, the orthopox virus is vaccinia virus. In certain embodiments, the vaccinia virus is selected from the group consisting of wild-type vaccinia virus, vaccinia virus-Western Reserve, vaccinia virus-Copenhagen, Dryvax (also known as vaccinia virus-Wyeth), ACAM2000, and MVA.

Examples of MVA virus strains that are useful in the practice of the present invention and that have been deposited in compliance with the requirements of the Budapest Treaty are strains MVA 572, deposited at the European Collection of Animal Cell Cultures (ECACC), Vaccine Research and Production Laboratory, Public Health Laboratory Service, Centre for Applied Microbiology and Research, Porton Down, Salisbury, Wiltshire SP4 0JG, United Kingdom, under the deposition number ECACC 94012707 on Jan. 27, 1994, and MVA 575, deposited at the European Collection of Animal Cell Cultures (ECACC) under deposition number ECACC 00120707 on Dec. 7, 2000. MVA-BN®, deposited on Aug. 30, 2000, at the European Collection of Animal Cell Cultures (ECACC) under deposition number V00083008, and its derivatives, are additional exemplary strains.

In certain embodiments, the recombinant MVA is MVA-572. In certain embodiments, the recombinant MVA is MVA-575. In certain embodiments, the recombinant MVA is MVA-BN or a derivative thereof.

In certain embodiments, the increased T-cell immune response comprises greater numbers of cytotoxic T-cells (CTLs) specific for the heterologous disease-associated antigen. In certain embodiments, the greater numbers of CTLs specific for the heterologous disease-associated antigen also display increased cytolytic activity compared to CTLs induced by administration of a recombinant MVA comprising a nucleic acid sequence encoding a heterologous disease-associated antigen but not a nucleic acid sequence encoding a flagellin. In certain embodiments, the increased T-cell immune response comprises greater numbers of memory T-cells specific for the heterologous disease-associated antigen. In certain embodiments, the increased T-cell immune response comprises greater numbers of CTLs specific for the heterologous disease-associated antigen and greater numbers of memory T-cells specific for the heterologous disease-associated antigen. In certain embodiments, the greater numbers of CTLs specific for the heterologous disease-associated antigen also display increased cytolytic activity compared to CTLs induced by administration of a recombinant MVA comprising a nucleic acid sequence encoding a heterologous disease-associated antigen but not a nucleic acid sequence encoding a flagellin.

In certain embodiments, the heterologous disease-associated antigen is an infectious disease antigen or a tumor-associated antigen. In certain embodiments, the heterologous disease-associated antigen is a tumor-associated antigen. In certain embodiments, the tumor-associated antigen is selected from the group consisting of 5-α-reductase, α-fetoprotein ("AFP"), AM-1, APC, April, B melanoma antigen gene ("BAGE"), β-catenin, Bcl12, bcr-abl, Brachyury, CA-125, caspase-8 ("CASP-8", also known as "FLICE"), Cathepsins, CD19, CD20, CD21/complement receptor 2 ("CR2"), CD22/BL-CAM, CD23/$F_c\epsilon RII$, CD33, CD35/complement receptor 1 ("CR1"), CD44/PGP-1, CD45/leucocyte common antigen ("LCA"), CD46/membrane cofactor protein ("MCP"), CD52/CAMPATH-1, CD55/decay accelerating factor ("DAF"), CD59/protectin, CDC27, CDK4, carcinoembryonic antigen ("CEA"), c-myc, cyclooxygenase-2 ("cox-2"), deleted in colorectal cancer gene ("DCC"), DcR3, E6/E7, CGFR, EMBP, Dna78, farnesyl transferase, fibroblast growth factor-8a ("FGF8a"), fibroblast growth factor-8b ("FGF8b"), FLK-1/KDR, folic acid receptor, G250, G melanoma antigen gene family ("GAGE-family"), gastrin 17, gastrin-releasing hormone, ganglioside 2 ("GD2")/ganglioside 3 ("GD3")/ganglioside-monosialic acid-2 ("GM2"), gonadotropin releasing hormone ("GnRH"), UDP-GlcNAc:$R_1$Man($\alpha$1-6)$R_2$ [GlcNAc to Man ($\alpha$1-6)] β1,6-N-acetylglucosaminyltransferase V ("GnT V"), GP1, gp100/Pme117, gp-100-in4, gp15, gp75/tyrosine-related protein-1 ("gp75/TRP-1"), human chorionic gonadotropin ("hCG"), heparanase, Her2/neu, human mammary tumor virus ("HMTV"), 70 kiloDalton heat-shock protein ("HSP70"), human telomerase reverse transcriptase ("hTERT"), insulin-like growth factor receptor-1 ("IGFR-1"), interleukin-13 receptor ("IL-13R"), inducible nitric oxide synthase ("iNOS"), Ki67, KIAA0205, K-ras, H-ras, N-ras, KSA, LKLR-FUT, melanoma antigen-encoding family ("MAGE-family", including at least MAGE-1, MAGE-2, MAGE-3, and MAGE-4), mammaglobin, MAP17, Melan-A/melanoma antigen recognized by T-cells-1 ("MART-1"), mesothelin, MIC NB, MT-MMPs, mucin, testes-specific antigen NY-ESO-1, osteonectin, p15, P170/MDR1, p53, p97/melanotransferrin, PAI-1, platelet-derived growth factor ("PDGF"), µPA, PRAME, probasin, progenipoietin, prostate-specific antigen ("PSA"), prostate-specific membrane antigen ("PSMA"), prostatic acid phosphatase ("PAP"), RAGE-1, Rb, RCAS1, SART-1, SSX-family, STAT3, STn, TAG-72, transforming growth factor-alpha ("TGF-α"), transforming growth factor-beta ("TGF-β"), Thymosin-beta-15, tumor necrosis factor-alpha ("TNF-α"), TP1, TRP-2, tyrosinase, vascular endothelial growth factor ("VEGF"), ZAG, p16INK4, and glutathione-S-transferase ("GST"). In certain embodiments, the tumor-associated antigen is brachyury. In certain embodiments, the tumor-associated antigen is PSA. In certain embodiments, the tumor-associated antigen is CEA. In certain embodiments, the tumor-associated antigen is MUC-1. In certain embodiments, the tumor-associated antigen is CEA and MUC-1.

In certain embodiments, the heterologous disease-associated antigen is an infectious disease antigen. In certain embodiments, the infectious disease antigen is a viral antigen, a bacterial antigen, a fungal antigen, or a parasite antigen.

In certain embodiments, the infectious disease antigen is a viral antigen. In certain embodiments, the viral antigen is derived from a virus selected from the group consisting of adenovirus, Arbovirus, Astrovirus, Coronavirus, Coxsackievirus, Crimean-Congo hemorrhagic fever virus, cytomegalovirus ("CMV"), dengue virus, Ebola virus, Epstein-Barr virus ("EBV"), Foot-and-mouth disease virus, Guanarito virus, Hendra virus, herpes simplex virus-type 1 ("HSV-1"), herpes simplex virus-type 2 ("HSV-2"), human herpesvirus-type 6 ("HHV-6"), human herpesvirus-type 8 ("HHV-8"), hepatitis A virus ("HAV"), hepatitis B virus ("HBV"), hepatitis C virus ("HCV"), hepatitis D virus ("HDV"), hepatitis E virus ("HEV"), human immunodeficiency virus ("HIV"), influenza virus, Japanese encephalitis virus, Junin virus, Lassa virus, Machupo virus, Marburg virus, measles virus, human metapneumovirus, Molluscum contagiosum virus, mumps virus, Newcastle disease virus, Nipha virus, Norovirus, Norwalk virus, human papillomavirus ("HPV"), parainfluenza virus, parvovirus, poliovirus, rabies virus, respiratory syncytial virus ("RSV"), rhinovirus, rotavirus, rubella virus, Sabia virus, severe acute respiratory syndrome virus ("SARS"), varicella zoster virus, variola virus, West Nile virus, and yellow fever virus.

In certain embodiments, the infectious disease antigen is a bacterial antigen. In certain embodiments, the bacterial antigen is selected from the group consisting of antigens derived from *Bacillus anthracis, Bordetella pertussis, Borrelia burgdorferi, Brucella abortus, Brucella canis, Brucella melitensis, Brucella suis, Burkholderia mallei, Burkholderia pseudomallei, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diptheriae, Enterococcus faecalis, Enterococcus faecium, Escherichia coli, enterotoxigenic Escherichia coli, enteropathogenic Escherichia coli, Escherichia coli*) 157:H7, *Francisella tularensis, Haemophilus influenza, Helicobacter pylon, Legionella pneumophila, Leptospira interrogans, Listeria monocytogenes, Mycobacterium leprae, Mycobacterium tuberculosis, Mycoplasma pneumoniae, Neisseria gonorrhoeae, Neisseria meningitides, Pseudomonas aeruginosa, Rickettsia rickettsia, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholerae*, and *Yersinia pestis*. In certain embodiments, the bacterial antigen is derived from *Bacillus anthracis*.

In certain embodiments, the infectious disease antigen is a fungal antigen. In certain embodiments, the fungal antigen is selected from the group consisting of antigens derived from *Aspergillus clavatus, Aspergillus flavus, Aspergillus fumigatus, Aspergillus nidulans, Aspergillus niger, Aspergillus terreus, Blastomyces dermatitidis, Candida albicans, Candida dubliniensis, Candida glabrata, Candida parapsilosis, Candida rugosa, Candida tropicalis, Cryptococcus albidus, Cryptococcus gattii, Cryptococcus laurentii, Cryptococcus neoformans, Histoplasma capsulatum, Microsporum canis, Pneumocystis carinii, Pneumocystis jirovecii, Sporothrix schenckii, Stachbotrys chartarum, Tinea barbae, Tinea captitis, Tinea corporis, Tinea cruris, Tinea faciei, Tinea incognito, Tinea nigra, Tinea versicolor, Trichophyton rubrum* and *Trichophyton tonsurans*.

In certain embodiments, the infectious disease antigen is a parasite antigen. In certain embodiments, the parasite antigen is selected from the group consisting of antigens derived from *Anisakis* spp. *Babesia* spp., *Baylisascaris procyonis, Cryptosporidium* spp., *Cyclospora cayetanensis, Diphyllobothrium* spp., *Dracunculus medinensis, Entamoeba histolytica, Giardia duodenalis, Giardia intestinalis, Giardia lamblia, Leishmania* sp., *Plasmodium falciparum, Schistosoma mansoni, Schistosoma haematobium, Schistosoma japonicum, Taenia* spp., *Toxoplasma gondii, Trichinella spiralis*, and *Trypanosoma cruzi*.

Pharmaceutical Compositions

In certain embodiments, any of the immunogenic compositions provided herein further comprise a pharmaceutically-acceptable carrier. In certain embodiments, the immunogenic composition can be formulated in solution in a concentration range of $10^4$ to $10^9$ $TCID_{50}$/ml, $10^5$ to $5 \times 10^8$ $TCID_{50}$/ml, $10^6$ to $10^8$ $TCID_{50}$/ml, or $10^7$ to $10^8$ $TCID_{50}$/ml. A preferred dose for humans comprises between $10^6$ to $10^9$ $TCID_{50}$, including a dose of $10^6$ $TCID_{50}$, $10^7$ $TCID_{50}$, $10^8$ $TCID_{50}$ or $5 \times 10^8$ $TCID_{50}$.

The immunogenic compositions provided herein may generally include one or more pharmaceutically-acceptable and/or approved carriers, additives, antibiotics, preservatives, adjuvants, diluents and/or stabilizers. Such auxiliary substances can be water, saline, glycerol, ethanol, wetting or emulsifying agents, pH buffering substances, or the like. Suitable carriers are typically large, slowly metabolized molecules such as proteins, polysaccharides, polylactic acids, polyglycolic acids, polymeric amino acids, amino acid copolymers, lipid aggregates, or the like.

For the preparation of vaccines, the immunogenic compositions provided herein can be converted into a physiologically acceptable form. This can be done based on experience in the preparation of poxvirus vaccines used for vaccination against smallpox as described by H. Stickl et al., *Dtsch. med. Wschr.* 99:2386-2392 (1974).

For example, purified viruses can be stored at $-80°$ C. with a titer of $5 \times 10^8$ $TCID_{50}$/ml formulated in about 10 mM Tris, 140 mM NaCl pH 7.7. For the preparation of vaccine shots, e.g., $10^2$-$10^8$ or $10^2$-$10^9$ particles of the virus can be lyophilized in 100 ml of phosphate-buffered saline (PBS) in the presence of 2% peptone and 1% human albumin in an ampoule, preferably a glass ampoule. Alternatively, the vaccine shots can be produced by stepwise freeze-drying of the virus in a formulation. This formulation can contain additional additives such as mannitol, dextran, sugar, glycine, lactose or polyvinylpyrrolidone or other aids such as antioxidants or inert gas, stabilizers or recombinant proteins (e.g., human serum albumin) suitable for in vivo administration. The glass ampoule is then sealed and can be stored between $4°$ C. and room temperature for several months. However, as long as no need exists, the ampoule is stored preferably at temperatures below $-20°$ C.

For vaccination or therapy, the lyophilisate can be dissolved in an aqueous solution, preferably physiological saline or Tris buffer, and administered either systemically or locally, i.e., parenteral, subcutaneous, intravenous, intramuscular, intranasal, or any other path of administration known to the skilled practitioner. In a preferred embodiment, the lyophilisate is administered intranasally. The mode of administration, the dose and the number of administrations can be optimized by those skilled in the art in a known manner.

Kits Comprising Immunogenic Compositions

Also provided herein are kits comprising any one or more of the immunogenic compositions disclosed herein. The kits can comprise one or multiple containers or vials of the immunogenic compositions, together with instructions for the administration of the immunogenic compositions to a subject at risk of contracting an infectious disease or having a tumor. In certain embodiments, the subject is a human. The instructions may indicate that the immunogenic composition should be administered to the subject in a single dose, or in multiple (i.e., 2, 3, 4, etc.) doses. In certain embodiments, the instructions indicate that the immunogenic composition should be administered in a first (priming) and one or more subsequent boosting administrations to naïve or non-naïve subjects. Further provided are kits comprising the immunogenic compositions in a first vial or container for a first administration (priming) and in one or more additional vials or containers for one or more subsequent boosting administrations.

Methods and Uses of Recombinant MVA Viruses

Also provided herein are methods of enhancing an antigen-specific immune response to a disease-associated antigen comprising administering any of the immunogenic compositions provided herein to a subject in need thereof, wherein the immunogenic composition induces increased T-cell immune responses specific for the heterologous disease-associated antigen when administered to the subject, as well as any of the immunogenic compositions provided herein for use in methods of immunizing a subject and use of any of the immunogenic compositions provided herein in the preparation of a medicament for immunizing a subject.

Also provided herein is an immunogenic composition comprising a recombinant modified vaccinia virus Ankara (MVA) comprising a nucleic acid sequence encoding a flagellin and a nucleic acid sequence encoding a heterologous disease-associated antigen for use in inducing an increased T-cell and/or B-cell immune responses specific for the heterologous disease-associated antigen when administered to a subject as compared to T-cell and/or B-cell immune responses specific for the heterologous disease-associated antigen induced by administration of a recombinant MVA comprising a nucleic acid sequence encoding a heterologous disease-associated antigen but not a nucleic acid sequence encoding a flagellin.

In certain embodiments, the subject is a mammal. In certain embodiments, the mammal is a rat, rabbit, pig, mouse, or human, and the methods comprise administering a dose of any one or more of the immunogenic compositions provided herein to the subject.

The subject is preferably a human and may be an adult. In certain embodiments, the adult is over the age of 50, 55, 60, 65, 70, 75, 80, or 85 years. In certain embodiments, the subject is less than 5 years, less than 3 years, less than 2 years, less than 15 months, less than 12 months, less than 9 months, less than 6 months, or less than 3 months of age. In certain embodiments, the subject is 0-3 months, 3-6 months, 6-9 months, 9-12 months, 1-2 years, or 2-5 years of age. In certain embodiments, the subject is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75 or more years old.

In certain embodiments, any of the immunogenic compositions provided herein are administered to the subject at a dose of $10^6$ to $10^9$ TCID$_{50}$, at a dose of $10^6$ to $5\times10^8$ TCID$_{50}$, or $10^7$ to $10^8$ TCID$_{50}$. The immunogenic compositions provided herein may also be administered to the subject at a dose of $10^6$, $10^7$ TCID$_{50}$, $10^8$, or $5\times10^8$ TCID$_{50}$. In certain embodiments, any of the immunogenic compositions provided herein are administered to a human subject at a dose of $10^7$ TCID$_{50}$, $10^8$, or $5\times10^8$ TCID$_{50}$.

In certain embodiments, the immunogenic compositions comprise at least two recombinant poxviruses (e.g., MVA), one comprising a nucleic acid encoding flagellin and one comprising a nucleic acid encoding a heterologous disease-associated antigen, wherein the immunogenic composition induces increased T-cell and/or B-cell immune responses specific for the heterologous disease-associated antigen when administered to a human subject.

In certain embodiments, the immunogenic compositions provided herein are administered to the subject in a single dose, or in multiple (i.e., 2, 3, 4, etc.) doses. In certain embodiments, the immunogenic compositions are administered in a first (priming) inoculation and one or more subsequent boosting administrations. In certain embodiments, the first dose comprises $10^7$ to $10^8$ TCID$_{50}$ of the immunogenic composition and the second dose comprises $10^7$ to $10^8$ TCID$_{50}$ of the immunogenic composition.

In certain embodiments, the one or more subsequent boosting administrations comprise the same recombinant poxvirus vector as previously administered and the methods comprise a homologous prime-boost vaccination. In certain embodiments, the one or more subsequent boosting administrations comprise a different recombinant poxvirus vector than previously administered and the methods comprise a heterologous prime-boost vaccination. In certain embodiments, the first poxvirus vector (i.e., the priming vaccination) administered is an orthopox virus vector. In certain embodiments, the orthopox virus vector is an MVA or an MVA-BN. In certain embodiments, the second poxvirus vector (i.e., the one or more boosting vaccinations) administered is an avipox virus. In certain embodiments, the second recombinant poxvirus vector (i.e., the one or more boosting vaccinations) administered is an avipox virus. In certain embodiments, the avipox virus vector is a canary pox virus vector or a fowlpox virus vector. In certain embodiments, the avipox virus vector is a canary pox virus vector. In certain embodiments, the avipox virus vector is a fowlpox virus vector.

In certain embodiments, the one or more subsequent administrations (i.e., the one or more boosting vaccinations) are administered at intervals comprising days, weeks or months after administration of the initial priming vaccination. In certain embodiments, the one or more subsequent administrations of a recombinant poxvirus vector (i.e., the one or more boosting vaccinations) are administered at intervals of 1, 2, 3, 4, 5, 6, 7 or more days after administration of the initial amount of a recombinant poxvirus vector (i.e., the priming vaccination). In certain embodiments, the one or more subsequent administrations of a recombinant poxvirus vector (i.e., the one or more boosting vaccinations) are administered at intervals of 1, 2, 3, 4, 5, 6, 7, 8 or more weeks after administration of the initial amount of a recombinant poxvirus vector (i.e., the priming vaccination). In certain embodiments, the one or more subsequent administrations of a recombinant poxvirus vector (i.e., the one or more boosting vaccinations) are administered at intervals of 1, 2, 3, 4, 5, 6, 7, 8, 9, 10, 11, 12 or more months after administration of the initial priming vaccination. In certain embodiments, the one or more subsequent administrations of a recombinant poxvirus vector (i.e., the one or more boosting vaccinations) are administered at any combination of intervals after administration of the initial priming vaccination (e.g., 1, 2, 3, 4, 5, 6, 7 or more days, 1, 2, 3, 4, 5, 6, 7, 8 or more weeks, or 1, 2, 3, 4, 5, 6, 7, 8, 9, 10, 11, 12 or more months) disclosed herein.

In certain embodiments, the immunogenic compositions can be administered systemically or locally, parenterally, subcutaneously, intravenously, intramuscularly, or intranasally, preferably subcutaneously or intranasally, more preferably intranasally. The immunogenic compositions can also be administered by any other path of administration known to the skilled practitioner.

In a preferred embodiments, provided herein are methods of immunizing a subject, comprising intranasally administering of the immunogenic composition to the subject.

The detailed examples which follow are intended to contribute to a better understanding of the present invention. However, the invention is not limited by the examples. Other embodiments of the invention will be apparent to those skilled in the art from consideration of the specification and practice of the invention disclosed herein.

EXAMPLES

Example 1: Materials and Methods

Mice.

C57BL/6 (H-2b) mice were purchased from Janvier Labs. C57BL/6-Tg (TcraTcrb) 1100MjbJ (OT-I), C57BL/6-Tg (TcraTcrb) 425bnJ (OT-II) and B6.SJL-Ptprca Pepcb/BoyJ (CD45.1) mice were obtained from the University of Zurich and bred to obtain CD45.1$^+$ OT-I and CD45.1$^+$OT-II mice, respectively. NLRC4$^{-/-}$ were also obtained from the University of Zurich. Mice were bred and maintained either in the animal facilities at Bavarian Nordic GmbH or at the University of Zurich according to institutional guidelines.

Virus, Generation of MVA Recombinants.

All recombinant virus vectors used for this study were based on a cloned version of MVA-BN® in a bacterial artificial chromosome (BAC). MVA-BN® was developed by Bavarian Nordic and is deposited at the European Collection of Cell Cultures (ECACC) (V00083008). The generation of MVA recombinants was carried out as described recently (Baur, K., K. Brinkmann, M. Schweneker, J. Patzold, C. Meisinger-Henschel, J. Hermann, R. Steigerwald, P. Chaplin, M. Suter, and J. Hausmann. 2010. Immediate-early expression of a recombinant antigen by modified vaccinia virus ankara breaks the immunodominance of strong vector-specific B8R antigen in acute and memory CD8 T-cell responses. *J Virol.* 84:8743, Lauterbach, H., J. Patzold, R. Kassub, B. Bathke, K. Brinkmann, P. Chaplin, M. Suter, and H. Hochrein. 2013. Genetic Adjuvantation of Recombinant MVA with CD40L Potentiates CD8 T Cell Mediated Immunity. *Front Immunol.* 4:251). Briefly, the sequence of the strong synthetic early late pS promoter comprises 40 nucleotides exactly matching the previously described sequence (Chakrabarti, S., J. R. Sisler, and B. Moss. 1997. Compact, synthetic, vaccinia virus early/late promoter for protein expression. *Biotechniques* 23:1094). The pS promoter was cloned upstream of the open reading frame for chicken OVA. The pHyb promoter was developed and described by Bauer et al (Bauer, K., K. Brinkmann, M. Schweneker, J. Patzold, C. Meisinger-Henschel, J. Hermann, R. Steigerwald, P. Chaplin, M. Suter, and J. Hausmann. 2010. Immediate-early expression of a recombinant antigen by modified vaccinia virus ankara breaks the immunodominance of strong vector-specific B8R antigen in acute and memory CD8 T-cell responses. *J Virol.* 84:8743) and comprises a late element from the promoter directing the expression of the AT1 protein in cowpox virus (Funahashi, S., T. Sato, and H. Shida. 1988. Cloning and characterization of the gene encoding the major protein of the A-type inclusion body of cowpox virus. *J Gen. Virol.* 69 (Pt 1):35, Patel, D. D., C. A. Ray, R. P. Drucker, and D. J. Pickup. 1988. A poxvirus-derived vector that directs high levels of expression of cloned genes in mammalian cells. *Proc. Natl. Acad. Sci U.S.A.* 85:9431) and five tandemly arranged early elements derived from a modified p7.5 promoter (Davison, A. J., and B. Moss. 1989. Structure of vaccinia virus early promoters. *J Mol. Biol.* 210:749). The pHyb promoter was cloned upstream of the open-reading frame for *Salmonella thypimurium* FliC, hereafter referred to as Flagellin. Infectious viruses were reconstituted from BACs by transfecting BAC DNA into BHK-21 cells and superinfecting them with Shope fibroma virus as a helper virus. After three additional passages on primary chicken embryo fibroblasts (CEF), helper virus free MVA-OVA, MVA-OVA-flagellin viruses were obtained. The viruses were referred to as rMVA for MVA-OVA and rMVA-flagellin for MVA-OVA-flagellin. All viruses used in animal experiments were purified twice through a sucrose cushion.

Immunizations.

For intra-nasal immunizations, mice were anaesthetised and immunized with 20 µl volume (10 µl/nostril) by drop-wise instillation containing 3.5×10$^7$ TCID$_{50}$ of the various MVA recombinants. Groups of 5 mice were used and immunized twice on day 0 and day 21. Serum was obtained from day 14 and every 7 days thereafter for antibody titers.

Adoptive Cell Transfer.

CD45.1$^+$ OT-I or CD45.1$^+$ OT-II mice were used as cell donors for adoptive cell transfer into syngeneic recipient animals. Lymphocytes were isolated from spleen and CD8$^+$ and CD4$^+$ T cells were purified using EasySep kits from StemCell Technology according to the manufacturer's protocol. 1×10$^4$ OT-I CD8$^+$ T and 1×10$^5$ OT-II CD4$^+$ T cells were injected intravenously via the retro-orbital vein a day prior to the immunizations.

Cell Isolation (Spleen, Lung, mLN).

Spleen and lung cells were harvested from mice and incubated with collagenase/DNase for 30 minutes at 37° C. Single-cell suspensions were then prepared by mechanically disrupting the organs through a 70-µm filter. Spleen cells were then subjected to red blood cell lysis (Erylysis, Sigma-Aldrich), whereas lung cells were isolated by centrifugation with 44% Percoll. Mesenteric lymph nodes were harvested in RPMI media containing 2% FCS, disrupted mechanically through a 70-µm cell strainer. Mononuclear cells were washed and counted.

MHC I Dextramer Staining and Intracellular Cytokine Staining.

Blood was collected in PBS containing 2% FCS, 0.1% sodium azide and 2.5 U/ml heparin. Peripheral blood mononuclear cells (PBMCs) were prepared by lysing erythrocytes with red blood cell lysis buffer (Erylysis, Sigma-Aldrich), according to the manufacturer's protocol. PBMCs were stained with APC-conjugated MHC class I H-2 kb dextramers loaded with B8$_{20-27}$-peptide (TSYKFESV) or PE-conjugated MHC class I H-2 kb dextramers loaded with OVA$_{257-264}$-peptide (SIINFEKL) according to the manufacturer's protocol (Immudex), for the detection of B8R- and OVA-specific CD8 T cells, followed by anti-CD8α-BV421, CD44-APC-Cy7 and CD4-FITC. All antibodies were purchased from BD Biosciences, eBioscience or BioLegend. For intracellular cytokine staining, spleen and lung cells were incubated with 2.5 µg/ml of MHC class I restricted peptides (B8$_{20-27}$, OVA$_{257-264}$) for 5-6 h at 37° C. in complete RPMI in the presence of 1 µg/ml GolgiPlug (BD Biosciences). Cells were stained as before with anti-CD8α-BV421, CD44-APC-Cy7, CD4-FITC, IFN-γ-PECy7, TNF-α-PE and IL-2-APC. Peptides were purchased from Genscript. Intracellular cytokine staining of IFN-γ and TNF-α were performed after fixation/permeabilization according to the manufacturer's protocol (BD Cytofix/Cytoperm, BD Biosciences). For live/dead discrimination cells were stained before fixation according to the manufacturer's protocol (LIVE/DEAD fixable violet dead cell staining kit, Life Technologies). All cells were acquired using a digital flow cytometer (LSR II, BD Biosciences) and data were analysed with FlowJo software (Tree Star).

ELISA.

For detection of MVA and OVA-specific IgA, the Bronchoalveolar lavage (BAL) fluid was collected by flushing the trachea 3 times with 1 ml of PBS/0.5 mM EDTA with a cannula. The BAL fluid was then centrifuged to pellet the cells from the BAL fluid, and collected for ELISA. Intestinal washes were collected by flushing the distal part of the small intestine with 1 ml of PBS containing trypsin inhibitor, 50 mM EDTA and 0.1% BSA. The solution was spun at 4000 g for 15 mns at 4° C. ELISAs were performed by coating 96-well plates with 5 μg/ml OVA or MVA, followed by blocking with PBS containing 5% FCS/0.05% Tween20. After incubation of sera, BAL fluid or intestinal washes, IgG, IgG1, IgG2c and IgA were detected using HRP-conjugated antibodies, followed by TMB substrate. Absorbance was measured at 450 nm.

Cytokine Assay-Luminex.

BAL fluid and harvested supernatants were measured for cytokines using the Luminex according to the manufacturer's protocol. TLR5 stimulation using Hek-blue hTLR5 cells. In order to study TLR5 stimulation by rMVA-flagellin, Hek-blue hTLR5 cells were used (Invivogen). Briefly, cells were infected with rMVA or rMVA-flagellin at MOI2 for 18 hours and the supernatant was collected. Recombinant flagellin was used as positive control. Levels of SEAP (secreted embryonic alkaline phosphatase), induced following stimulation of TLR5, can be detected with Hek-Blue detection medium, according to the manufacturer's protocol.

In Vitro Generation of FLDC.

FL BM culture-derived DCs (FLDCs) were prepared as described previously. In vitro-generated FL-dependent DC (FL-DC) were generated and sorted). In short, BM cells were cultured in the presence of human recombinant FL for 8 days.

Sorting of Mucosal DC.

DC subsets from lamina propria FL-treated mice were pooled and sorted. In brief, mice were treated once with human FL and lamina propria cells were collected after 8 days. Dead cells were excluded by propidium iodide staining. Non-DC lineage cells were gated out on the expression of CD19. Lamina propria cDC populations were sorted based on the expression of CD11c, MHC-II, CD11 b, CD103, and CD172a expression. Cell sorting was performed on a FACS Aria instrument (BD).

Example 2: Enhanced CD8+ T Cell Responses in Spleen and Lungs After i.n. rMVA-Flagellin Immunization Intra-nasal immunization is known to induce both systemic and mucosal immune responses. Therefore, we wanted to assess CD8+ T cell responses at both sites following i.n. rMVA immunization. More specifically, we wanted to know if we could obtain better CD8+ T cell responses with our adjuvanted rMVA-flagellin construct compared to rMVA. For this purpose, MHC-I (H2-kb) dextramers loaded with either $B8_{20-27}$ or $OVA_{257-264}$-peptides were used to detect MVA and OVA-specific responses, respectively. $B8_{20-27}$ and $OVA_{257-264}$ are the immune-dominant CD8 T cell epitopes in C57BL/6 mice.

Our data clearly shows enhanced OVA-specific CTL responses following i.n. rMVA-flagellin immunization compared to rMVA, both in spleen and lungs, at day 35, two weeks after the boost. In the spleen, 4% (+/−0.6) of OVA-specific CTL compared to 1.6 (+/−0.2) were observed in rMVA-flagellin and rMVA-immunized mice respectively (FIG. 1a), representing a 2.5-fold increase. Similarly, in the lungs, 15.8% (+/−1.1) and 7.6% (+/−1.6) of OVA-specific CTL were observed (FIG. 1c) after rMVA-flagellin and rMVA-immunized mice, respectively, also representing a 2-fold increase. This could also been shown in terms of absolute numbers of OVA-specific CTL in both organs. In the spleen, 265000 (+/−45000) compared to 120000(+/−15000) OVA-specific CTLs/spleen were observed (FIG. 1b) in i.n. rMVA-flagellin and rMVA-immunized mice respectively. Similarly, 273000 (+/−44000) and 90000 (+/−14000) OVA-specific CTLs/lung was observed in rMVA-flagellin and rMVA-immunized mice respectively (FIG. 1d).

rMVA-specific CTL responses were also measured in both organs and, in contrast to the enhanced OVA-specific CTL responses observed in rMVA-flagellin-immunized mice, there was no siginificant increase in the frequency of B8-specific CTL between rMVA and rMVA-flagellin-immunized mice in the spleen (FIG. 1e) or the lung (FIG. 1f). It is of importance to mention that better CTL responses specific to the transgene are obtained, together with a higher difference compared to our stand-alone rMVA, than that of MVA-specific CTL, which is what we are aiming for.

When the kinetic of OVA-specific CTLs was followed in the blood during the course of immunization, one could clearly see the adjuvant effect of the i.n. administered rMVA-flagellin construct compared to rMVA (FIG. 2). Indeed, at day 28, one week after the boost, there were 4.5% (+/−0.5) and 3.2% (+/−0.4) of OVA-specific CTL in rMVA-flagellin and rMVA immunized mice, respectively (FIG. 2a). Similarly, as the findings described above, there was no increase in the frequency of MVA-specific blood CTL between i.n. rMVA (13.85%+/−1.7) and rMVA-flagellin-immunized mice (9.8%+/−1.7). In addition, 7 days following the first immunization, no difference in the frequency of both MVA and OVA-specific CTLs could be observed, between rMVA-flagellin and rMVA-immunized mice (FIGS. 2a, b). This suggests that the adjuvant effect of MVA-encoded flagellin is more pronounced after the second than after the first immunization.

Together this data clearly illustrates that i.n. rMVA-flagellin immunization induces an enhanced CD8+ T cell response compared to rMVA. This increased CTL response occurs both systemically, in the spleen and blood and in the mucosal compartment, the lung.

Example 3: Increased Frequency of Cytokine-Producing CTL in the Spleen of i.n. rMVA-Flagellin Immunized Mice Having established an enhanced frequency of antigen-specific CD8+ T cells after i.n. rMVA-flagellin immunization by MHC I multimer staining, we wanted to address the frequency of cytokine-producing memory CD8+ T cells, which are known to rapidly produce cytokines such as IFN-γ, TNF-α. MVA and OVA-specific CD8+ T cells were measured by intracellular cytokine staining, following in vitro restimulation with both B8 and OVA peptides.

In the spleen, we could also observe an increase in the frequency of cytokine-producing OVA-specific CD8+ T cells after rMVA-flagellin immunization (FIG. 3). Indeed 3.5% (+/−0.2) of IFN-γ+ (FIG. 3a), 3.2% (+/−0.2) of TNF-α+ (FIG. 3c) OVA-specific CD8+ T cells were observed in rMVA-flagellin immunized mice, compared to 1.3% (+/−0.2) (FIG. 3a), 1.2% (+/−0.1) (FIG. 3c) of IFN-γ+, TNF-α+ OVA-specific CD8+ T cells in mice immunized with rMVA, representing a 2.5, and 2.7-fold increase, respectively. This could also been shown in terms of absolute numbers (data not shown). In contrast, there was no significant difference in the frequency of cytokine producing B8-specific CD8+ T cells between rMVA and rMVA-flagellin-immunized mice. 7.7% (+/−1.7) of IFN-γ+ (FIG. 3b), 6.3% (+/−0.9) of TNF- α+ (FIG. 3d) B8-specific CD8+ T cells were observed in rMVA-flagellin immunized mice, compared to 6% (+/−0.6) (FIG. 3b), 4.6% (+/−04) (FIG. 3d) of IFN-γ+, TNF-α+ B8-specific CD8+ T cells in mice immunized with rMVA.

Altogether, these data demonstrate that the use of our TLR5L-adjuvanted MVA, administered intra-nasally, has the capacity to improve the frequency of cytokine-producing memory CTL, compared to rMVA administered via the same route. In addition, this enhanced antigen-specific immune response occurs both systemically and at the site of immunization.

Example 4: i.n. rMVA Flagellin Immunization Induces a Qualitative Improvement in Antigen-Specific CTL Responses Having established the beneficial effect of rMVA-flagellin after i.n. administration in enhancing the frequency of both cytokine-producing MVA and OVA-specific CTLs, we wanted to determine the quality of the response.

Our results show that in the spleen, there is a tendency of a higher IFN-γ (FIG. 4a), TNF-α (FIG. 4b) production from antigen-specific CD8+ T cells, on a per cell basis, in rMVA-flagellin immunized mice compared to rMVA-immunized mice. Indeed, IFN-γ+ OVA-specific CTL expressed a GMFI of 1900 (+/−86) and 1570 (+/−43) in rMVA-flagellin and rMVA-immunized mice respectively (FIG. 4a). Similarly an enhanced GMFI of TNF-α+ OVA-specific CTL were observed in rMVA-flagellin and rMVA-immunized mice with a GMFI of 5850 (+/−290) and 4700 (+/−130) respectively (FIG. 4b).

This data therefore further confirms the advantage i.n. rMVA-flagellin administration in enhancing the quantity and quality of the memory CTL response.

Example 5: i.n. Administration of rMVA-Flagellin Induces Stronger Serum Antibody Responses Than rMVA From the above results, we can clearly show the advantage of using our TLR5L-adjuvanted MVA vaccine via the i.n. route, for a stronger CD8+ T cell response, both quantitatively and qualitatively. Nevertheless, when designing a new vaccine, it is of ultimate importance, in order to achieve long-term immunity, to also obtain efficient antibody responses. Therefore, the contribution of rMVA-flagellin, in our i.n. model, to promote antibody responses was determined. One essential question was whether better serum antibody responses could be obtained with rMVA-flagellin compared to rMVA.

Therefore, we sought out to measure the levels of MVA- and OVA-specific IgG in the serum of mice at day 35, 2 weeks after the boost. Our data shows that there was no significant difference in the levels of MVA and OVA-specific IgG in rMVA-flagellin immunized mice compared to that in rMVA-immunized mice (FIG. 5a). Even though it appeared that rMVA-flagellin-immunized did not exhibit enhanced serum IgG responses, and in order to get a better insight into the type of immune response generated following i.n. administration of rMVA-flagellin, we set out to characterize the specific IgG isotype response. IgG1 indicates a bias towards a Th2-type immune response, whereas IgG2c would suggest a bias towards a Th1-type immune response. Whereas there was no significant difference in the serum levels of both MVA (FIG. 5b) and OVA-specific (FIG. 5c) IgG1 between rMVA and rMVA-immunized mice, enhanced serum MVA (FIG. 5b) and OVA-specific (FIG. 5c) IgG2c titers were observed in rMVA-flagellin-immunized mice compared to rMVA-immunized mice, suggesting an enhanced Th1 response.

If we look in closer details at the antigen-specific antibody isotype responses, one can clearly notice that, in rMVA-immunized mice, there is a bias towards a Th2-type immune response with higher serum IgG1 titers compared to IgG2c (FIG. 5c). In contrast, rMVA-flagellin-immunized mice exhibited a mixed Th1 and Th2 immune responses with marginally enhanced IgG1 titers compared to IgG2c titers in the serum (FIG. 5c).

Altogether, this data shows that i.n. rMVA immunization can induce serum antibody responses with rMVA-flagellin immunization being better at inducing a Th1 immune response compared to rMVA alone.

Example 6: Induction of IgG and IgA Responses in the BAL after i.n. Immunization Having established the development of antibody responses in the serum of rMVA and rMVA-flagellin-immunized mice, and enhanced serum IgG2c titers after i.n. rMVA-flagellin immunization, we were interested to determine if similar responses could be observed locally at the site of immunization, in the BAL. Indeed, a similar response in terms of IgG responses in the BAL can be observed (FIG. 6). No difference in total BAL IgG could be between rMVA and rMVA-flagellin-immunized mice (FIG. 6a). In addition, as observed in the serum, similar levels of rMVA-specific (FIG. 6b) and OVA-specific (FIG. 6c) IgG1 titers could be detected in the BAL of rMVA and rMVA-flagellin-immunized mice. In contrast, with regard to IgG2c titers, rMVA-flagellin immunized mice exhibited both enhanced rMVA (FIG. 6b), and OVA-specific (FIG. 6c) IgG2c titers compared to rMVA-immunized mice. Furthermore, rMVA-immunized exhibited a more pronounced antigen-specific Th2 immune response in the BAL, with higher levels of IgG1 titers compared to IgG2c (FIG. 6c), whereas a mixed Th1 and Th2 immune response could also be seen in the BAL rMVA-flagellin-immunized mice (FIG. 6c), as observed in the serum. This suggests that rMVA-flagellin immunization also induces a more balanced immune response at the site of mucosal immunization.

The hallmark of mucosal immunity is the production of local IgA at mucosal sites. Therefore, it was of high importance to assess the presence of IgA in the BAL of rMVA-flagellin immunized mice and compare such response to that of i.n. rMVA-immunized mice. Our results show that both i.n. rMVA and rMVA-flagellin immunization can induce OVA-specific IgA responses in the BAL (FIG. 6d), suggesting the development of mucosal immunity in the lung. Nevertheless, similar levels of OVA-specific IgA titers were obtained between rMVA and rMVA-flagellin i.n. immunizations (FIG. 6e). This suggests that i.n. administration of rMVA can certainly induce IgA antibody responses in the lung, independent of the use of our adjuvanted rMVA.

These findings confirm the advantage of rMVA vaccines administered via the i.n. route, in eliciting strong systemic and mucosal immunity, specifically IgA production at mucosal surfaces, which establishes it as a very good candidate for a mucosal vaccine.

Example 7: Migration of Adoptively Transferred Cells Into the Mesenteric Lymph Node (mLN) After i.n. rMVA Immunization In recent years intensive effort has been made in order to develop mucosal vaccines, and i.n. immunization has proved a very attractive route for many various reasons, as previously mentioned. Furthermore, i.n. immunization has been described to not only elicit strong upper-respiratory tract immunity but also gastro-intestinal immune responses. Therefore we wanted to establish if rMVA and rMVA-flagellin administered via the i.n. could also induce immune responses in the gastro-intestinal tract. If one can induce immunity in the GI-tract, this would definitely open new opportunities in the development of mucosal rMVA vaccines specific for gastro-intestinal pathogens.

Therefore, we first set out to investigate the homing of T cells in the mLN, 7 days following i.n. immunization with rMVA and rMVA-flagellin. Mice were adoptively transferred with a mixture of OVA-specific CD8$^+$ T and CD4$^+$ T cells from CD45.1$^+$ OT-I and CD45.1$^+$OT-II mice respectively, and immunized with rMVA-flagellin or rMVA intranasally. 7 days later, mice were sacrificed and the frequency of CD45.1$^+$CD8$^+$ and CD45.1$^+$CD4$^+$ T cells was determined. Our results clearly show that, 7 days after both i.n. rMVA and rMVA-flagellin immunization, homing of CD8$^+$ and CD4$^+$ T cells could be observed in the mLN suggesting that induction of a gastro-intestinal immune response had occurred. Indeed 1.7% and 2% of transferred OT-I-CD8$^+$ T cells from rMVA and rMVA-flagellin immunized mice respectively, were observed in the mLN (FIG. 7a). This CD8$^+$ T cells homing to the mLN could also be shown in terms of absolute numbers (FIG. 7b). Similar responses could be observed with regard to the homing of CD4$^+$ T cells. Indeed, 0.5% of transferred OT-II-CD4$^+$ T cells were observed in the mLN of both i.n. rMVA and rMVA-flagellin-immunized mice (FIGS. 7c, d). Even though we could not observe any difference in homing of CD8+ and CD4$^+$ T cells between rMVA and rMVA-flagellin immunized mice at day 7, this data strongly suggest that i.n. administration can induce the development of gastro-intestinal immune responses.

This is the first finding showing that i.n. administration of our both rMVA and adjuvanted MVA can indeed induce immune responses all the way to the gastro-intestinal tract.

Example 8: Intestinal IgA After i.n. rMVA Immunization

Having previously shown the migration of adoptively transferred T cells to the mLN following i.n. rMVA and rMVA-flagellin immunization indicating the induction of a gastro-intestinal immune response, together with the induction of IgA in the BAL of rMVA-flagellin immunized mice, we wanted to determine if IgA could also be detected in the lamina propria of immunized mice, which would indeed confirm the establishment of gastro-intestinal immunity.

OVA-specific IgA from intestinal washes of rMVA-flagellin and rMVA i.n.-immunized mice were analysed at day 35. Our results clearly show the presence of intestinal IgA in the lamina propria of both i.n. immunized mice (FIG. 8). As previously observed in the BAL, there also seems to be no significant difference in OVA-specific IgA titers between rMVA and rMVA-flagellin-immunized mice. The presence of intestinal IgA in the lamina propria of rMVA i.n. immunized correlates nicely with all the data described so far, with the induction of immune responses in the mLN. In light of these findings, we can strongly confirm that, gastro-intestinal immunity has been induced following an i.n. route of immunization using our recombinant MVA vaccine. This opens a new avenue for the development of potential rMVA mucosal vaccines for gastro-intestinal pathogens.

Example 9: In Vivo Innate Cytokine Responses in the BAL Following i.n. rMVA-Flagellin Immunization Having established that i.n. rMVA-flagellin induces enhanced systemic and mucosal immunity compared to rMVA, we wanted to determine the in vivo innate immune response after i.n. rMVA-flagellin immunization. Therefore, BAL fluid of mice from i.n. rMVA-flagellin immunized mice was collected and analysed for cytokine production 24 hrs following immunization.

Our results show production of IL-1β (FIG. 9a), IL-18 (FIG. 9b), TNF-α (FIG. 9c) and CXCL1 (FIG. 9d) in the BAL fluid of rMVA-flagellin immunized 24 hours after immunization. The production of IL-1β and IL-18 confirms the specific flagellin innate immune sensing by the NLRC4 inflammasome pathway. This was further confirmed with the strong reduction of IL-1β and IL-18 in the BAL of NLCR4$^{-/-}$ i.n. rMVA-flagellin-immunized mice, compared to wild-type i.n. rMVA-flagellin immunized mice (FIGS. 9e, f). TNF-α production is the result of TLR-5 innate immune recognition by APCs. IL-18 production can also be detected after rMVA immunization (FIG. 9b), which is expected as a result of the innate immune sensing of MVA by the NLRP2 inflammasome.

Altogether, the above results indicate that the innate immune sensing of rMVA-flagellin in vivo occurs in a TLR5 and NLCR4 inflammasome-dependent manner with the production of TNF-α and IL1-β/IL-18, respectively. These results corroborate with the flagellin adjuvant specificity, observed in previous studies, and confirm the capacity of our genetically encoded-flagellin rMVA vaccine to induce strong innate immune responses, after i.n. administration, compared to rMVA.

Example 10: Recognition of rMVA-Flagellin by TLR5

Having previously shown, from the above results, that rMVA-flagellin can trigger the activation of the TLR5 pathway with the secretion of TNF-α we wanted to investigate further the mechanism of recognition of rMVA-flagellin via TLR5. Indeed flagellin encoded in the rMVA-flagellin construct does not contain a eukaryotic secretion signal, therefore it is of interest to determine whether the flagellin remains intracellular after transduction or is secreted. Using the HEK-blue hTLR5 reporter cell line, we were able to show that rMVA-flagellin-transduced Hela cells can trigger the activation of TLR5 (FIG. 10). In addition, HEK-Blue cells incubated with supernatant or cell lysates from rMVA-flagellin transduced cells also showed SEAP activity, suggesting that flagellin is secreted or released from rMVA-flagellin transduced cells, and accumulates within the transduced cells respectively (FIG. 10). As expected, rMVA cannot trigger activation of TLR5, as no SEAP activity could be detected. Similarly, we also showed that supernatant from cells transduced with rMVA alone does no stimulate TLR5, as no SEAP activity could be measured in this assay (FIG. 10). Using recombinant flagellin as a positive control, we confirmed that the flagellin protein did indeed stimulate the HEK-blue cells (FIG. 10). It is of interest to mention that even though supernatant from rMVA-flagellin transduced cells trigger TLR5 activation, strongly suggesting that flagellin is being secreted, it does not exclude the potential release of flagellin from dying transduced cells, following pyroptosis, which has already been observed in the above results (FIG. 10).

Example 11: rMVA-Flagellin Induces TLR5 and Inflammasome-Dependent Cytokine Responses by DCs In Vitro In order to improve the immunogenicity of our classical rMVA vaccine, we designed a genetically adjuvanted construct with the well-established mucosal adjuvant flagellin, with the aim to use our vaccine via a mucosal route. Prior to in vivo administration, it was important to determine the bioactivitiy and the innate immune sensing capacity with in vitro studies using FLDCs.

Flagellin recognition is known to be mediated by two mechanisms. Extracellular sensing of flagellin signals by TLR5, whereas intracytoplasmic sensing of flagellin signals via the NAIP5/NLRC4 inflammasome. These two distinct recognition pathways lead to the production of specific innate cytokine such as IL-6 and TNF-α in response to TLR5 signalling, and IL-1β together with IL-18, following inflammasome-mediated caspase-1 activation. Therefore we wanted to know whether our adjuvanted rMVA-flagellin had the capacity to trigger the production of the above specific cytokines, triggering either the TLR5 or the inflammasome pathway or both simultaneously. In order to address this question, FLDCs were stimulated with rMVA, rMVA-flagellin, rMVA and flagellin, or recombinant flagellin alone for 6 hours (FIG. 11). The supernatant was then analysed for cytokines. Our results clearly show that rMVA-flagellin does indeed stimulate an inflammasome-dependent recognition pathway with the production of both IL-1ββ (FIG. 11a) and IL-18 (FIG. 11b), observed. IL-1β was specific to rMVA-flagellin, as neither rMVA nor the recombinant flagellin induced IL-1β production from FLDC. However using recombinant flagellin with a transfection reagent to stimulate DC, lead to some IL1-β production, albeit at much lower levels than rMVA-flagellin (FIG. 11a). In contrast, IL-18 could be observed from both rMVA and rMVA+flagellin-stimulated FLDC, also at a much lower levels compared to rMVA-flagellin (FIG. 11b), also suggesting activation of the inflammasome pathway by the later. FLDC stimulated with recombinant flagellin alone did not induce IL-18 production (FIG. 11b). IL-6 (FIG. 11c) and TNF-α (FIG. 11d) could also be detected as early as 6 hours from rMVA-flagellin stimulated FLDC, which confirms an activation of the TLR5 pathway. In addition, rMVA+flagellin-stimulated DC induced IL6 and TNF-α to levels approximately than that of rMVA-flagellin-stimulated DC 6 hours after infection (FIGS. 11c, d), which shows the effect of the added flagellin and stimulation of TLR5, whereas rMVA-stimulated DC induced marginal levels of both IL-6 and TNF-α compared to rMVA-flagellin stimulated DC. Altogether these results suggest that rMVA-flagellin recognition triggers both the TLR5 and the NLCR4 inflammasome pathways in DC in a time-dependent manner with highest cytokine production as early as 6 hours after stimulation.

Example 12: rMVA-Flagellin-Specific IL-1β Production From Mucosal Dendritic Cells Having established in vivo and in vitro rMVA-flagellin-specific IL-1β production, together with the development of gastro-intestinal immune responses following i.n. rMVA-flagellin immunization, we wanted to determine if it would be possible to induce stimulation of mucosal DC, more specifically DC from the lamina propria.

There are 3 major subsets of conventional DC which have been described in the lamina propria on the basis of CD11b, CD172a and CD103. The CD11b⁻CD172a⁻CD103⁺ represent the counterparts of the $CD8_\alpha^+$ DC found in lymphoid organs. CD11b⁺CD172a⁺CD103⁻ DC have been described to respond to flagellin, therefore it was of interest to determine if rMVA-flagellin would have the capacity to stimulated this particular mucosal DC subset. Indeed, our results show that when this subset of mucosal DC was sorted and ex vivo stimulated with rMVA-flagellin, IL-1β could be observed (FIG. 12). This data therefore suggest that rMVA-flagellin can stimulate mucosal DC.

Sequences

```
SEQ ID NO: 1 (amino acid sequence of P06179 (UniProt) Flagellin
(Salmonella typhimurium):
MAQVINTNSLSLLTQNNLNKSQSALGTAIERLSSGLRINSAKDDAAGQAIANRFTANIKG

LTQASRNANDGISIAQTTEGALNEINNNLQRVRELAVQSANSTNSQSDLDSIQAEITQRL

NEIDRVSGQTQFNGVKVLAQDNTLTIQVGANDGETIDIDLKQINSQTLGLDTLNVQQKYK

VSDTAATVTGYADTTIALDNSTFKASATGLGGTDQKIDGDLKFDDTTGKYYAKVTVTGG

TGKDGYYEVSVDKTNGEVTLAGGATSPLTGGLPATATEDVKNVQVANADLTEAKAALT

AAGVTGTASVVKMSYTDNNGKTIDGGLAVKVGDDYYSATQNKDGSISINTTKYTADDG

TSKTALNKLGGADGKTEVVSIGGKTYAASKAEGHNFKAQPDLAEAAATTTENPLQKIDA

ALAQVDTLRSDLGAVQNRFNSAITNLGNTVNNLTSARSRIEDSDYATEVSNMSRAQILQ

QAGTSVLAQANQVPQNVLSLLR

SEQ ID NO: 2 (DNA coding sequence of flagellin (P06179) NCBI Reference
Sequence NC_003197.1:
atggcacaag tcattaatac aaacagcctg tcgctgttga cccagaataa cctgaacaaa tcccagtccg ctctgggcac cgctatcgag cgtctgtctt ccggtctgcg tatcaacagc gcgaaagacg atgcggcagg tcaggcgatt gctaaccgtt ttaccgcgaa catcaaaggt ctgactcagg cttcccgtaa cgctaacgac ggtatctcca ttgcgcagac cactgaaggc gcgctgaacg aaatcaacaa caacctgcag cgtgtgcgtg
```

-continued

```
aactggcggt tcagtctgct aacagcacca actcccagtc tgacctcgac tccatccagg ctgaaatcac ccagcgcctg aacgaaatcg accgtgtatc cggccagact cagttcaacg gcgtgaaagt cctggcgcag gacaacaccc tgaccatcca ggttggtgcc aacgacggtg aaactatcga tatcgatctg aagcagatca actctcagac cctgggtctg gatacgctga atgtgcaaca aaaatataag gtcagcgata cggctgcaac tgttacagga tatgccgata ctacgattgc tttagacaat agtacttta aagcctcggc tactggtctt ggtggtactg accagaaaat tgatggcgat ttaaaatttg atgatacgac tggaaaatat tacgccaaag ttaccgttac gggggggaact ggtaaagatg gctattatga agtttccgtt gataagacga acggtgaggt gactcttgct ggcggtgcga cttccccgct tacaggtgga ctacctgcga cagcaactga ggatgtgaaa aatgtacaag ttgcaaatgc tgatttgaca gaggctaaag ccgcattgac agcagcaggt gttaccggca cagcatctgt tgttaagatg tcttatactg ataataacgg taaaactatt gatggtggtt tagcagttaa ggtaggcgat gattactatt ctgcaactca aaataaagat ggttccataa gtattaatac tacgaaatac actgcagatg acgtacatc caaaactgca ctaaacaaac tgggtggcgc agacggcaaa accgaagttg tttctattgg tggtaaaact tacgctgcaa gtaaagccga aggtcacaac tttaaagcac agcctgatct ggcggaagcg gctgctacaa ccaccgaaaa cccgctgcag aaaattgatg ctgctttggc acaggttgac acgttacgtt ctgacctggg tgcgtacag aaccgtttca actccgctat taccaacctg ggcaacaccg taaacaacct gacttctgcc cgtagccgta tcgaagattc cgactacgcg accgaagttt ccaacatgtc tcgcgcgcag attctgcagc aggccggtac ctccgttctg gcgcaggcga accaggttcc gcaaaacgtc ctctctttac tgcgttaa
```

SEQ ID NO: 3 (B8₂₀₋₂₇-Peptide):
TSYKFESV

SEQ ID NO: 4 (OVA₂₅₇₋₂₆₄-peptide):
SIINFEKL

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

---

The invention claimed is:

1. An immunogenic composition comprising a recombinant modified vaccinia virus Ankara (MVA) comprising a nucleic acid sequence encoding a flagellin and further comprising a nucleic acid sequence encoding a heterologous disease-associated antigen, wherein the immunogenic composition induces: a) increased T-cell and/or B-cell immune responses specific for the heterologous disease-associated antigen, and b) increased innate immune responses when administered to a subject as compared to T-cell and/or B-cell immune responses specific for the heterologous disease-associated antigen and innate immune responses induced by administration of a recombinant MVA comprising a nucleic acid sequence encoding a heterologous disease-associated antigen but not a nucleic acid sequence encoding a flagellin; wherein said recombinant modified vaccinia virus Ankara (MVA) is capable of reproductive replication in chicken embryo fibroblasts.

2. The immunogenic composition of claim 1, wherein the increased T-cell immune response comprises greater numbers of cytotoxic T-cells (CTLs) specific for the heterologous disease-associated antigen.

3. The immunogenic composition of claim 1, wherein the nucleic acid sequence encodes a flagellin having at least 95% amino acid sequence identity to SEQ ID NO:1.

4. The immunogenic composition of claim 3, wherein the nucleic acid sequence encodes a flagellin having the amino acid sequence of SEQ ID NO:1.

5. The immunogenic composition of claim 1, further comprising a pharmaceutically acceptable carrier.

6. The immunogenic composition of claim 1, wherein the disease-associated antigen is an infectious disease antigen or a tumor-associated antigen.

7. The immunogenic composition of claim 6, wherein the disease-associated antigen is an infectious disease antigen selected from a viral antigen, a bacterial antigen, a fungal antigen, and a parasite antigen.

8. The immunogenic composition of claim 7, wherein the infectious disease antigen is a viral antigen.

9. The immunogenic composition of claim 8, wherein the viral antigen is derived from a virus selected from the group consisting of adenovirus, Arbovirus, Astrovirus, Coronavirus, Coxsackievirus, Crimean-Congo hemorrhagic fever virus, cytomegalovirus (CMV), dengue virus, Ebola virus, Epstein-Barr virus (EBV), Foot-and-mouth disease virus, Guanarito virus, Hendra virus, herpes simplex virus-type 1 (HSV-1), herpes simplex virus-type 2 (HSV-2), human herpesvirus-type 6 (HHV-6), human herpesvirus-type 8 (HHV-8), hepatitis A virus (HAV), hepatitis B virus (HBV), hepatitis C virus (HCV), hepatitis D virus (HDV), hepatitis E virus (HEV), human immunodeficiency virus (HIV), influenza virus, Japanese encephalitis virus, Junin virus, Lassa virus, Machupo virus, Marburg virus, measles virus, human metapneumovirus, Molluscum contagiosum virus, mumps virus, Newcastle disease virus, Nipha virus, Norovirus, Norwalk virus, human papillomavirus (HPV), parainfluenza virus, parvovirus, poliovirus, rabies virus, respiratory syncytial virus (RSV), rhinovirus, rotavirus, rubella virus, Sabia virus, severe acute respiratory syndrome virus (SARS), varicella zoster virus, variola virus, West Nile virus, and yellow fever virus.

10. A method of inducing an antigen-specific immune response to a disease-associated antigen in a subject comprising administering to the subject an immunogenic composition comprising a nucleic acid sequence encoding a flagellin and further comprising a nucleic acid sequence encoding a heterologous disease-associated antigen, wherein the immunogenic composition induces: a) increased T-cell and/or B-cell immune responses specific for the heterologous disease-associated antigen, and b) increased innate immune responses as compared to T-cell and/or B-cell immune responses specific for the heterologous disease-associated antigen and innate immune responses induced by administration of a recombinant MVA comprising a nucleic acid sequence encoding a heterologous disease-associated antigen but not a nucleic acid sequence encoding a flagellin; wherein said recombinant modified vaccinia virus Ankara (MVA) is capable of reproductive replication in chicken embryo fibroblasts.

11. The method of claim 10, wherein the increased T-cell immune response comprises greater numbers of cytotoxic T-cells (CTLs) specific for the heterologous disease-associated antigen.

12. The method of claim 10, wherein the nucleic acid sequence encodes a flagellin having at least 95% amino acid sequence identity to SEQ ID NO:1.

13. The method of claim 12, wherein the nucleic acid sequence encodes a flagellin having the amino acid sequence of SEQ ID NO:1.

14. The method of claim 10, wherein the disease-associated antigen is an infectious disease antigen or a tumor-associated antigen.

15. The method of claim 14, wherein the disease-associated antigen is an infectious disease antigen selected from a viral antigen, a bacterial antigen, a fungal antigen, and a parasite antigen.

16. The method of claim 15, wherein the infectious disease antigen is a viral antigen.

17. The method of claim 16, wherein the viral antigen is derived from a virus selected from the group consisting of adenovirus, Arbovirus, Astrovirus, Coronavirus, Coxsackievirus, Crimean-Congo hemorrhagic fever virus, cytomegalovirus (CMV), dengue virus, Ebola virus, Epstein-Barr virus (EBV), Foot-and-mouth disease virus, Guanarito virus, Hendra virus, herpes simplex virus-type 1 (HSV-1), herpes simplex virus-type 2 (HSV-2), human herpesvirus-type 6 (HHV-6), human herpesvirus-type 8 (HHV-8), hepatitis A virus (HAV), hepatitis B virus (HBV), hepatitis C virus (HCV), hepatitis D virus (HDV), hepatitis E virus (HEV), human immunodeficiency virus (HIV), influenza virus, Japanese encephalitis virus, Junin virus, Lassa virus, Machupo virus, Marburg virus, measles virus, human metapneumovirus, Molluscum contagiosum virus, mumps virus, Newcastle disease virus, Nipha virus, Norovirus, Norwalk virus, human papillomavirus HPV), parainfluenza virus, parvovirus, poliovirus, rabies virus, respiratory syncytial virus (RSV), rhinovirus, rotavirus, rubella virus, Sabia virus, severe acute respiratory syndrome virus (SARS), varicella zoster virus, variola virus, West Nile virus, and yellow fever virus.

18. The method of claim 15, wherein the infectious disease antigen is a bacterial antigen.

19. The method of claim 18, wherein the bacterial antigen is derived from a bacterium selected from the group consisting of *Bacillus anthracis, Bordetella pertussis, Borrelia burgdorferi; Brucella abortus, Brucella canis, Brucella melitensis, Brucella suis, Burkholderia mallei, Burkholderia pseudomallei, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diptheriae, Enterococcus faecalis, Enterococcus faecium, Escherichia coli, Francisella tularensis, Haemophilus influenza, Helicobacter pylori, Legionella pneumophila, Leptospira*

*interrogans, Listeria monocytogenes, Mycobacterium leprae, Mycobacterium tuberculosis, Mycoplasma pneumoniae, Neisseria gonorrhoeae, Neisseria meningitides, Pseudomonas aeruginosa, Rickettsia rickettsia, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholerae*, and *Yersinia pestis*.

20. The method of claim 15, wherein the fungal antigen is derived from a fungus selected from the group consisting of *Aspergillus clavatus, Aspergillus flavus, Aspergillus fumigatus, Aspergillus nidulans, Aspergillus niger, Aspergillus terreus, Blastomyces dermatitidis, Candida albicans, Candida dubliniensis, Candida glabrata, Candida parapsilosis, Candida rugosa, Candida tropicalis, Cryptococcus albidus, Cryptococcus gattii, Cryptococcus laurentii, Cryptococcus neoformans, Ilistoplasma capsulatum, Microsporum canis, Pneumocystis carinii, Pneumocystis jirovecii, Sporothrix schenckii, Stachbotrys chartarum, Tinea barbae, Tinea captis, Tinea corporis, Tinea cruris, Tinea faciei, Tinea incognito, Tinea nigra, Tinea versicolor, Trichophyton rubrum* and *Trichophyton tonsurans*.

21. The method of claim 14, wherein the disease-associated antigen is a tumor-associated antigen.

22. The method of claim 21, wherein the tumor associated antigen is selected from the group consisting of 5-α-reductase, α-fetoprotein ("AFP"), AM-1, APC, April, B melanoma antigen gene (BAGE), β-catenin, Bcl12, bcr-abl, Brachyury, CA-125, caspase-8 (CASP-8, also known as FLICE), Cathepsins, CD19, CD20, CD21/complement receptor 2 (CR2), CD22/BL-CAM, CD23/FcεRII, CD33, CD35/complement receptor 1 (CR1), CD44/PGP-1, CD45/leucocyte common antigen (LCA), CD46/membrane cofactor protein (MCP), CD52/CAMPATH-1, CD55/decay accelerating factor (DAF), CD59/protectin, CDC27, CDK4, carcinoembryonic antigen (CEA), c-myc, cyclooxygenase-2 (cox-2), deleted in colorectal cancer gene (DCC), DcR3, E6/E7, CGFR, EMBP, Dna78, farnesyl transferase, fibroblast growth factor-8a (FGF8a), fibroblast growth factor-8b (FGF8b), FLK-1/KDR, folic acid receptor, G250, G melanoma antigen gene family (GAGE-family), gastrin 17, gastrin-releasing hormone, ganglioside 2 (GD2)/ganglioside 3 (GD3)/ganglioside-monosialic acid-2 (GM2), gonadotropin releasing hormone (GnRH), UDP-GlcNAc:R1Man(α1-6)R2 [GlcNAc to Man(α1-6)] β1,6-N-acetylglucosaminyltransferase V (GnT V), GP1, gp100/Pme117, gp-100-in4, gp15, gp75/tyrosine-related protein-1 (gp75/TRP-1), human chorionic gonadotropin (hCG), heparanase, Her2/neu, human mammary tumor virus (HMTV), 70 kiloDalton heat-shock protein (HSP70), human telomerase reverse transcriptase (hTERT), insulin-like growth factor receptor-1 (IGFR-1), interleukin-13 receptor (IL-13R), inducible nitric oxide synthase (iNOS), Ki67, KIAA0205, K-ras, H-ras, N-ras, KSA, LKLR-FUT, melanoma antigen-encoding gene 1 (MAGE-1), melanoma antigen-encoding gene 2 (MAGE-2), melanoma antigen-encoding gene 3 (MAGE-3), melanoma antigen-encoding gene 4 (MAGE-4), mammaglobin, MAP17, Melan-A/melanoma antigen recognized by T-cells-1 (MART-1), mesothelin, MIC MT-MMPs, mucin, testes-specific antigen NY-ESO-1, osteonectin, p15, P170/MDR1, p53, p97/melanotransferrin, PAI-1, platelet-derived growth factor (PDGF), μPA, PRAME, probasin, progenipoietin, prostate-specific antigen (PSA), prostate-specific membrane antigen (PSMA), prostatic acid phosphatase (PAP), RAGE-1, Rb, RCAS1, SART-1, SSX-family, STAT3, STn, TAG-72, transforming growth factor-alpha (TGF-α), transforming growth factor-beta (TGF-β), Thymosin-beta-15, tumor necrosis factor-alpha (TNF-α), TP1, TRP-2, tyrosinase, vascular endothelial growth factor (VEGF), ZAG, p161NK4, and glutathione-S-transferase (GST).

23. The method of claim 11, wherein the immunogenic composition is administered intranasally.

24. A kit comprising the immunogenic composition of claim 1 in a first vial or container for a first administration and in a second vial or container for a second administration.

25. The method of claim 10, wherein the enhanced innate immune response comprises TLR5 activation.

26. The method of claim 25, wherein the enhanced innate immune response further comprises inflammasome activation.

27. The method of claim 19, wherein the *Escherichia coli* is selected from enterotoxigenic *Escherichia coli*, enteropathogenic *Escherichia coli*, and *Escherichia coli* O157:H7.

* * * * *